United States Patent
Sahin et al.

(10) Patent No.: US 9,295,717 B2
(45) Date of Patent: Mar. 29, 2016

(54) VACCINE COMPOSITION COMPRISING 5'-CAP MODIFIED RNA

(75) Inventors: Ugur Sahin, Mainz (DE); Andreas Kuhn, Mainz (DE); Edward Darzynkiewicz, Izabelin-Hornowek (PL); Jacek Jemielity, Warsaw (PL); Joanna Kowalska, Radom (PL)

(73) Assignees: BIONTECH AG, Mainz (DE); TRON-TRANSLATIONALE ONKOLOGIE AN DER UNIVERSITATSMEDIZIN DER JOHANNES GUTENBERG-UNIVERSITAT MAINZ GEMEINNUTZIGE GMBH, Mainz (DE); UNIWERSYTET WARSZAWSKI, Warszawa (PL)

( * ) Notice: Subject to any disclaimer, the term of this patent is extended or adjusted under 35 U.S.C. 154(b) by 755 days.

(21) Appl. No.: 13/388,560

(22) PCT Filed: Aug. 3, 2010

(86) PCT No.: PCT/EP2010/004760
§ 371 (c)(1),
(2), (4) Date: Apr. 23, 2012

(87) PCT Pub. No.: WO2011/015347
PCT Pub. Date: Feb. 10, 2011

(65) Prior Publication Data
US 2012/0195917 A1 Aug. 2, 2012

(30) Foreign Application Priority Data
Aug. 5, 2009 (EP) .................... 09010124

(51) Int. Cl.
| | |
|---|---|
| *A61K 48/00* | (2006.01) |
| *A61K 39/00* | (2006.01) |
| *A61K 39/38* | (2006.01) |
| *C12N 5/00* | (2006.01) |
| *C12N 5/02* | (2006.01) |
| *C12N 15/00* | (2006.01) |

(52) U.S. Cl.
CPC ......... *A61K 39/00* (2013.01); *A61K 2039/5154* (2013.01); *A61K 2039/53* (2013.01)

(58) Field of Classification Search
CPC .............. A61K 39/00; A61K 2039/53; A61K 2039/5154
See application file for complete search history.

(56) References Cited

U.S. PATENT DOCUMENTS 5,994,126 A 11/1999 Steinman et al.
8,153,773 B2 * 4/2012 Jemielity et al. ............. 536/23.1

FOREIGN PATENT DOCUMENTS

| DE | 102008061522.6 A1 | 6/2010 |
|---|---|---|
| JP | 2007/512030 A | 5/2007 |
| JP | 2009/509516 A | 3/2009 |
| WO | 9633739 A1 | 10/1996 |
| WO | 2004/039398 A1 | 5/2004 |
| WO | 2006/004648 | 1/2006 |
| WO | 2007/008734 A2 | 1/2007 |
| WO | 2007036366 A2 | 4/2007 |

(Continued)

OTHER PUBLICATIONS

Int'l Prelim. Report on Patentability dated Feb. 7, 2012, PCT/EP2010/004760, 6 pages.

(Continued)

*Primary Examiner* — Lawrence E Crane
(74) *Attorney, Agent, or Firm* — McAndrews Held & Malloy Ltd.

(57) ABSTRACT

The present invention relates to modification of RNA with 5'-cap analogs of Formula (1):

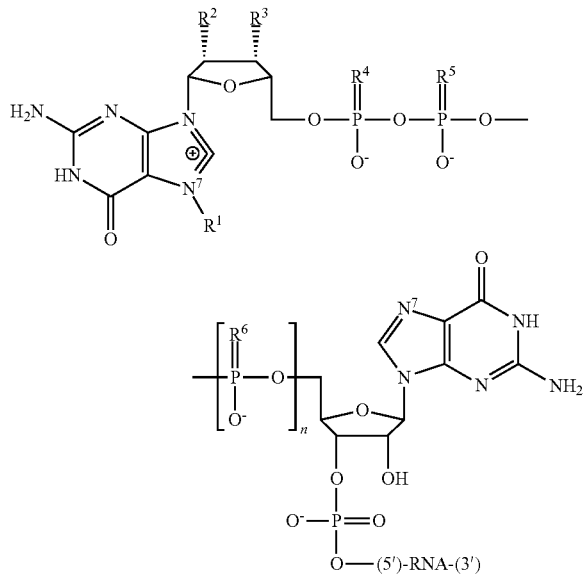

Formula (I)

wherein $R^1$-$R^6$ and n are as described herein, in order to improve the stability and increase the expression of said RNA, in particular in immature antigen presenting cells. The present invention provides a vaccine composition comprising said stabilized RNA, immature antigen presenting cells comprising said stabilized RNA, and methods for stimulating and/or activating immune effector cells and for inducing an immune response in an individual using said stabilized RNA.

16 Claims, 7 Drawing Sheets

(56) References Cited

FOREIGN PATENT DOCUMENTS

| WO | 2007/096278 | A1 | 8/2007 |
|---|---|---|---|
| WO | 2008/157688 | | 12/2008 |
| WO | 2009/046738 | | 4/2009 |

OTHER PUBLICATIONS

Wolff et al., 1990, Science, 247: 1465-1468.
Cox et al., 1993, J. Virol. 67: 5664-5667.
Davis et al., 1993, Hum. Mol. Genet. 2: 1847-1851.
Ulmer et al., 1993, Science 259:1745-1749.
Wang et al., 1993, Proc. Natl. Acad. Sci. U.S.A. 90: 4156-4160.
Conry et al., 1994, Cancer Res. 54: 1164-1168.
Conry et al., 1995, Gene Ther. 2: 59-65.
Spooner et al., 1995, Gene Ther. 2: 173-180.
Wang et al., 1995, Hum. Gene Ther. 6: 407-418.
Gilkeson et al., 1995, J. Clin. Invest. 95: 1398-1402.
Bargmann et al., 1986, Nature 319: 226-230.
Greenblatt et al., 1994, Cancer Res. 54: 4855-4878.
Condon et al., 1996, Nat. Med. 2: 1122-1128.
Tang et al., 1992, Nature 356: 152-154.
Hoerr et al., 2000, Eur. J. Immunol. 30: 1-7.
Ying et al., 1999, Nat. Med. 5: 823-827.
Heiser et al., 2000, J. Immunol. 164: 5508-5514.
Su et al., 2003, Cancer Res. 63: 2127-2133.
Heiser et al. 2002, J. Clin. Invest. 109: 409-417.
So et al., 1997, Mol. Cells 7: 178-186.
Krieg et al., 1995, Nature 374: 546-549.
Steinman (1991, Annu. Rev. Immunol. 9: 271-296.
Sallusto and Lanzavecchia (J. Exp. Med., 179: 1109-1118, 1994.
S. M. Berge et al., "Pharmaceutical Salts", J. Pharm. Sci., 66, pp. 1-19 (1977).
Stepinski et al., 2001; RNA J. 7: 1486-1495.
Peng et al., 2002; Org. Lett. 24: 161-164.
Kore et al. 2009, J. Am. Chem. Soc. 131: 6364-6365.
Shimonkevitz et al., 1983, J. Exp. Med. 158: 303-316.
Holtkamp et al., 2006, Blood 108: 4009-4017.
Pokrovskava & Gurevich, 1994, Anal. Biochem. 220: 420-423.
Darzynkiewicz et al., 1988, Nucleic Acids Res. 16: 8953-8962.
Stepinski et al., 1995, Nucleosides Nucleotides 14: 717-721.
Grudzien et al., 2004, RNA J. 10: 1479-1487.
Kreiter et al., 2008, J. Immunol. 180: 309-318.
Grudzien-Nogalska et al., "Phosphorothioate cap analogs stabilize mRNA and increase translational efficiency in mammalian cells," RNA, 13(10):1746-1755 (2007) XP002554207.
International Search Report and Written Opinion in PCT/EP2010/004760, dated Nov. 8, 2010.
Kowalska et al., "Synthesis and characterization of mRNA cap analogs containing phosphorothioate substitutions that bind tightly to eIF4E and are resistant to the decapping pyrophosphatase DcpS," RNA, 14(6):1119-1131 (2008) XP002554206.
Kuhn et al., "Phosphorothioate cap analogs increase stability and translational efficiency of RNA vaccines in immature dendritic cells and induce superior immune responses in vivo," Gene Therapy, 17(8):961-971 (2010) XP002607370.

\* cited by examiner

VACCINE COMPOSITION COMPRISING 5'-CAP MODIFIED RNA

CROSS-REFERENCE TO RELATED APPLICATIONS

This application is filed pursuant to 35 U.S.C. 371 as a U.S. National Phase application of International Patent Application No. PCT/EP2010/004760, which was filed Aug. 3, 2010, and which claims priority to European Patent Application No. 09010124.7, which was filed Aug. 5, 2009. The entire text of the aforementioned applications is incorporated herein by reference in its entirety.

TECHNICAL FIELD OF THE INVENTION

The present invention is in the field of nucleic acid based vaccination. In particular, the present invention relates to stabilization of RNA by modification, in particular in the context of RNA vaccination, and provides a vaccine composition comprising an RNA which is modified with a 5'-cap analog, immature antigen-presenting cells comprising such RNA, as well as methods for eliciting an immune response in an individual using the vaccine composition or the immature antigen-presenting cells according to the present invention. Furthermore, the present invention provides a method for increasing the stability of RNA in immature antigen-presenting cells, a method for increasing the expression of RNA in immature antigen presenting cells, a method for increasing the portion of MHC molecules which present an antigen of interest, and a method for stimulating and/or activating immune effector cells.

BACKGROUND OF THE INVENTION

Recombinant vaccines are of particular importance in human and veterinary medicine for prophylaxis and therapy of infectious and cancerous diseases. It is the aim of an immunization with a recombinant vaccine to induce a specific immune reaction against a defined antigen, which is effective in prevention or therapy of defined diseases. Known recombinant vaccines are based on recombinant proteins, synthetic peptide fragments, recombinant viruses, or nucleic acids.

Recently, DNA and RNA based vaccines have gained more importance. It has been shown that direct intramuscular injection of plasmid DNA results in a long-lasting expression of the encoded genes (Wolff et al., 1990, Science, 247: 1465-1468). This finding was a major incentive in the field to further investigate the applicability of nucleic acids in immunotherapy. At first, DNA based vaccines against infectious pathogens have been studied (Cox et al., 1993, J. Virol. 67: 5664-5667; Davis et al., 1993, Hum. Mol. Genet. 2: 1847-1851; Ulmer et al., 1993, Science 259: 1745-1749; Wang et al., 1993, Proc. Natl. Acad. Sci. U.S.A. 90: 4156-4160). Furthermore, the applicability of nucleic acids in gene therapy against tumors and for induction of a specific anti-tumor immunity has been studied (Conry et al., 1994, Cancer Res. 54: 1164-1168; Conry et al., 1995, Gene Ther. 2: 59-65; Spooner et al., 1995, Gene Ther. 2: 173-180; Wang et al., 1995, Hum. Gene Ther. 6: 407-418).

Nucleic acid based immunization exhibits a number of advantages. For example, the manufacture of nucleic acid based vaccines is straight forward, relatively inexpensive, and DNA based vaccines are stable for long-term storage. However, in particular, DNA based vaccines exhibit a variety of potential safety risks such as induction of anti-DNA antibodies (Gilkeson et al., 1995, J. Clin. Invest. 95: 1398-1402) and potential integration of the transgene into the host genome. This may lead to the inactivation of cellular genes, an uncontrollable long term expression of the transgene, or oncogenesis, and thus, is generally not applicable for tumor-associated antigens with oncogenic potential such as erb-B2 (Bargmann et al., 1986, Nature 319: 226-230) and p53 (Greenblatt et al., 1994, Cancer Res. 54: 4855-4878).

The use of RNA provides an attractive alternative to circumvent the potential risks of DNA based vaccines. Some of the advantages of RNA based immunization are the transient expression and the non-transforming character. Furthermore, RNA does not have to be transported into the nucleus for the transgene to be expressed, and moreover, cannot be integrated into the host genome. Similar to the injection of DNA (Condon et al., 1996, Nat. Med. 2: 1122-1128; Tang et al., 1992, Nature 356: 152-154), the injection of RNA may result in both a cellular as well as a humoral immune response in vivo (Hoerr et al., 2000, Eur. J. Immunol. 30: 1-7; Ying et al., 1999, Nat. Med. 5: 823-827).

Two different strategies have been pursued for immunotherapy with in vitro transcribed RNA (IVT-RNA), which have both been successfully tested in various animal models. Either the RNA is directly injected into the patient by different immunization routes (Hoerr et al., 2000, Eur. J. Immunol. 30: 1-7) or dendritic cells are transfected with IVT-RNA using conventional transfection methods in vitro and then the transfected dendritic cells are administered to the patient (Heiser et al., 2000, J. Immunol. 164: 5508-5514). It has been shown that immunization with RNA transfected dendritic cells induces antigen-specific cytotoxic T-lymphocytes (CTL) in vitro and in vivo (Su et al., 2003, Cancer Res. 63: 2127-2133; Heiser et al., 2002, J. Clin. Invest. 109: 409-417). Furthermore, it has been shown that direct injection of naked RNA into the lymph nodes of laboratory animals (intranodal injection) leads to uptake of said RNA primarily by immature dendritic cells, probably by a process called macropinocytosis (cf. DE 10 2008 061 522.6). It is assumed that the RNA is translated and the expressed protein is presented on the MHC molecules on the surface of the antigen presenting cells to elicit an immune response.

A major disadvantage of RNA based vaccination is the instability of the RNA in vivo, in particular in the cells of the immune system. Degradation of long-chain RNA from the 5'-end is induced in the cell by the so called "decapping" enzyme Dcp2 which cleaves $m^7GDP$ from the RNA chain. Thus, it is assumed that the cleavage occurs between the alpha- and beta-phosphate groups of the RNA-cap.

To inhibit the decapping process and thus increase the stability of RNA in vivo, the effect of phosphorothioate-cap-analogs on the stability of said RNA has been studied. It has been shown that the substitution of an oxygen atom for a sulphur atom at the beta-phosphate group of the 5'-cap results in stabilization against Dcp2. The phosphorothioate modification of the RNA 5'-cap has been combined with an "anti-reverse cap analog" (ARCA) modification that inhibits the reverse integration of the cap into an RNA chain. The resulting cap analog, i.e., $m_2^{(7,2'-O)}Gpp_sPG$, was termed beta-S-ARCA (cf. FIG. 1). The replacement of an oxygen atom for a sulphur atom at a bridging phosphate results in phosphorothioate diastereomers which are designated D1 and D2 based on their elution pattern in HPLC. Interestingly, the two diastereomers differ in sensitivity against nucleases. It has been shown that RNA carrying the D2 diastereomer of beta-S-ARCA is almost fully resistant against Dcp2 cleavage (only 6% cleavage compared to RNA which has been synthesized in presence of the unmodified ARCA 5'-cap), whereas RNA with the beta-S-ARCA(D1) 5'-cap exhibits an intermediary sensitivity to Dcp2 cleavage (71% cleavage). Furthermore, the three cap-analogs ARCA, beta-S-ARCA(D1), and beta-S-ARCA(D2) differ in their binding affinity to the eukaryotic translation initiation factor eIF4E. Both of the phosphorothioate cap analogs possess higher affinity for eIF4E than RNAs having conventional 5'-caps. It has further been shown that the increased stability against Dcp2 cleavage correlates with increased protein expression in HC11 cells. In particular, it has been shown that RNAs carrying the beta-S-ARCA(D2) cap are more efficiently translated in HC11 cells than RNAs carrying the beta-S-ARCA(D1) cap.

In summary, RNA is especially well-suited for clinical applications. However, the use of RNA in gene therapy and RNA vaccination is primarily limited by the short half-life of RNA, in particular in the cytoplasm, which results in low and/or insufficient protein expression. Thus, for RNA vaccination it is of particular importance to increase RNA stability in antigen-presenting cells. Since naked RNA injected into the lymph nodes is primarily taken up by immature antigen presenting cells, in particular by immature dendritic cells, it is of particular importance in the context of RNA vaccination to increase the stability of RNA in immature antigen presenting cells. Thus, it is the object of the present invention to provide RNA which is particularly suited for RNA vaccination, i.e., to provide means to particularly stabilize RNA in immature antigen-presenting cells. This technical problem is solved according to the present invention by the subject-matter of the claims.

SUMMARY OF THE INVENTION

In a first aspect, the present invention provides a vaccine composition comprising an RNA which is modified with a 5'-cap structure according to formula (I) (with the attachment of the RNA shown):

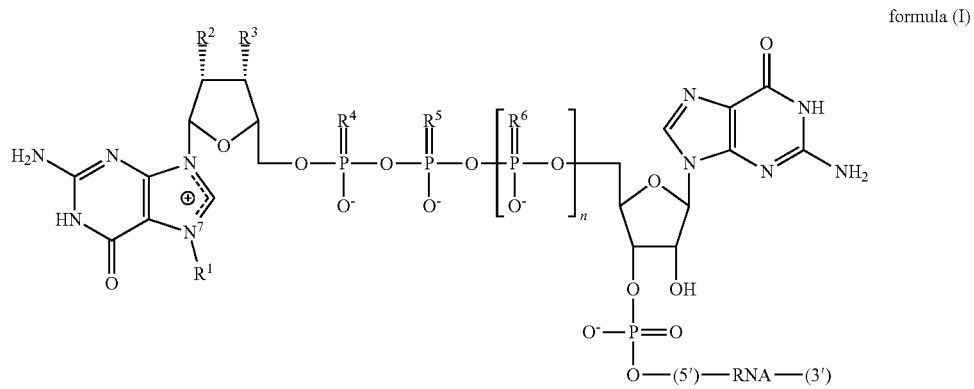

formula (I)

wherein $R^1$ is selected from the group consisting of optionally substituted alkyl, optionally substituted alkenyl, optionally substituted alkynyl, optionally substituted cycloalkyl, optionally substituted heterocyclyl, optionally substituted aryl, and optionally substituted heteroaryl, $R^2$ and $R^3$ are independently selected from the group consisting of H, halo, OH, and optionally substituted alkoxy, or $R^2$ and $R^3$ together form O—X—O, wherein X is selected from the group consisting of optionally substituted $CH_2$, $CH_2CH_2$, $CH_2CH_2CH_2$, $CH_2CH(CH_3)$, and $C(CH_3)_2$, or $R^2$ is combined with the valence produced by removal of the hydrogen atom at position 4' of the ring to which $R^2$ is attached, wherein the bridging linkage from $R^2$ to the 4' position is defined as an —O—$CH_2$— group or —$CH_2$—O— group, $R^5$ is selected from the group consisting of S, Se, and $BH_3$, $R^4$ and $R^6$ are independently selected from the group consisting of O, S, Se, and $BH_3$, n is 1, 2, or 3, wherein the stereochemical configuration at the P atom comprising the substituent $R^5$ corresponds to that at the $P_\beta$ atom of the D1 diastereomer of beta-S-ARCA.

In a preferred embodiment, the 5'-cap structure upon transfer of said RNA into immature antigen presenting cells is capable of increasing the stability of the RNA, increasing translation efficiency of the RNA, prolonging translation of the RNA, increasing total protein expression of the RNA, and/or increasing the immune response against an antigen or antigen peptide encoded by said RNA when compared to the same RNA without the 5'-cap structure according to formula (I).

In a preferred embodiment, $R^1$ is selected from the group consisting of optionally substituted $C_1$-$C_4$ alkyl, optionally substituted $C_2$-$C_4$ alkenyl, and optionally substituted aryl.

In a preferred embodiment, $R^2$ and $R^3$ are independently selected from the group consisting of H, F, OH, methoxy, ethoxy, and propoxy.

In a particularly preferred embodiment, the RNA 5'-cap is the diastereomer D1 of beta-S-ARCA.

Preferably, the vaccine composition is formulated for intranodal injection.

In a second aspect, the present invention provides an immature antigen presenting cell comprising an RNA which is modified with a 5'-cap structure according to formula (I) (with the attachment of the RNA shown):

$CH_2CH_2CH_2$, $CH_2CH(CH_3)$, and $C(CH_3)_2$, or $R^2$ is combined with the valence produced by removal of the hydrogen atom at position 4' of the ring to which $R^2$ is attached, wherein the bridging linkage from $R^2$ to the 4' position is defined as an —O—$CH_2$— group or —$CH_2$—O— group, $R^5$ is selected from the group consisting of S, Se, and $BH_3$, $R^4$ and $R^6$ are independently selected from the group consisting of O, S, Se, and $BH_3$, n is 1, 2, or 3, wherein the stereochemical configuration at the P atom comprising the substituent $R^5$ corresponds to that at the $P_\beta$ atom of the D1 diastereomer of beta-S-ARCA.

In a third aspect, the present invention provides a method for eliciting an immune response in an individual comprising the step of administering to said individual the vaccine com-

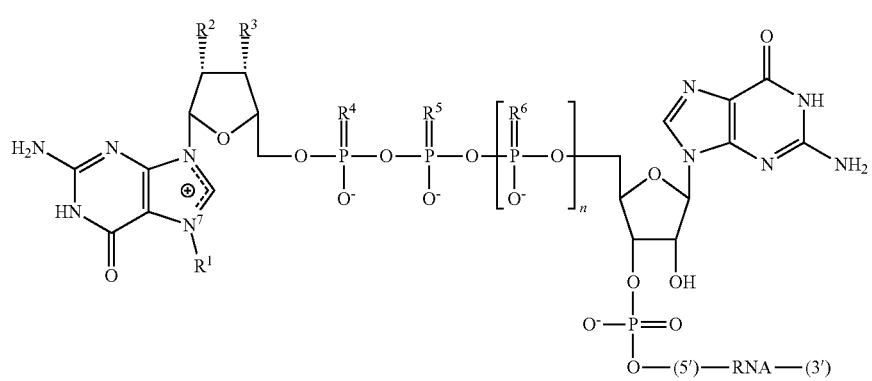

formula (I)

wherein $R^1$ is selected from the group consisting of optionally substituted alkyl, optionally substituted alkenyl, optionally substituted alkynyl, optionally substituted cycloalkyl, optionally substituted heterocyclyl, optionally substituted aryl, and optionally substituted heteroaryl, $R^2$ and $R^3$ are independently selected from the group consisting of H, halo, OH, and optionally substituted alkoxy, or $R^2$ and $R^3$ together form O—X—O, wherein X is selected from the group consisting of optionally substituted $CH_2$, $CH_2CH_2$, position of the first aspect of the invention or the immature antigen presenting cell of the second aspect of the invention.

In a fourth aspect, the present invention provides a method for increasing the stability of an RNA in immature antigen presenting cells and/or for increasing the expression of an RNA in immature antigen presenting cells, said method comprising:

providing said RNA with a 5'-cap structure according to formula (I) (with the attachment of the RNA shown):

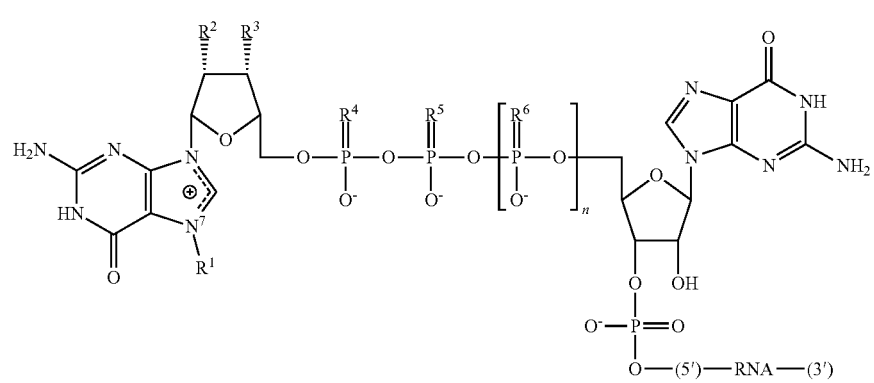

formula (I)

wherein $R^1$ is selected from the group consisting of optionally substituted alkyl, optionally substituted alkenyl, optionally substituted alkynyl, optionally substituted cycloalkyl, optionally substituted heterocyclyl, optionally substituted aryl, and optionally substituted heteroaryl, $R^2$ and $R^3$ are independently selected from the group consisting of H, halo, OH, and optionally substituted alkoxy, or $R^2$ and $R^3$ together form O—X—O, wherein X is selected from the group consisting of optionally substituted $CH_2$, $CH_2CH_2$, $CH_2CH_2CH_2$, $CH_2CH(CH_3)$, and $C(CH_3)_2$, or $R^2$ is combined with the valence produced by removal of the hydrogen atom at position 4' of the ring to which $R^2$ is attached, wherein the bridging linkage from $R^2$ to the 4' position is defined as an —O—$CH_2$— group or —$CH_2$—O— group, $R^5$ is selected from the group consisting of S, Se, and $BH_3$, $R^4$ and $R^6$ are independently selected from the group consisting of O, S, Se, and $BH_3$, n is 1, 2, or 3, wherein the stereochemical configuration at the P atom comprising the substituent $R^5$ corresponds to that at the $P_\beta$ atom of the D1 diastereomer of beta-S-ARCA, and transferring said RNA into the immature antigen presenting cells.

In a fifth aspect, the present invention provides a method for increasing the portion of MHC molecules which present an antigen of interest on the surface of an antigen presenting cell, said method comprising:

providing an RNA comprising a nucleotide sequence encoding a peptide or protein comprising said antigen of interest or an antigen peptide thereof, said RNA being modified with a 5'-cap structure according to formula (I) (with the attachment of the RNA shown):

wherein $R^1$ is selected from the group consisting of optionally substituted alkyl, optionally substituted alkenyl, optionally substituted alkynyl, optionally substituted cycloalkyl, optionally substituted heterocyclyl, optionally substituted aryl, and optionally substituted heteroaryl, $R^2$ and $R^3$ are independently selected from the group consisting of H, halo, OH, and optionally substituted alkoxy, or $R^2$ and $R^3$ together form O—X—O, wherein X is selected from the group consisting of optionally substituted $CH_2$, $CH_2CH_2$, $CH_2CH_2CH_2$, $CH_2CH(CH_3)$, and $C(CH_3)_2$, or $R^2$ is combined with the valence produced by removal of the hydrogen atom at position 4' of the ring to which $R^2$ is attached, wherein the bridging linkage from $R^2$ to the 4' position is defined as an —O—$CH_2$— group or —$CH_2$—O— group, $R^5$ is selected from the group consisting of S, Se, and $BH_3$, $R^4$ and $R^6$ are independently selected from the group consisting of O, S, Se, and $BH_3$, n is 1, 2, or 3, wherein the stereochemical configuration at the P atom comprising the substituent $R^5$ corresponds to that at the $P_\beta$ atom of the D1 diastereomer of beta-S-ARCA, and transferring said RNA into an immature antigen presenting cell.

In a sixth aspect, the present invention provides a method for stimulating and/or activating immune effector cells, said method comprising:

providing an RNA comprising a nucleotide sequence encoding a peptide or protein comprising an antigen of interest or an antigen peptide thereof, said RNA being modified with a 5'-cap structure according to formula (I) (with the attachment of the RNA shown):

formula (I)

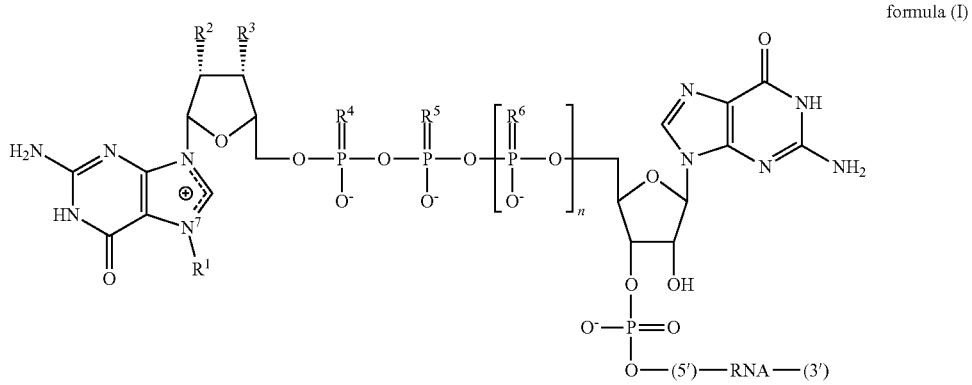

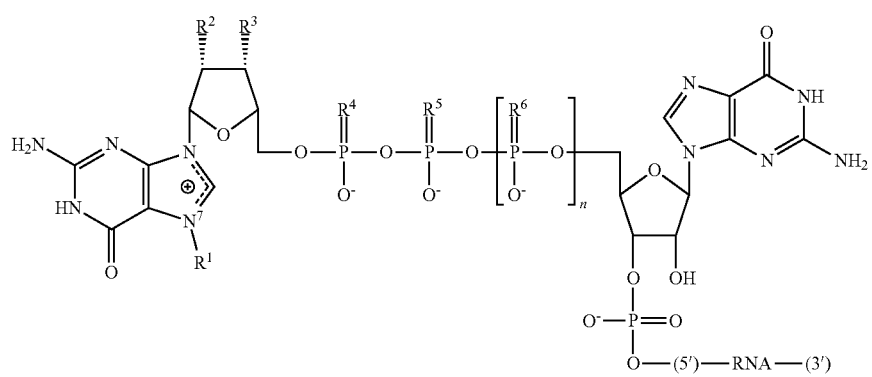

formula (I)

wherein $R^1$ is selected from the group consisting of optionally substituted alkyl, optionally substituted alkenyl, optionally substituted alkynyl, optionally substituted cycloalkyl, optionally substituted heterocyclyl, optionally substituted aryl, and optionally substituted heteroaryl, $R^2$ and $R^3$ are independently selected from the group consisting of H, halo, OH, and optionally substituted alkoxy, or $R^2$ and $R^3$ together form O—X—O, wherein X is selected from the group consisting of optionally substituted $CH_2$, $CH_2CH_2$, $CH_2CH_2CH_2$, $CH_2CH(CH_3)$, and $C(CH_3)_2$, or $R^2$ is combined with the valence produced by removal of the hydrogen atom at position 4' of the ring to which $R^2$ is attached, wherein the bridging linkage from $R^2$ to the 4' position is defined as an —O—$CH_2$— group or —$CH_2$—O— group, $R^5$ is selected from the group consisting of S, Se, and $BH_3$, $R^4$ and $R^6$ are independently selected from the group consisting of O, S, Se, and $BH_3$, n is 1, 2, or 3, wherein the stereochemical configuration at the P atom comprising the substituent $R^5$ corresponds to that at the $P_\beta$ atom of the D1 diastereomer of beta-S-ARCA, transferring said RNA into immature antigen presenting cells, and contacting the antigen presenting cells with the immune effector cells.

Contacting the antigen presenting cells with the immune effector cells may be accomplished in vitro or in vivo.

In a seventh aspect, the present invention provides a method for inducing an immune response in an individual, said method comprising: providing an RNA comprising a nucleotide sequence encoding a peptide or protein comprising an antigen of interest or an antigen peptide thereof, said RNA being modified with a 5'-cap structure according to formula (I) (with the attachment of the RNA shown):

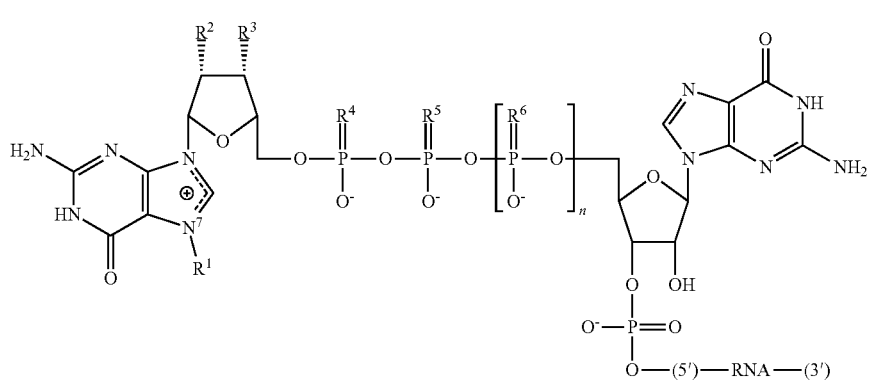

formula (I)

wherein $R^1$ is selected from the group consisting of optionally substituted alkyl, optionally substituted alkenyl, optionally substituted alkynyl, optionally substituted cycloalkyl, optionally substituted heterocyclyl, optionally substituted aryl, and optionally substituted heteroaryl, $R^2$ and $R^3$ are independently selected from the group consisting of H, halo, OH, and optionally substituted alkoxy, or $R^2$ and $R^3$ together form O—X—O, wherein X is selected from the group consisting of optionally substituted $CH_2$, $CH_2CH_2$, $CH_2CH_2CH_2$, $CH_2CH(CH_3)$, and $C(CH_3)_2$, or $R^2$ is combined with the valence produced by removal of the hydrogen atom at position 4' of the ring to which $R^2$ is attached, wherein the bridging linkage from $R^2$ to the 4' position is defined as an —O—$CH_2$— group or —$CH_2$—O— group, $R^5$ is selected from the group consisting of S, Se, and $BH_3$, $R^4$ and $R^6$ are independently selected from the group consisting of O, S, Se, and $BH_3$, n is 1, 2, or 3, wherein the stereochemical configuration at the P atom comprising the substituent $R^5$ corresponds to that at the $P_\beta$ atom of the D1 diastereomer of beta-S-ARCA, and administering said RNA to said individual.

In a preferred embodiment, the RNA is administered by intranodal injection.

In an eighth aspect, the present invention provides a method for inducing an immune response in an individual, said method comprising:
providing an RNA comprising a nucleotide sequence encoding a peptide or protein comprising an antigen of interest or an antigen peptide thereof, said RNA being modified with a 5'-cap structure according to formula (I) (with the attachment of the RNA shown):

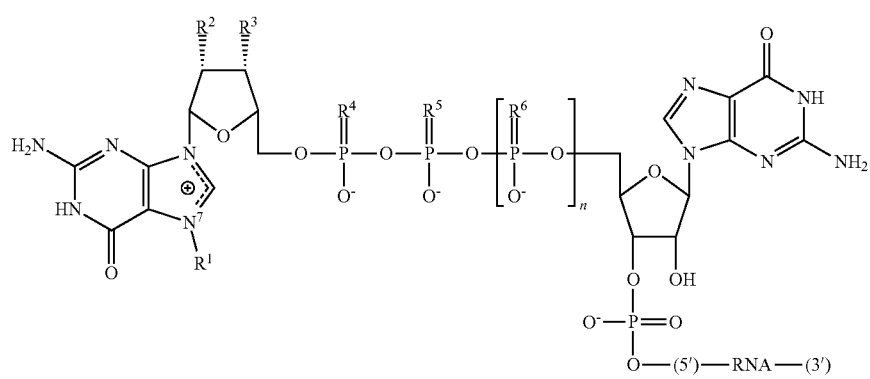

formula (I)

wherein $R^1$ is selected from the group consisting of optionally substituted alkyl, optionally substituted alkenyl, optionally substituted alkynyl, optionally substituted cycloalkyl, optionally substituted heterocyclyl, optionally substituted aryl, and optionally substituted heteroaryl,
$R^2$ and $R^3$ are independently selected from the group consisting of H, halo, OH, and optionally substituted alkoxy, or $R^2$ and $R^3$ together form O—X—O, wherein X is selected from the group consisting of optionally substituted $CH_2$, $CH_2CH_2$, $CH_2CH_2CH_2$, $CH_2CH(CH_3)$, and $C(CH_3)_2$, or $R^2$ is combined with the valence produced by removal of the hydrogen atom at position 4' of the ring to which $R^2$ is attached, wherein the bridging linkage from $R^2$ to the 4' position is defined as an —O—$CH_2$— group or —$CH_2$—O— group,
$R^5$ is selected from the group consisting of S, Se, and $BH_3$,
$R^4$ and $R^6$ are independently selected from the group consisting of O, S, Se, and $BH_3$,
n is 1, 2, or 3,
wherein the stereochemical configuration at the P atom comprising the substituent $R^5$ corresponds to that at the $P_\beta$ atom of the D1 diastereomer of beta-S-ARCA,
transferring said RNA into immature antigen presenting cells, and
administering the antigen presenting cells to said individual.

BRIEF DESCRIPTION OF THE DRAWINGS

FIG. 4. Impact of the 5'-cap on the stability of mRNAs in dendritic cells. (A) Immature dendritic cells (iDCs) and (B) mature dendritic cells (mDCs) were electroporated with equal amounts of d2eGFP-encoding mRNAs transcribed in the presence of different cap analogs as indicated. Cells were harvested after 2, 4, 8, 24, 48, and 72 hours, and the d2eGFP-transcript levels were quantified by real-time RT-PCR. For each time point, the difference between the threshold cycles (Ct) of RNAs encoding d2eGFP and hypoxanthine phosphoribosyltransferase (HPRT1) used as internal control is shown. The data were fitted to a biphasic decay (iDCs.

DETAILED DESCRIPTION OF THE INVENTION

Figure 1:
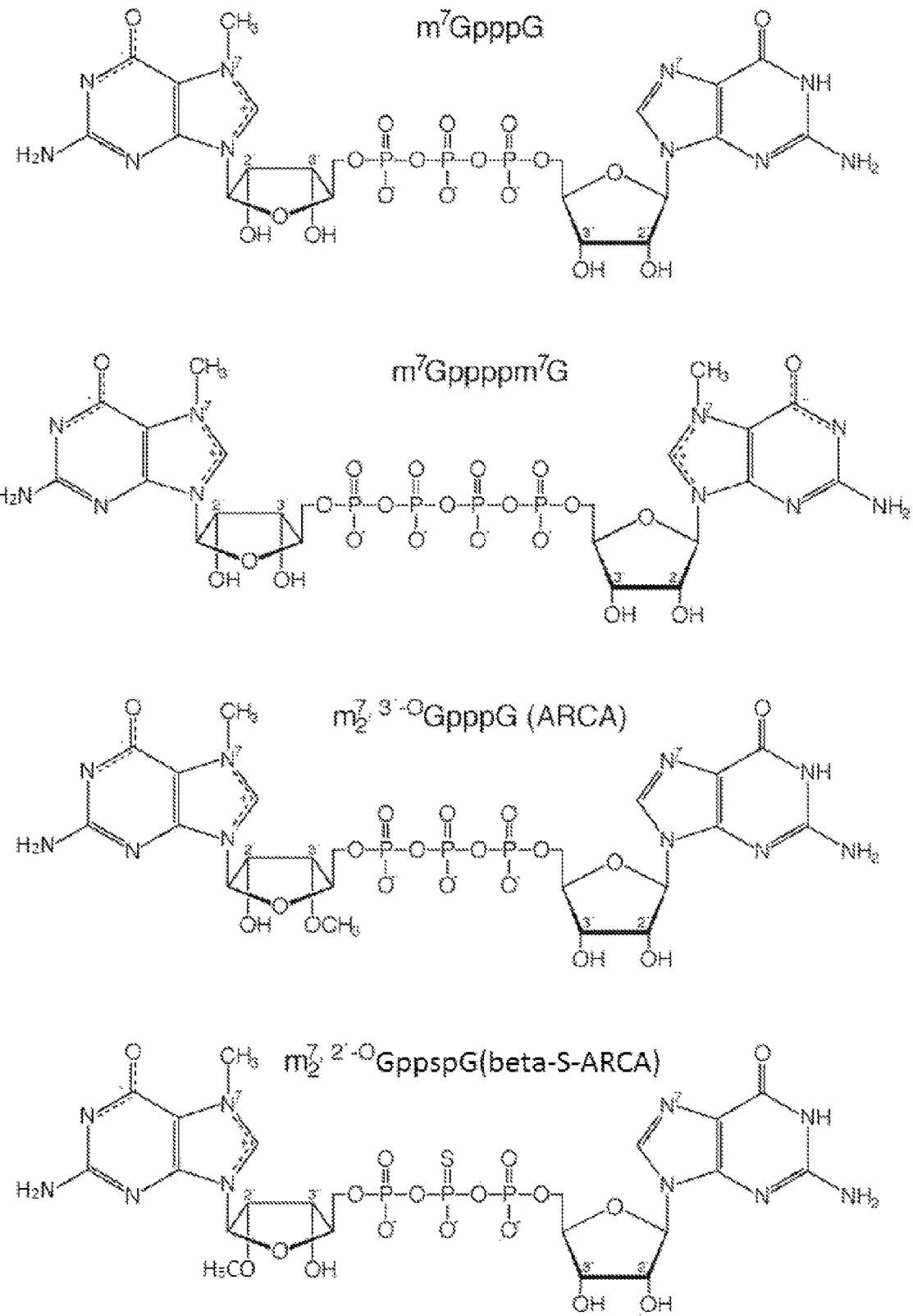
FIG. 1. Structures of 5'-cap dinucleotides. There are two diastereomers of the phosphorothioate cap analog beta-S-ARCA due to the stereogenic P center, which are designated D1 and D2 according to their elusion characteristics in reverse phase HPLC.

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise. For example, if in a preferred embodiment $R^2$ of the 5'-cap structure is methoxy and in another preferred embodiment $R^5$ of the 5'-cap structure is S, then in a preferred embodiment, $R^2$ of the 5'-cap structure is methoxy and $R^5$ is S.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present invention will employ, unless otherwise indicated, conventional methods of chemistry, biochemistry, and recombinant DNA techniques which are explained in the literature in the field (cf., e.g., *Molecular Cloning: A Laboratory Manual*, $2^{nd}$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

According to the invention, the term "nucleic acid" comprises deoxyribonucleic acid (DNA), ribonucleic acid (RNA), combinations thereof, and modified forms thereof. The term comprises genomic DNA, cDNA, mRNA, recombinantly produced and chemically synthesized molecules. According to the invention, a nucleic acid may be present as a single-stranded or double-stranded and linear or covalently circularly closed molecule. A nucleic acid can, according to the invention, be isolated. The term "isolated nucleic acid" means, according to the invention, that the nucleic acid (i) was amplified in vitro, for example via polymerase chain reaction (PCR), (ii) was produced recombinantly by cloning, (iii) was purified, for example, by cleavage and separation by gel electrophoresis, or (iv) was synthesized, for example, by chemical synthesis.

In the context of the present invention, the term "RNA" relates to a molecule which comprises at least one ribonucleotide residue. "Ribonucleotide" relates to a nucleotide with a hydroxyl group at the 2'-position of a β-D-ribofuranosyl group. The term comprises double-stranded RNA, single-stranded RNA, isolated RNA such as partially or completely purified RNA, essentially pure RNA, synthetic RNA, recombinantly generated RNA such as modified RNA which differs from naturally occurring RNA by addition, deletion, substitution and/or alteration of one or more nucleotides. The term "mRNA" means "messenger-RNA" and relates to a "transcript" which is generated by using a DNA template and encodes a peptide or protein. Typically, an mRNA comprises a 5'-UTR, a protein coding region and a 3'-UTR. mRNA only possesses limited half-life in cells and in vitro. In the context of the present invention, mRNA may be generated by in vitro transcription from a DNA template. The in vitro transcription methodology is known to the skilled person. For example, there is a variety of in vitro transcription kits commercially available. In the context of the present invention, the RNA, preferably the mRNA, is modified with a 5'-cap structure.

In a preferred embodiment, RNA according to the invention encodes a peptide or protein comprising one or more antigens and/or one or more antigen peptides and is capable of expressing said peptide or protein comprising one or more antigens and/or one or more antigen peptides, in particular if transferred into a cell such as an immature antigen presenting cell. RNA may also contain sequences which encode other polypeptide sequences such as immune stimulating elements. Furthermore, it may contain elements which participate in regulation of expression (for example, 5'- or 3'-UTR sequences etc.).

The term "modification" in the context of the RNA used in the present invention includes any modification of an RNA which is not naturally present in said RNA. In particular, the term modification relates to providing an RNA with a 5'-cap analog having a structure as set forth in formula (I). For example, providing an RNA with a 5'-cap analog may be achieved by in vitro transcription of a DNA template in presence of said 5'-cap analog, wherein said 5'-cap is co-transcriptionally incorporated into the generated RNA strand, or the RNA may be generated, for example, by in vitro transcription, and the 5'-cap may be attached to the RNA post-transcriptionally using capping enzymes, for example, capping enzymes of vaccinia virus. The RNA may comprise further modifications. For example, a further modification of the RNA used in the present invention, preferably the mRNA used in the present invention, may be an extension or truncation of the naturally occurring poly(A) tail or an alteration of the 5'- or 3'-untranslated regions (UTR) such as introduction of a UTR which is not related to the coding region of said RNA, preferably said mRNA, for example, the exchange of the existing 3'-UTR with or the insertion of one or more, preferably two copies of a 3'-UTR derived from a globin gene, such as alpha2-globin, alpha1-globin, beta-globin, preferably beta-globin, more preferably human beta-globin.

The term "5'-cap" refers to a cap structure found on the 5'-end of an mRNA molecule and generally consists of a guanosine nucleotide connected to the mRNA via an unusual 5' to 5' triphosphate linkage. In one embodiment, this guanosine is methylated at the 7-position. The term "conventional 5'-cap" refers to a naturally occurring RNA 5'-cap, preferably to the 7-methylguanosine cap ($m^7G$). In the context of the present invention, the term "5'-cap" includes a 5'-cap analog that resembles the RNA cap structure and is modified to possess the ability to stabilize RNA if attached thereto, preferably in vivo, preferably in immature antigen presenting cells, most preferably in immature dendritic cells. The 5'-cap used in the present invention exhibits a structure according to formula (I).

In the context of the present invention, the term "vaccine composition" relates to an antigenic preparation which comprises RNA. The vaccine composition is administered to a recipient in order to stimulate the humoral and/or cellular immune system of an individual against one or more antigens. In this context, the RNA may encode the antigen, a protein or peptide comprising said antigen or an antigen peptide. A vaccine composition in the context of the present invention may further comprise one or more adjuvant(s), diluents, carriers, and/or excipients etc. and is applied to an individual in any suitable route in order to elicit a protective and/or therapeutic immune reaction against the antigen.

For administration according to the invention, in particular, in the form of a vaccine composition, RNA may be naked RNA or may be incorporated in a carrier, for example, liposomes or other particles for gene transfer, and is preferably in the form of naked RNA.

An "antigen" according to the invention covers any substance that will elicit an immune response. In particular, an "antigen" relates to any substance that reacts specifically with antibodies or T-lymphocytes (T-cells). According to the present invention, the term "antigen" comprises any molecule which comprises at least one epitope. Preferably, an antigen in the context of the present invention is a molecule which, optionally after processing, induces an immune reaction, which is preferably specific for the antigen. According to the present invention, any suitable antigen may be used, which is a candidate for an immune reaction, wherein the immune reaction may be both a humoral as well as a cellular immune reaction. In the context of the embodiments of the present invention, the antigen is preferably presented by a cell, preferably by an antigen presenting cell, in the context of MHC molecules, which results in an immune reaction against the antigen. An antigen is preferably a product which corresponds to or is derived from a naturally occurring antigen. Such naturally occurring antigens may include or may be derived from allergens, viruses, bacteria, fungi, parasites and other infectious agents and pathogens or an antigen may also be a tumor antigen. According to the present invention, an antigen may correspond to a naturally occurring product, for example, a viral protein, or a part thereof.

In a preferred embodiment, the antigen is a tumor antigen, i.e., a part of a tumor cell which may be derived from the cytoplasm, the cell surface or the cell nucleus, in particular those which primarily occur intracellularly or as surface antigens of tumor cells. For example, tumor antigens include the carcinoembryonal antigen, α1-fetoprotein, isoferritin, and fetal sulphoglycoprotein, α2-H-ferroprotein and γ-fetoprotein, as well as various virus tumor antigens. According to the present invention, a tumor antigen preferably comprises any antigen which is characteristic for tumors or cancers as well as for tumor or cancer cells with respect to type and/or expression level. In another embodiment, the antigen is a virus antigen such as viral ribonucleoprotein or coat protein. In particular, the antigen should be presented by MHC molecules which results in modulation, in particular activation of cells of the immune system, preferably $CD4^+$ and $CD8^+$ lymphocytes, in particular via the modulation of the activity of a T-cell receptor.

In preferred embodiments, the antigen is a tumor antigen and the present invention involves the stimulation of an anti-tumor CTL response against tumor cells expressing such tumor antigen and preferably presenting such tumor antigen with class 1 MHC.

The term "immunogenicity" relates to the relative effectivity of an antigen to induce an immune reaction.

The term "pathogen" relates to pathogenic microorganisms and comprises viruses, bacteria, fungi, unicellular organisms, and parasites. Examples for pathogenic viruses are human immunodeficiency virus (HIV), cytomegalovirus (CMV), herpes virus (HSV), hepatitis A-virus (HAV), HBV, HCV, papilloma virus, and human T-lymphotrophic virus (HTLV). Unicellular organisms comprise plasmodia trypanosomes, amoeba, etc.

Examples for antigens that may be used in the present invention are p53, ART-4, BAGE, ss-catenin/m, Bcr-abL CAMEL, CAP-1, CASP-8, CDC27/m, CDK4/m, CEA, CLAUDIN-12, c-MYC, CT, Cyp-B, DAM, ELF2M, ETV6-AML1, G250, GAGE, GnT-V, Gap100, HAGE, HER-2/neu, HPV-E7, HPV-E6, HAST-2, hTERT (or hTRT), LAGE, LDLR/FUT, MAGE-A, preferably MAGE-A1, MAGE-A2, MAGE-A3, MAGE-A4, MAGE-A5, MAGE-A6, MAGE-A7, MAGE-A8, MAGE-A9, MAGE-A10, MAGE-A11, or MAGE-A12, MAGE-B, MAGE-C, MART-1/Melan-A, MC1R, Myosin/m, MUC1, MUM-1, -2, -3, NA88-A, NF1, NY-ESO-1, NY-BR-1, p190 minor BCR-abL, Plac-1, Pm1/RARa, PRAME, proteinase 3, PSA, PSM, RAGE, RU1 or RU2, SAGE, SART-1 or SART-3, SCGB3A2, SCP1, SCP2, SCP3, SSX, SURVIVIN, TEL/AML1, TPI/m, TRP-1, TRP-2, TRP-2/INT2, TPTE and WT, preferably WT-1.

"A portion or fragment of an antigen" or "an antigen peptide" according to the invention preferably is an incomplete representation of an antigen and is capable of eliciting an immune response against the antigen.

In this context, the invention also makes use of peptides comprising amino acid sequences derived from antigens, also termed "antigen peptides" herein. By "antigen peptide", or "antigen peptide derived from an antigen" is meant an oligopeptide or polypeptide comprising an amino acid sequence substantially corresponding to the amino acid sequence of a fragment or peptide of an antigen. An antigen peptide may be of any length.

Preferably, the antigen peptides are capable of stimulating an immune response, preferably a cellular response against the antigen or cells characterized by expression of the antigen and preferably by presentation of the antigen. Preferably, an antigen peptide is capable of stimulating a cellular response against a cell characterized by presentation of an antigen with class I MHC and preferably is capable of stimulating an antigen-responsive CTL. Preferably, the antigen peptides according to the invention are MHC class I and/or class II presented peptides or can be processed to produce MHC class I and/or class II presented peptides. Preferably, the antigen peptides comprise an amino acid sequence substantially corresponding to the amino acid sequence of a fragment of an antigen. Preferably, said fragment of an antigen is an MHC class I and/or class II presented peptide. Preferably, an antigen peptide according to the invention comprises an amino acid sequence substantially corresponding to the amino acid sequence of such fragment and is processed to produce such fragment, i.e., an MHC class I and/or class II presented peptide derived from an antigen.

If an antigen peptide is to be presented directly, i.e., without processing, in particular without cleavage, it has a length which is suitable for binding to an MHC molecule, in particular a class I MHC molecule, and preferably is 7-20 amino acids in length, more preferably 7-12 amino acids in length, more preferably 8-11 amino acids in length, in particular 9 or 10 amino acids in length. Preferably the sequence of an antigen peptide which is to be presented directly is derived from the amino acid sequence of an antigen, i.e., its sequence substantially corresponds and is preferably completely identical to a fragment of an antigen.

If an antigen peptide is to be presented following processing, in particular following cleavage, the peptide produced by processing has a length which is suitable for binding to an MHC molecule, in particular a class I MHC molecule, and preferably is 7-20 amino acids in length, more preferably 7-12 amino acids in length, more preferably 8-11 amino acids in length, in particular 9 or 10 amino acids in length. Preferably, the sequence of the peptide which is to be presented following processing is derived from the amino acid sequence of an antigen, i.e., its sequence substantially corresponds and is preferably completely identical to a fragment of an antigen. Thus, an antigen peptide according to the invention in one embodiment comprises a sequence of 7-20 amino acids in length, more preferably 7-12 amino acids in length, more preferably 8-11 amino acids in length, in particular 9 or 10 amino acids in length which substantially corresponds and is preferably completely identical to a fragment of an antigen and following processing of the antigen peptide makes up the presented peptide. However, the antigen peptide may also comprise a sequence which substantially corresponds and preferably is completely identical to a fragment of an antigen which is even longer than the above stated sequence. In one embodiment, an antigen peptide may comprise the entire sequence of an antigen.

Peptides having amino acid sequences substantially corresponding to a sequence of a peptide which is presented by the class I MHC may differ at one or more residues that are not essential for TCR recognition of the peptide as presented by the class I MHC, or for peptide binding to MHC. Such substantially corresponding peptides are also capable of stimulating an antigen-responsive CTL. Peptides having amino acid sequences differing from a presented peptide at residues that do not affect TCR recognition but improve the stability of binding to MHC may improve the immunogenicity of the antigen peptide, and may be referred to herein as "optimized peptide". Using existing knowledge about which of these residues may be more likely to affect binding either to the MHC or to the TCR, a rational approach to the design of substantially corresponding peptides may be employed. Resulting peptides that are functional are contemplated as antigen peptides.

"Antigen processing" refers to the degradation of an antigen into fragments (e.g., the degradation of a protein into peptides) and the association of one or more of these fragments (e.g., via binding) with MHC molecules for presentation by "antigen presenting cells" to specific T-cells.

By "antigen-responsive CTL" is meant a $CD8^+$ T-cell that is responsive to an antigen or a peptide derived from said antigen, which is presented with class I MHC on the surface of antigen presenting cells.

According to the invention, CTL responsiveness may include sustained calcium flux, cell division, production of cytokines such as IFN-γ and TNF-α, up-regulation of activation markers such as CD44 and CD69, and specific cytolytic killing of tumor antigen expressing target cells. CTL responsiveness may also be determined using an artificial reporter that accurately indicates CTL responsiveness.

The term "inducing an immune response" in the context of the present invention preferably refers to induction of cellular as well as humoral immune response. The immune response may be protective/preventive/prophylactic and/or therapeutic. The immune response may be directed against any immunogen or antigen or antigen peptide, preferably against a cancer-associated antigen or a pathogen-associated antigen. "Inducing" in this context may mean that there was no immune response against a particular antigen or pathogen before induction, but it may also mean that there was a certain level of immune response against a particular antigen or pathogen before induction and after induction said immune response is enhanced. Thus, "inducing the immune response" in this context also includes "enhancing the immune response". Preferably, after inducing an immune response in an individual, said individual is protected from developing a disease such as an infectious disease or a cancerous disease or the disease condition is ameliorated by inducing an immune response.

A "cellular immune response" or a "cellular response against an antigen" is meant to include a cellular response directed to cells characterized by presentation of an antigen with class I or class II MHC. The cellular response relates to cells called T-cells or T-lymphocytes which act as either 'helpers' or 'killers'. The helper T cells (also termed CD4+ T cells) play a central role by regulating the immune response and the killer cells (also termed cytotoxic T-cells, cytolytic T-cells, CD8+ T-cells or CTLs) kill diseased cells such as tumor cells, preventing the production of more diseased cells.

The terms "vaccination" and "immunization" relate to the procedure of administering one or more immunogen(s) or antigen(s) or derivatives thereof, in particular in the form of RNA coding therefor, as described herein to an individual and stimulating an immune response against said one or more immunogen(s) or antigen(s) or cells characterized by presentation of said one or more immunogen(s) or antigen(s). The term "immune reaction" is used herein in its conventional meaning and comprises humoral and cellular immunity. An immune reaction comprises one or more reactions selected from the group consisting of developing antibodies against one or more antigens and expansion of antigen-specific T-lymphocytes, preferably CD4+ and CD8+ T-lymphocytes, more preferably CD8+ T-lymphocytes, which may be detected in various proliferation or cytokine production tests in vitro.

By "cell characterized by presentation of an antigen" or "cell presenting an antigen" or "MHC molecules which present an antigen on the surface of an antigen presenting cell" or similar expressions is meant a cell such as a diseased cell, in particular a tumor cell, or an antigen presenting cell presenting the antigen or an antigen peptide, either directly or following processing, in the context of MHC molecules, preferably MHC class I and/or MHC class II molecules, most preferably MHC class I molecules.

The term "immunotherapy" relates to a treatment involving activation of a specific immune reaction. In the context of the present invention, terms such as "protect", "prevent", "prophylactic", "preventive", or "protective" relate to the prevention or treatment or both of the occurrence and/or the propagation of a tumor or a pathogen in an individual. A prophylactic administration of a vaccine composition can protect the recipient from the development of tumor growth or from an infection by a pathogen. A therapeutic administration of a vaccine composition or immunotherapy may protect the individual, for example, from the dissemination or metastasis of existing tumors.

The term "adjuvant" relates to compounds which when administered in combination with an antigen or antigen peptide to an individual prolongs or enhances or accelerates the immune response. In the context of the present invention, RNA may be administered with any adjuvants. It is assumed that adjuvants exert their biological activity by one or more mechanisms, including an increase of the surface of the antigen, a prolongation of the retention of the antigen in the body, a retardation of the antigen release, targeting of the antigen to macrophages, increase of the uptake of the antigen, enhancement of antigen processing, stimulation of cytokine release, stimulation and activation of immune cells such as B-cells, macrophages, dendritic cells, T-cells and unspecific activation of immune cells. Adjuvants comprise a heterogeneous group of compounds such as oil emulsions (e.g., Freund's adjuvants), mineral compounds (such as alum), bacterial products (such as *Bordetella pertussis* toxin), liposomes and immune-stimulating complexes. Examples for adjuvants are monophosphoryl-lipid-A (MPL SmithKline Beecham). Saponins such as QS21 (SmithKline Beecham), DQS21 (SmithKline Beecham; WO 96/33739), QS7, QS17, QS18, and QS-L1 (So et al., 1997, Mol. Cells. 7: 178-186), incomplete Freund's adjuvants, complete Freund's adjuvants, vitamin E, montanid, alum, CpG oligonucleotides (Krieg et al., 1995, Nature 374: 546-549), and various water-in-oil emulsions which are prepared from biologically degradable oils such as squalene and/or tocopherol.

Terms such as "increasing", "enhancing", or "prolonging" preferably relate to an increase, enhancement, or prolongation by about at least 10%, preferably at least 20%, preferably at least 30%, more preferably at least 40%, more preferably at least 50%, even more preferably at least 80%, and most preferably at least 100%. These terms may also relate to circumstances, wherein at time zero there is no detectable signal for a certain compound or condition and at a particular time point later than time zero there is a detectable signal for a certain compound or condition.

"Antigen presenting cells" (APC) are cells which present peptide fragments of protein antigens in association with MHC molecules on their cell surface. Some APCs may activate antigen-specific T-cells. APCs can be divided into professional and unprofessional APCs. For example, professional APCs comprise dendritic cells, macrophages, monocytes, B-cells, microglia etc. In the context of the present invention, the APCs are preferably professional antigen presenting cells. In the context of the present invention, the APCs are preferably immature. Thus, in the context of the present invention, APCs are preferably selected from the group consisting of immature dendritic cells, immature macrophages, immature monocytes, immature microglia, and immature B cells, and are preferably immature dendritic cells. Subsets of immature dendritic cells (iDC) or mature dendritic cells (mDC) comprise, e.g., myeloid dendritic cells (my-DC), plasmacytoid dendritic cells (pDC), monocyte-derived dendritic cells (mo-DC) and hematopoietic progenitor cell-derived dendritic cells (hp-DC). In a preferred embodiment, the APCs according to the present invention are mammalian, preferably human, mouse, or rat.

Dendritic cells comprise a heterogeneous cell population having a specific morphology and a broadly spread tissue distribution. Steinman (1991, Annu. Rev. Immunol. 9: 271-296) provides a review on the dendritic cell system and its role in the immune system. Dendritic cells exhibit the capability to sensitize MHC restricted T-cells and are very effective in presenting antigens to T-cells. The terms "dendritic cells" or "DC" relate to members of a diverse population of morphologically similar cell types, which are located in lymphoid or non-lymphoid tissues. Dendritic cells are e.g. derived from hematopoietic bone marrow progenitor cells. These progenitor cells initially transform into immature dendritic cells. Immature dendritic cells can be found in the peripheral blood and cord blood and in the lymphatic system such as the thymus and lymph nodes. These cells are characterized by high endocytic activity and low T-cell activation potential. Immature dendritic cells constantly sample the surrounding environment for pathogens such as viruses and bacteria. This is done through both receptor-mediated mechanisms and receptor-independent mechanisms (e.g. macropinocytosis). Pattern recognition receptors (PRRs) such as the toll-like receptors (TLRs) recognize specific chemical signatures found on subsets of pathogens. Immature dendritic cells may also phagocytose small quantities of membrane from live own cells, in a process called nibbling. Once they have come into contact with a presentable antigen, they become activated into mature dendritic cells. Immature dendritic cells phagocytose pathogens and degrade their proteins into small pieces and upon maturation present those fragments at their cell surface using MHC molecules. Simultaneously, they up-regulate cell surface receptors that act as co-receptors in T-cell activation such as CD80 (B7.1), CD86 (B7.2), and CD40, greatly enhancing the ability to activate T-cells. They also up-regulate CCR7, a chemotactic receptor that induces the dendritic cell to travel through the blood stream to the spleen or through the lymphatic system to a lymph node. Here they act as antigen-presenting cells: they activate helper T-cells and killer T-cells as well as B-cells by presenting them with antigens derived from the pathogen, alongside non-antigen-specific co-stimulatory signals. Dendritic cells are the most potent of all the antigen presenting cells and are capable of activating both memory and naïve T-cells. It has been shown that activated, mature dendritic cells provide the signals required for T-cell activation and proliferation. These signals can be categorized into two types. The first type, which gives specificity to the immune response, is mediated through interaction between the T-cell receptor/CD3 ("TCR/CD3") complex and an antigenic peptide presented by a major histocompatibility complex ("MHC") class I or II protein on the surface of APCs. The second type of signal, called a co-stimulatory signal, is neither antigen-specific nor MHC-restricted, and can lead to a full proliferation response of T-cells and induction of T-cell effector functions in the presence of the first type of signals. This two-fold signaling can, therefore, result in a vigorous immune response. The different lineages and degrees of maturation of dendritic cells may be distinguished by their particular morphology, phagocytotic/endocytotic capability, and their degree of MHC class II surface expression and the capability to present antigens to T-cells, in particular to naïve T-cells. Typical markers for immature dendritic cells are: MHC II is detectable, CD86 is detectable, and in particular CD83 is negative.

Typically, to generate immature dendritic cells, one must first purify or enrich the monocytic precursors from other contaminating cell types present in blood. This is commonly done through adherence of the monocytic precursors to a plastic (polystyrene) surface, as the monocytes have a greater tendency to stick to plastic than other cells found in, for example, peripheral blood, such as lymphocytes and natural killer (NK) cells. After substantially removing the contaminating cells by vigorous washing, the monocytes are cultured with cytokines that convert the monocytic precursors to immature dendritic cells. Methods for differentiating the monocytic precursor cells to immature dendritic cells were first described by Sallusto and Lanzavecchia (J. Exp. Med., 179:1109-1118, 1994, incorporated herein by reference), who used the cytokines GM-CSF and IL-4 to induce the differentiation of the monocytes to immature dendritic cells. While this combination of cytokines is most typically used, various other combinations have been described to accomplish the same goals, such as replacing IL-4 with IL-13 or IL-15. The end result of this process is a "veiled" cell, which expresses T-cell costimulatory molecules, as well as detectable levels of molecules of the major histocompatibility complex (MHC), but does not express the dendritic cell maturation marker CD83. These cells are similar to Langerhans cells in the skin, and their prime physiological function is to capture invading microorganisms. Variations on this method include different methods of purifying monocytes, including, for example, tangential flow filtration (TFF), or by binding antibodies attached to beads to surface molecules on the monocytes. The beads with the bound cells are then concentrated in a column, or on a magnetic surface, such that contaminating cells can be washed away, after which the monocytes are eluted off the beads. In yet another method to obtain dendritic cells precursors, cells expressing the stem cell marker CD34, either from blood (U.S. Pat. No. 5,994,126, incorporated herein by reference) or from the bone marrow are purified. These cells can be cultured with the essential cytokine GM-CSF to differentiate into immature dendritic cells. These dendritic cells apparently have very similar characteristics and functional properties as immature dendritic cells generated from monocytes. Immature dendritic cells have a high capacity for taking up and processing antigen, but have a limited ability to initiate immune responses. The ability to initiate an immune response is acquired by maturation of the immature dendritic cells. This maturation is also referred to as activating, or activation of, the dendritic cells. The maturation process is initiated through contact with maturation-inducing cytokines, bacterial products or viral components, and the like.

Preferably, immature dendritic cells are monocyte derived immature dendritic cells which can be generated in vitro from peripheral blood mononuclear cells (PBMCs). Immature dendritic cells may be differentiated from PBMCs in the presence of cytokines-such as granulocyte-macrophage colony stimulating factor (GM-CSF) and interleukin (IL-4) in the absence of a maturation agent such as lipopolysaccharide or tumor necrosis factor-$\alpha$ (TNF-$\alpha$). In one embodiment, the immature dendritic cell is a monocyte derived immature dendritic cell obtained or obtainable by culturing peripheral blood monocytes in the presence of one or more cytokines such as GM-CSF and/or IL-4—for at least about 3 days or at least about 7 days. For example, plating of PBMCs in a tissue culture flask permits adherence of monocytes. Treatment of these monocytes with IL-4 and GM-CSF leads to differentiation into immature dendritic cells in about a week. Subsequent treatment with TNF-$\alpha$ further differentiates the immature dendritic cells into mature dendritic cells. In the context of the present invention, the immature dendritic cells may be differentiated from hematopoietic stem cells ($CD34^+$ cells) or they may be purified from an individual using leukapheresis.

Mature dendritic cells can be identified by their change in morphology, by their non-adherence, and by the presence of one or more markers. Such markers include, but are not limited to, cell surface markers such as CD83, CD86, CD40, CD80, and MHC class II. Typical markers for mature dendritic cells (mDC) are: CD83 is detectable and levels of MHC II as well as CD86 are increased compared to immature dendritic cells (iDC). Alternatively, maturation can be identified by observing or measuring the production of cytokines, such as proinflammatory cytokines. Mature dendritic cells can be collected and analyzed using typical cytofluorography and cell sorting techniques and devices, such as a fluorescence activated cell sorter (FACS). Antibodies specific to cell surface antigens of mature dendritic cells are commercially available.

The term "MHC binding peptide" relates to a peptide which binds to an MHC class I and/or an MHC class II molecule. In the case of class I MHC/peptide complexes, the binding peptides are typically 8-10 amino acids long although longer or shorter peptides may be effective. In the case of class II MHC/peptide complexes, the binding peptides are typically 10-25 amino acids long and are in particular 13-18 amino acids long, whereas longer and shorter peptides may be effective. The term "mature histocompatibility complex" and the abbreviation "MHC" include MHC class I and MHC class II molecules and relate to a complex of genes which occurs in all vertebrates. MHC proteins or molecules are important for signaling between lymphocytes and antigen presenting cells in normal immune reactions, wherein the MHC proteins or molecules bind peptides and present them for recognition by T-cell receptors.

The term "immune effector cells" in the context of the present invention relates to cells which exert effector functions during an immune reaction. "Immune effector cells" preferably are capable of binding an antigen or a cell characterized by presentation of an antigen and mediating an immune response. For example, such cells secrete cytokines and/or chemokines, kill microbes, secrete antibodies, recognize infected or cancerous cells, and optionally eliminate such cells. For example, immune effector cells comprise T-cells (cytotoxic T-cells, helper T-cells, tumor infiltrating T-cells), B-cells, natural killer cells, neutrophils, macrophages, and dendritic cells. Preferably, in the context of the present invention, "immune effector cells" are T-cells, preferably $CD4^+$ and/or $CD8^+$ cells.

Preferably, an "immune effector cell" recognizes an antigen or an antigen peptide derived from said antigen with some degree of specificity, in particular if presented in the context of MHC molecules such as on the surface of antigen presenting cells or diseased cells such as tumor cells. Preferably, said recognition enables the cell that recognizes an antigen or an antigen peptide derived from said antigen to be responsive. If the cell is a helper T-cell ($CD4^+$ T-cell) bearing receptors that recognize an antigen or an antigen peptide derived from said antigen in the context of MHC class II molecules such responsiveness may involve the release of cytokines and/or the activation of $CD8^+$ lymphocytes (CTLs) and/or B-cells. If the cell is a CTL such responsiveness may involve the elimination of cells presented in the context of MHC class I molecules, i.e., cells characterized by presentation of an antigen with class I MHC, for example, via apoptosis or perforin-mediated cell lysis. Such CTL that recognizes an antigen or an antigen peptide derived from said antigen and are responsive are also termed "antigen-responsive CTL" herein. If the cell is a B-cell such responsiveness may involve the release of immunoglobulins.

The term "half-life" relates to the period of time which is needed to eliminate half of the activity, amount, or number of molecules. In the context of the present invention, the half life of an RNA is indicative for the stability of said RNA.

The terms "patient", "individual", or "animal" relate to mammals. For example, mammals in the context of the present invention are humans, non-human primates, domesticated animals such as dogs, cats, sheep, cattle, goats, pigs, horses etc., laboratory animals such as mice, rats, rabbits, guinea pigs, etc. as well as animals in captivity such as animals of zoos. The term "animal" as used herein also includes humans.

According to the invention, the term "tumor" or "tumor disease" refers to a swelling or lesion formed by an abnormal growth of cells (called neoplastic cells or tumor cells). By "tumor cell" is meant an abnormal cell that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be either benign, pre-malignant, or malignant.

Preferably, a tumor disease according to the invention is a cancer disease, i.e., a malignant disease, and a tumor cell is a cancer cell. Preferably, a tumor disease is characterized by cells in which an antigen, i.e., a tumor antigen, is expressed or abnormally expressed. Preferably, a tumor disease or a tumor cell is characterized by presentation of a tumor antigen with class I MHC.

"Abnormal expression" means according to the invention that expression is altered, preferably increased, compared to the state in a healthy individual. An increase in expression refers to an increase by at least 10%, in particular at least 20%, at least 50% or at least 100%. In one embodiment, expression is only found in a diseases tissue, while expression in a healthy tissue is repressed.

Preferably, a tumor disease according to the invention is cancer, wherein the term "cancer" according to the invention comprises leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer and the metastases thereof. Examples thereof are lung carcinomas, mamma carcinomas, prostate carcinomas, colon carcinomas, renal cell carcinomas, cervical carcinomas, or metastases of the cancer types or tumors described above. The term "cancer" according to the invention also comprises cancer metastases.

The compositions according to the present invention are generally applied in "pharmaceutically acceptable amounts" and in "pharmaceutically acceptable preparations". Such compositions may contain salts, buffers, preserving agents, carriers and optionally other therapeutic agents. "Pharmaceutically acceptable salts" comprise, for example, acid addition salts which may, for example, be formed by mixing a solution of compounds with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compound carries an acidic moiety, suitable pharmaceutically acceptable salts thereof may include alkali metal salts (e.g., sodium or potassium salts); alkaline earth metal salts (e.g., calcium or magnesium salts); and salts formed with suitable organic ligands (e.g., ammonium, quaternary ammonium and amine cations formed using counteranions such as halide, hydroxide, carboxylate, sulfate, phosphate, nitrate, alkyl sulfonate and aryl sulfonate). Illustrative examples of pharmaceutically acceptable salts include, but are not limited to, acetate, adipate, alginate, ascorbate, aspartate, benzenesulfonate, benzoate, bicarbonate, bisulfate, bitartrate, borate, bromide, butyrate, calcium edetate, camphorate, camphorsulfonate, camsylate, carbonate, chloride, citrate, clavulanate, cyclopentanepropionate, digluconate, dihydrochloride, dodecylsulfate, edetate, edisylate, estolate, esylate, ethanesulfonate, formate, fumarate, gluceptate, glucoheptonate, gluconate, glutamate, glycerophosphate, glycolylarsanilate, hemisulfate, heptanoate, hexanoate, hexylresorcinate, hydrabamine, hydrobromide, hydrochloride, hydroiodide, 2-hydroxy-ethanesulfonate, hydroxynaphthoate, iodide, isothionate, lactate, lactobionate, laurate, lauryl sulfate, malate, maleate, malonate, mandelate, mesylate, methanesulfonate, methylsulfate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, 3-phenylpropionate, phosphate/diphosphate, picrate, pivalate, polygalacturonate, propionate, salicylate, stearate, sulfate, subacetate, succinate, tannate, tartrate, teoclate, tosylate, triethiodide, undecanoate, valerate, and the like (see, for example, S. M. Berge et al., "Pharmaceutical Salts", J. Pharm. Sci., 66, pp. 1-19 (1977)).

The term "excipient" when used herein is intended to indicate all substances in a pharmaceutical formulation which are not active ingredients such as, e.g., carriers, binders, lubricants, thickeners, surface active agents, preservatives, emulsifiers, buffers, flavoring agents, or colorants.

The compositions according to the present invention may comprise a pharmaceutically acceptable carrier. The term "pharmaceutically acceptable carrier" in the context of the present invention relates to one or more compatible solid or liquid fillers or diluents, which are suitable for an administration to a human. The term "carrier" relates to a natural or synthetic organic or inorganic component which is combined with an active component in order to facilitate the application of the active component. Preferably, carrier components are sterile liquids such as water or oils, including those which are derived from mineral oil, animals or plants, such as peanut oil, soy bean oil, sesame oil, sunflower oil, etc. Salt solutions and aqueous dextrose and glycerin solutions may also be used as aqueous carrier compounds.

According to the present invention, the compositions are administered in a therapeutically effective amount. A "therapeutically effective amount" relates to an amount which—alone or in combination with further dosages—results in a desired reaction or a desired effect. In the case of the therapy of a particular disease or a particular condition, the desired reaction relates to the inhibition of the progress of the disease. This comprises the deceleration of the progress of the disease, in particular a disruption of the progression of the disease. The desired reaction for a therapy of a disease or a condition may also be the retardation of the occurrence or the inhibition of the occurrence of the disease or the condition. An effective amount of the composition according to the present invention is dependent on the condition or disease, the severity of the disease, the individual parameters of the patient, including age, physiological condition, height and weight, the duration of the treatment, the type of an optionally accompanying therapy, the specific administration route, and similar factors. In case the reaction of a patient is insufficient with an initial dosage, higher dosages (or higher effective dosages which may be achieved by a more localized administration route) may be applied. In general, for a treatment or for an induction or increase of an immune reaction in a human preferably dosages of the RNA in the range of 1 ng to 700 µg, 1 ng to 500 µg, 1 ng to 300 µg, 1 ng to 200 µg, or 1 ng to 100 µg are formulated and administered.

In the context of the present invention, the term "transcription" relates to a process, wherein the genetic code in a DNA sequence is transcribed into RNA. Subsequently, the RNA may be translated into protein. According to the present invention, the term "transcription" comprises "in vitro transcription", wherein the term "in vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are according to the present invention encompassed by the term "vector". According to the present invention, the RNA used in the present invention may be obtained by in vitro transcription of an appropriate DNA template. The promoter for controlling transcription can be any promoter for any RNA polymerase. Particular examples of RNA polymerases are the T7, T3, and SP6 RNA polymerases. Preferably, the in vitro transcription according to the invention is controlled by a T7 or SP6 promoter. A DNA template for in vitro transcription may be obtained by cloning of a nucleic acid, in particular cDNA, and introducing it into an appropriate vector for in vitro transcription. The cDNA may be obtained by reverse transcription of RNA.

The term "expression" is used herein in its broadest meaning and comprises the production of RNA or of RNA and protein. With respect to RNA, the term "expression" or "translation" relates in particular to the production of peptides or proteins. Expression may be transient or may be stable.

The term "translation" in the context of the present invention relates to a process at the ribosome, wherein an mRNA strand controls the assembly of an amino acid sequence to generate a protein or a peptide.

According to the invention, RNA is to be transferred into immature antigen presenting cells either in vitro or in vivo, e.g., by administration of RNA into the lymphatic system, preferably into the lymph nodes. In this respect, terms such as "transferring" or "transfecting" are used interchangeably herein and relate to the introduction of nucleic acids, in particular exogenous or heterologous nucleic acids, in particular RNA into a cell. According to the present invention, any technique which is suitable to transfer RNA into cells may be used to introduce RNA into cells. Preferably, the RNA is transfected into cells by standard techniques. Such techniques comprise transfection of nucleic acid calcium phosphate precipitates, transfection of nucleic acids which are associated with DEAE, the transfection or infection with viruses which carry the nucleic acids of interest, electroporation, lipofection, and microinjection. According to the present invention, the administration of a nucleic acid is either achieved as naked nucleic acid or in combination with an administration reagent. Preferably, administration of nucleic acids is in the form of naked nucleic acids. Preferably, the RNA is administered in combination with stabilizing substances such as RNase inhibitors. In a particularly preferred embodiment, the RNA and/or the compositions of the present invention are administered as naked RNA preferably by intranodal injection. According to the present invention, a conventional transfection technique is not absolutely necessary to introduce naked RNA into cells, preferably antigen-presenting cells, preferably immature antigen-presenting cells, preferably immature dendritic cells, since in particular immature antigen-presenting cells such as immature dendritic cells are capable of taking up naked RNA by macropinocytosis. Preferably, the introduction of RNA which encodes an antigen or antigen peptide into a cell results in expression of said antigen or antigen peptide in the cell. In particular embodiments, the targeting of the nucleic acids to particular cells is preferred. In such embodiments, a carrier which is applied for the administration of the nucleic acid to a cell (for example, a retrovirus or a liposome), exhibits a targeting molecule. For example, a molecule such as an antibody which is specific for a surface membrane protein on the target cell or a ligand for a receptor on the target cell may be incorporated into the nucleic acid carrier or may be bound thereto. In case the nucleic acid is administered by liposomes, proteins which bind to a surface membrane protein which is associated with endocytosis may be incorporated into the liposome formulation in order to enable targeting and/or uptake. Such proteins encompass capsid proteins of fragments thereof which are specific for a particular cell type, antibodies against proteins which are internalized, proteins which target an intracellular location etc.

According to the present invention, the term "peptide" comprises oligo- and polypeptides and refers to substances comprising two or more, preferably three or more, preferably four or more, preferably six or more, preferably eight or more, preferably ten or more, preferably 14 or more, preferably 16 or more, preferably 21 or more and up to preferably 8, 10, 20, 30, 40, or 50, in particular 100 amino acids joint covalently by peptide bonds. The term "protein" refers to large peptides, preferably to peptides with more than 100 amino acid residues, but in general the terms "peptides" and "proteins" are synonymous and are used interchangeably herein.

The term "portion of MHC molecules which present an antigen of interest" refers to the fraction of MHC molecules on the surface of an antigen presenting cell which are loaded with, i.e., are bound to, a particular antigen or an antigen peptide derived from said antigen relative to the total amount of MHC molecules on the surface of the cell. In a preferred embodiment, the RNA used in the present invention is capable of increasing the portion of MHC molecules which present an antigen of interest on the surface of an antigen presenting cell into which the RNA was transferred. This is in comparison to an RNA which does not carry the 5'-cap having a structure according to formula (I), in particular, an RNA which carries a conventional RNA cap.

The term "alkyl" refers to a saturated straight or branched carbon chain. Preferably, the chain comprises from 1 to 10 carbon atoms, i.e., 1, 2, 3, 4, 5, 6, 7, 8, 9, or 10 carbon atoms, preferably 1 to 4 carbon atoms, e.g., methyl, ethyl, propyl, iso-propyl, butyl, iso-butyl, tert-butyl, n-pentyl, iso-pentyl, sec-pentyl, neo-pentyl, 1,2-dimethyl-propyl, iso-amyl, n-hexyl, iso-hexyl, sec-hexyl, n-heptyl, iso-heptyl, n-octyl, 2-ethyl-hexyl, n-nonyl, and n-decyl. Alkyl groups are optionally substituted.

The term "cycloalkyl" on its own or in combination with other terms, represents, unless otherwise stated, cyclic versions of "alkyl" with preferably 3 to 10 carbon atoms, i.e., 3, 4, 5, 6, 7, 8, 9, or 10 carbon atoms, preferably 3 to 6 carbon atoms, forming a ring, preferably cyclopropyl, cyclobutyl, cyclopentyl, cyclohexyl, cycloheptyl, cyclooctyl, cyclononyl, or cylcodecyl. The term "cycloalkyl" is also meant to include bicyclic versions thereof. If bicyclic rings are formed it is preferred that the respective rings are connected to each other at two adjacent carbon atoms, however, alternatively the two rings are connected via the same carbon atom, i.e., they form a spiro ring system or they form "bridged" ring systems. Preferred examples of cycloalkyl include $C_3$-$C_8$-cycloalkyl, in particular cyclopropyl, cyclobutyl, cyclopentyl, cyclohexyl, cycloheptyl, cyclooctyl, spiro[3,3]heptyl, spiro[3,4]octyl, spiro[4,3]octyl, bicyclo[4.1.0]heptyl, bicyclo[3.2.0]heptyl, bicyclo[2.2.1]heptyl, bicyclo[2.2.2]octyl, bicyclo[5.1.0]octyl, and bicyclo[4.2.0]octyl.

The term "alkenyl" in the context of the present invention refers to an olefinic unsaturated straight or branched carbon chain with one or more double bonds. Preferably, the chain comprises from 2 to 10 carbon atoms, i.e., 2, 3, 4, 5, 6, 7, 8, 9, or 10 carbon atoms, preferably 2 to 4 carbon atoms. For example, an alkenyl may be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, or 9-decenyl.

The term "alkenyl" in the context of the present invention also includes "cycloalkenyl" which refers to an olefinic unsaturated group containing one or more ring(s) with one or more double bonds. Preferably the cycloalkenyl ring comprises from 3 to 10 carbon atoms, i.e., 3, 4, 5, 6, 7, 8, 9, or 10, e.g., cyclopropenyl, cyclobutenyl, cyclopentenyl, cyclohexenyl, cycloheptenyl, cyclooctenyl, spiro[3,3]heptenyl, spiro[3,4]octenyl, spiro[4,3]octenyl, bicyclo[4.1.0]heptenyl, bicyclo[3.2.0]heptenyl, bicyclo[2.2.1]heptenyl, bicyclo[2.2.2]octenyl, bicyclo[5.1.0]octenyl, or bicyclo[4.2.0]octenyl.

The term "alkynyl" in the context of the present invention refers to an unsaturated straight or branched carbon chain with one or more triple bonds. Preferably, the chain comprises from 2 to 10 carbon atoms, i.e., 2, 3, 4, 5, 6, 7, 8, 9, or 10 carbon atoms, preferably 2 to 4 carbon atoms. Examples for alkynyl are ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 2-heptynyl, 3-heptynyl, 4-heptynyl, 5-heptynyl, 6-heptynyl, 1-octynyl, 2-octynyl, 3-octynyl, 4-octynyl, 5-octynyl, 6-octynyl, 7-octynyl, 1-nonylyl, 2-nonynyl, 3-nonynyl, 4-nonynyl, 5-nonynyl, 6-nonynyl, 7-nonynyl, 8-nonynyl, 1-decynyl, 2-decynyl, 3-decynyl, 4-decynyl, 5-decynyl, 6-decynyl, 7-decynyl, 8-decynyl, or 9-decynyl.

The term "heterocyclyl" means a cycloalkyl group as defined above in which from 1 to 3 carbon atoms in the ring are replaced by heteroatoms of O, S, or N.

The term "aryl" preferably refers to an aromatic ring structure containing 5 to 14 carbon atoms, for example, phenyl, indenyl, 1-naphthyl, 2-naphthyl, 1-anthryl, 2-anthryl, 9-anthryl, 1-phenanthryl, 2-phenanthryl, 3-phenanthryl, 4-phenanthryl, and 9-phenanthryl. Preferably, "aryl" refers to a monocyclic ring containing 6 carbon atoms or an aromatic bicyclic ring system containing 10 carbon atoms. Preferred examples are phenyl or naphthyl. The aryl group is optionally substituted.

The term "heteroaryl" means an aryl group as defined above in which from 1 to 3 carbon atoms in the ring are replaced by heteroatoms of O, S, or N. Preferably the term refers to a five or six-membered aromatic monocyclic ring wherein 1 to 3 carbon atoms are replaced by the same or different heteroatoms of O, N, or S. Alternatively, it means an aromatic bicyclic ring system wherein 1 to 3 carbon atoms are replaced with the same or different heteroatoms of O, N, or S. Preferred examples are furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl.

The term "halo" in the context of the present invention means fluoro, chloro, bromo, or iodo, preferably fluoro.

The term "alkoxy" refers to the group —OR, where R is alkyl, aryl or cycloalkyl and may include methoxy, ethoxy, propoxy, butoxy, iso-butoxy, sec-butoxy, pentoxy, hexyloxy, heptyloxy, octyloxy, nonyloxy, or decyloxy.

The term "optionally substituted" indicates that one or more hydrogen atom(s) is/are replaced with a group different from hydrogen such as halogen, alkyl, cycloalkyl, haloalkyl, amino, alkylamino, hydroxy, alkoxy, haloalkoxy, aryl, and heterorayl and the like. The optional substituents may themselves be substituted by substituents such as halogen, in particular fluoro.

The term "hydroxy" refers to the group —OH.

The term "haloalkyl" refers to an alkyl or cycloalkyl group substituted with one or more halogen (e.g., trifluoromethyl).

The term "haloalkoxy" refers to the group —OR, where R is alkyl, aryl, or cycloalkyl substituted with one or more halogen.

The term amino refers to the group —NH$_2$.

The term "alkylamino" refers to the group —NR'R where R is hydrogen, alkyl, aryl, or cycloalkyl and where R' is alkyl, aryl, or cycloalkyl.

The term "acylamino" refers to the group —NRC(O)R where each R is independently hydrogen, alkyl, aryl, or heteroaryl.

The term "carbonyl" refers to the group C=O wherein the carbon can be part of an alkyl chain or ring system.

The phrase "the stereochemical configuration at the P atom comprising the substituent $R^5$ corresponds to that at the $P_\beta$ atom of the D1 diastereomer of beta-S-ARCA" means that a phosphorous atom comprising the substituent $R^5$ and having a chiral center, and therefore capable of existing in either of two stereochemical configurations, is present in predominately one desired stereochemical configuration, i.e., that at the $P_\beta$ atom of the D1 diastereomer of beta-S-ARCA. As the case may be for the $P_\beta$ atom of the D1 diastereomer of beta-S-ARCA this could either be the (R) configuration or the (S) configuration. Preferably, greater than 50 percent of the group of interest has the desired stereochemical configuration, preferably at least 75 percent of the group of interest has the desired stereochemical configuration, more preferably at least 90 percent of the group of interest has the desired stereochemical configuration, even more preferably at least 95 percent of the group of interest has the desired stereochemical configuration, and most preferably at least 99 percent of the group of interest has the desired stereochemical configuration.

The "D1 diastereomer of beta-S-ARCA" or "beta-S-ARCA(D1)" is the diastereomer of beta-S-ARCA which elutes first on an HPLC column compared to the D2 diastereomer of beta-S-ARCA (beta-S-ARCA(D2)) and thus exhibits a shorter retention time. The HPLC preferably is an analytical HPLC. In one embodiment, a Supelcosil LC-18-T RP column, preferably of the format: 5 μm, 4.6×250 mm is used for separation, whereby a flow rate of 1.3 ml/min can be applied. In one embodiment, a gradient of methanol in ammonium acetate, for example, a 0-25% linear gradient of methanol in 0.05 M ammonium acetate, pH=5.9, within 15 min is used. UV-detection (VWD) can be performed at 260 nm and fluorescence detection (FLD) can be performed with excitation at 280 nm and detection at 337 nm.

The present inventors surprisingly found, that RNA which is modified to contain a specific 5'-cap structure, in particular a phosphorothioate 5'-cap structure, which exhibits a particular stereochemical configuration at the P atom which when being part of a phosphorothioate group and not a phosphodiester group decreases susceptibility towards degradation by Dcp2, i.e., the $P_\beta$ atom if n in formula (I) is 1, the $P_\gamma$ atom if n in formula (I) is 2, or the $P_\delta$ atom if n in formula (I) is 3, the particular stereochemical configuration at the P atom corresponding to the stereochemical configuration at the $P_\beta$ atom of the 5'-cap analog beta-S-ARCA(D1), possesses increased stability and thus, also exhibits increased expression, in particular in immature antigen-presenting cells, particularly in immature dendritic cells.

The present invention relates to modification of RNA, preferably mRNA, to increase the stability of said RNA, preferably in immune cells, more preferably in immature immune cells, even more preferably in immature antigen presenting cells, and most preferably in immature dendritic cells. The modified RNA described in the present invention is particularly useful for RNA vaccination.

"RNA which is modified with a 5'-cap structure" means RNA to which a 5'-cap structure is bonded so as to result in a modified RNA wherein a guanosine of the cap structure becomes part of the RNA and a modified guanosine of the cap structure is bonded to the RNA via a 5' to 5' triphosphate linkage or modified triphosphate linkage. Thus, such modified RNA may have, for example, the formula $m_2^{7,2'-O}G$-pp$_s$pGRNA.

The RNA modified with a 5'-cap structure used in the present invention has the following structure:

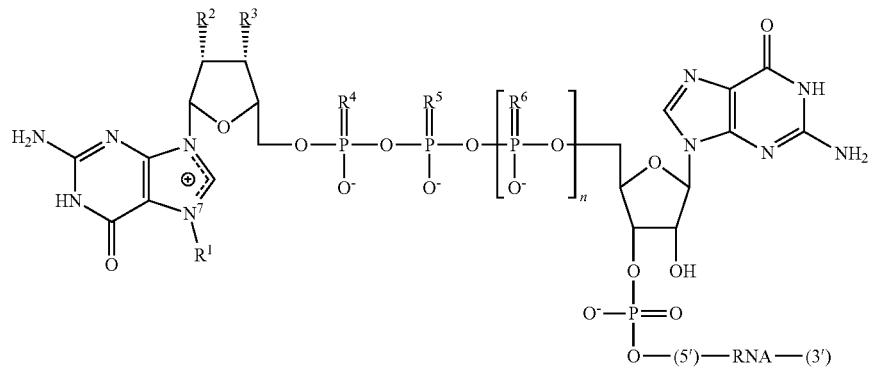

wherein $R^1$ is selected from the group consisting of optionally substituted alkyl, optionally substituted alkenyl, optionally substituted alkynyl, optionally substituted cycloalkyl, optionally substituted heterocyclyl, optionally substituted aryl, and optionally substituted heteroaryl, $R^2$ and $R^3$ are independently selected from the group consisting of H, halo, OH, and optionally substituted alkoxy, or $R^2$ and $R^3$ together form O—X—O, wherein X is selected from the group consisting of optionally substituted $CH_2$, $CH_2CH_2$, $CH_2CH_2CH_2$, $CH_2CH(CH_3)'$ and $C(CH_3)_2$, preferably $R^2$ and $R^3$ together form 2',3'-isopropylidene, or $R^2$ is combined with the valence produced by removal of the hydrogen atom at position 4' of the ring to which $R^2$ is attached, wherein the bridging linkage from $R^2$ to the 4' position is defined as an —O—CH$_2$— group or —CH$_2$—O— group, $R^5$ is selected from the group consisting of S, Se, and BH$_3$, preferably $R^5$ is S, $R^4$ and $R^6$ are independently selected from the group consisting of O, S, Se, and BH$_3$, preferably $R^4$ and $R^6$ are independently selected from O and S, more preferably R4 and R6 are O, n is 1, 2, or 3, preferably n is 1 or 2, more preferably n is 1, wherein the stereochemical configuration at the P atom comprising the substituent $R^5$ corresponds to that at the $P_\beta$ atom of the D1 diastereomer of beta-S-ARCA.

The 5'-cap of the modified RNA used in the present invention has the following structure shown in formula (I):

formula (I)

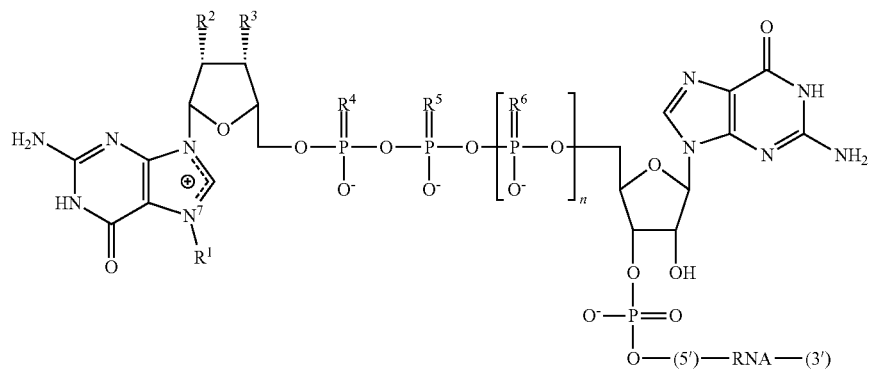

wherein $R^1$ is selected from the group consisting of optionally substituted alkyl, optionally substituted alkenyl, optionally substituted alkynyl, optionally substituted cycloalkyl, optionally substituted heterocyclyl, optionally substituted aryl, and optionally substituted heteroaryl, $R^2$ and $R^3$ are independently selected from the group consisting of H, halo, OH, and optionally substituted alkoxy, or $R^2$ and $R^3$ together form O—X—O, wherein X is selected from the group consisting of optionally substituted $CH_2$, $CH_2CH_2$, $CH_2CH_2CH_2$, $CH_2CH(CH_3)$, and $C(CH_3)_2$, preferably $R^2$ and $R^3$ together form 2',3'-isopropylidene, or $R^2$ is combined with the valence produced by removal of the hydrogen atom at position 4' of the ring to which $R^2$ is attached, wherein the bridging linkage from $R^2$ to the 4' position is defined as an —O—$CH_2$— group or —$CH_2$—O— group, $R^5$ is selected from the group consisting of S, Se, and $BH_3$, preferably $R^5$ is S, $R^4$ and $R^6$ are independently selected from the group consisting of O, S, Se, and $BH_3$, preferably $R^4$ and $R^6$ are independently selected from O and S, more preferably $R^4$ and $R^6$ are O, n is 1, 2, or 3, preferably n is 1 or 2, more preferably n is 1, wherein the stereochemical configuration at the P atom comprising the substituent $R^5$ corresponds to that at the $P_\beta$ atom of the D1 diastereomer of beta-S-ARCA.

The phrase "$R^4$ and $R^6$ are independently selected from the group consisting of O, S, Se, and $BH_3$" is to mean that the substituent $R^6$ at each occurrence is independently selected from the group consisting of O, S, Se, and $BH_3$, and thus, may be the same or different. For example, if n is 2 the structure shown in formula (I) comprises two $R^6$ substituents and each of these two $R^6$ substituents is independently selected from the group consisting of O, S, Se, and $BH_3$ such that the first $R^6$ substituent and the second $R^6$ substituent in the same formula may be the same or may be different.

Preferably, the 5'-cap of the modified RNA used in the present invention upon transfer of the modified RNA into immature antigen presenting cells is capable of increasing the stability of the RNA, increasing translation efficiency of the RNA, prolonging translation of the RNA, increasing total protein expression of the RNA, and/or increasing the immune response against an antigen encoded by said RNA when compared to the same RNA without the 5'-cap structure. It is particularly preferred that the immature antigen presenting cells are immature dendritic cells. The skilled person may readily determine whether the 5'-cap of the modified RNA is capable of exerting the above functions, for example, by generating two RNAs, e.g., by in vitro transcription, which only differ in the 5'-cap, wherein one of the RNA carries a 5'-cap according to formula (I) and the other RNA (reference RNA) (i) does not comprise a 5'-cap, (ii) carries a conventional mRNA 5'-cap, i.e., a methyl-7-guanosine cap, or (iii) carries any other cap with which the function of the 5'-cap according to formula (I) should be compared. For example, the reference RNA may carry a 5'-cap which corresponds to the D2 diastereomer of beta-S-ARCA. It is particularly preferred that the 5'-cap structure of the modified RNA used in the present invention upon transfer of the modified RNA into immature antigen presenting cells is capable of increasing the stability of the RNA, increasing translation efficiency of the RNA, prolonging translation of the RNA, increasing total protein expression of the RNA, and/or increasing the immune response against an antigen encoded by said RNA when compared to the same RNA having a conventional mRNA 5'-cap and/or when compared to the same RNA having the same 5'-cap structure but differing in the stereochemical configuration at the P atom carrying the substituent $R^5$, i.e. which corresponds to that at the $P_\beta$ atom of the D2 diastereomer of beta-S-ARCA, preferably when compared to the same RNA having a 5'-cap which corresponds to the D2 diastereomer of beta-S-ARCA.

Preferably, $R^1$ is selected such that the 5'-cap used in the present invention does not inhibit translation of the RNA carrying said 5'-cap. In particular, $R^1$ is selected such that the RNA, in particular the 5'-cap is recognized by the translation initiation machinery, preferably in vivo and in vitro, preferably the 5'-cap is recognized by the eukaryotic translation initiation machinery. For example, the skilled person may determine whether an RNA or an RNA 5'-cap is recognized by the eukaryotic translation initiation machinery by determining the affinity of the eukaryotic translation initiation factor eIF4E for said RNA or said RNA 5'-cap.

Preferably, $R^1$ is selected from the group consisting of optionally substituted $C_1$-$C_4$ alkyl, e.g., methyl, ethyl, propyl, or butyl, optionally substituted benzyl, optionally substituted phenylethyl, and optionally substituted naphthylmethyl, optionally substituted $C_2$-$C_4$ alkenyl, e.g., ethenyl, propenyl, or butenyl, and optionally substituted aryl. Preferably, $R^1$ is selected from the group consisting of $C_1$-$C_4$ alkyl and optionally substituted aryl. Even more preferably, $R^1$ is selected from the group consisting of methyl, ethyl, optionally substituted benzyl, optionally substituted phenylethyl, and optionally substituted naphthylmethyl. Preferably, $R^1$ is methyl.

Preferably, the configuration of $R^2$ and $R^3$ is such that the 5'-cap can only be incorporated into an RNA chain in one orientation. Pasquinelli et al. (1995, RNA J. 1: 957-967) have demonstrated that during in vitro transcription bacteriophage RNA polymerases use the 7-methylguanosine unit for initiation of transcription whereby around 40-50% of the transcripts with cap possess the cap-dinucleotide in a reverse orientation (i.e., the initial reaction product is Gpppm$^7$GpN). Compared to the RNAs with a correct cap RNAs with a reverse cap are not functional with respect to translation of the encoded proteins. Thus, it is desirable to incorporate the cap in the correct orientation, i.e., resulting in an RNA with a structure essentially corresponding to m$^7$GpppGpN etc. It has been shown that the reverse integration of the cap-dinucleotide is inhibited by the substitution of either the 2'- or the 3'-OH group of the methylated guanosine unit (Stepinski et al., 2001; RNA J. 7:1486-1495; Peng et al., 2002; Org. Lett. 24:161-164). RNAs which are synthesized in presence of such "anti reverse cap analogs", i.e., ARCAs, are translated more efficiently than RNAs which have been in vitro transcribed in presence of the conventional 5'-cap m$^7$GpppG. Furthermore, Kore et al. (J. Am. Chem. Soc. 2009 Apr. 22. [Epub ahead of print]) found that locked nucleic acid (LNA)-modified dinucleotide mRNA cap analogues are also not incorporated in the reverse orientation into an RNA strand (Kore et al. 2009, J. Am. Chem. Soc. 131:6364-6365).

Thus, in a particularly preferred embodiment, $R^1$ is selected such that the eukaryotic translation initiation machinery is capable of recognizing the modified RNA used in the present invention and $R^2$ and/or $R^3$ are selected such that the cap cannot be incorporated in reverse orientation into an RNA strand.

Preferably, $R^2$ and $R^3$ are independently selected from the group consisting of H, F, OH, methoxy, ethoxy, and propoxy. Preferably, one of $R^2$ and $R^3$ is OH, and the other is not OH. More preferably, at least one of $R^2$ and $R^3$ is not OH. It is particularly preferred that when the ring structure comprising the substituents $R^2$ and $R^3$ has the stereochemical configuration of ribose, at least one of $R^2$ and $R^3$ is not OH. Preferably the residue which is not OH is selected from the group consisting of H, halo, and optionally substituted $C_1$-$C_{10}$ alkoxy, preferably is selected from the group consisting of H, F, methoxy, ethoxy, and propoxy, more preferably is methoxy.

In a preferred embodiment, in particular when the ring structure comprising the substituents $R^2$ and $R^3$ has the stereochemical configuration of ribose, $R^2$ is OH and $R^3$ is methoxy or $R^2$ is methoxy and $R^3$ is OH.

In one embodiment, when the stereochemical configuration of the ring structure comprising the substituents $R^2$ and $R^3$ does not correspond to the stereochemical configuration of ribose, for example, corresponds to the stereochemical configuration of arabinose, xylose, or lyxose, in particular when the stereochemical configuration of said ring structure corresponds to that of arabinose, $R^2$ and $R^3$ may both be OH. However, in this embodiment, it is also possible that $R^2$ and $R^3$ are selected as specified above.

In a particular preferred embodiment, $R^5$ is S. Preferably, $R^4$ and $R^6$ are selected from the group consisting of O and S, and are preferably O. Preferably, n is 1 or 2, more preferably n is 1.

Preferred embodiments of the 5'-cap structure according to formula (I) are described below. It is to be understood that all the structures, formulas, and compounds described below are encompassed by the term "5'-cap structure according to formula (I)".

In a most preferred embodiment, the 5'-cap used in the present invention corresponds to the D1 diastereomer of beta-S-ARCA having the following structure according to formula (II):

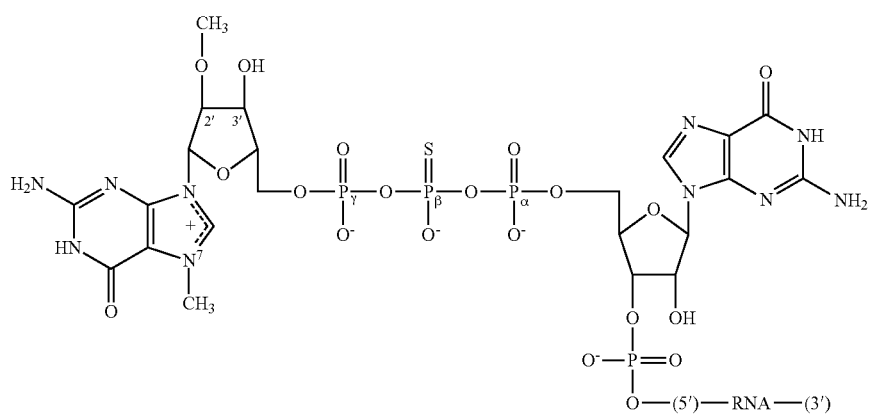

formula (II)

In this context, "corresponding to" means that the 5'-cap is identical to the D1 diastereomer of beta-S-ARCA, or is essentially identical to the D1 diastereomer of beta-S-ARCA, meaning that in a preferred embodiment only minor differences may exist between the 5'-cap of the RNA used in the present invention and the D1 diastereomer of beta-S-ARCA. For example, the substituent at the 2'-position of the 7-methylguanosine unit may be H or ethoxy and/or the substituent at the $N^7$ atom of the 7-methylguanosine unit may be ethyl, and/or the substituent at the 2'-position of the 7-methylguanosine unit may be OH and the substituent at the 3'-position of the 7-methylguanosine may be different from OH, for example, may be H or methoxy, preferably methoxy.

In the following, particularly preferred embodiments of the RNA used in the present invention are disclosed:

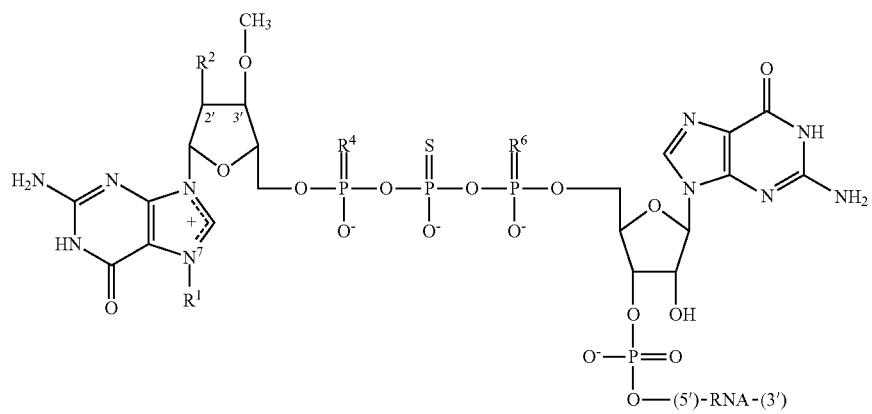

wherein $R^1$ is selected from the group consisting of optionally substituted $C_1$-$C_4$ alkyl, e.g., methyl, ethyl, propyl, butyl, optionally substituted benzyl, optionally substituted phenylethyl, or optionally substituted naphthylmethyl, optionally substituted $C_2$-$C_4$ alkenyl, e.g., ethenyl, propenyl, or butenyl, and optionally substituted aryl, $R^2$ is selected from the group consisting of H, OH, F, methoxy, ethoxy, and propoxy, preferably $R^2$ is OH, or $R^2$ is combined with the valence produced by removal of the hydrogen atom at position 4' of the ring to which $R^2$ is attached, wherein the bridging linkage from $R^2$ to the 4' position is defined as an —O—$CH_2$— group or —$CH_3$—O— group, $R^4$ and $R^6$ are independently selected from the group consisting of O, S, Se, and $BH_3$, preferably $R^4$ and $R^6$ are independently selected from the group consisting of O and S, and most preferably $R^4$ and $R^6$ are O, wherein the stereochemical configuration at the $P_\beta$ atom corresponds to that at the $P_\beta$ atom of the D1 diastereomer of beta-S-ARCA.

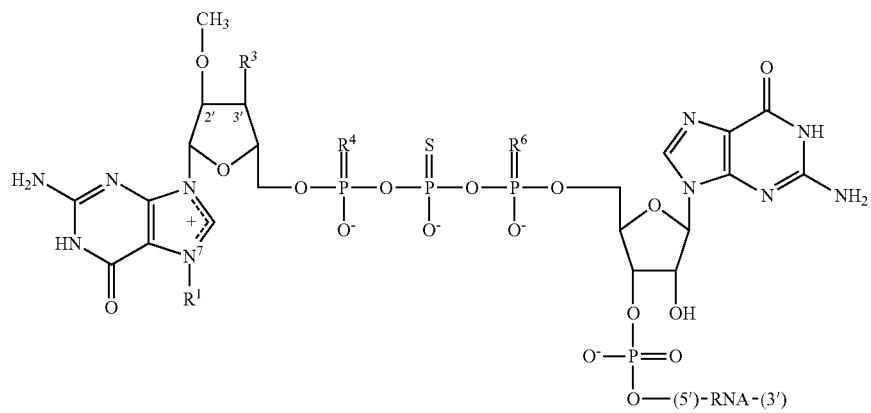

wherein $R^1$ is selected from the group consisting of optionally substituted $C_1$-$C_4$ alkyl, e.g., methyl, ethyl, propyl, butyl, optionally substituted benzyl, optionally substituted phenylethyl, or optionally substituted naphthylmethyl, optionally substituted $C_2$-$C_4$ alkenyl, e.g., ethenyl, propenyl, or butenyl, and optionally substituted aryl, $R^3$ is selected from the group consisting of H, OH, F, methoxy, ethoxy, and propoxy, preferably $R^3$ is OH, $R^4$ and $R^6$ are independently selected from the group consisting of O, S, Se, and $BH_3$, preferably $R^4$ and $R^6$ are independently selected from the group consisting of O and S, and most preferably $R^4$ and $R^6$ are O, wherein the stereochemical configuration at the $P_\beta$ atom corresponds to that at the $P_\beta$ atom of the D1 diastereomer of beta-S-ARCA.

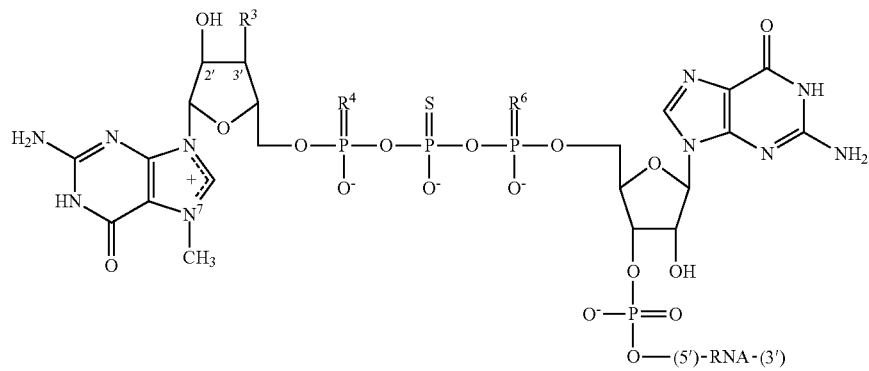

wherein R³ is selected from the group consisting of H, halo, and optionally substituted $C_1$-$C_{10}$ alkoxy, preferably R³ is selected from H, F, methoxy, ethoxy, and propoxy, preferably R³ is H or methoxy, R⁴ and R⁶ are independently selected from the group consisting of O, S, Se, and $BH_3$, preferably R⁴ and R⁶ are independently selected from the group consisting of O and S, and most preferably R⁴ and R⁶ are O, wherein the stereochemical configuration at the $P_\beta$ atom corresponds to that at the $P_\beta$ atom of the D1 diastereomer of beta-S-ARCA.

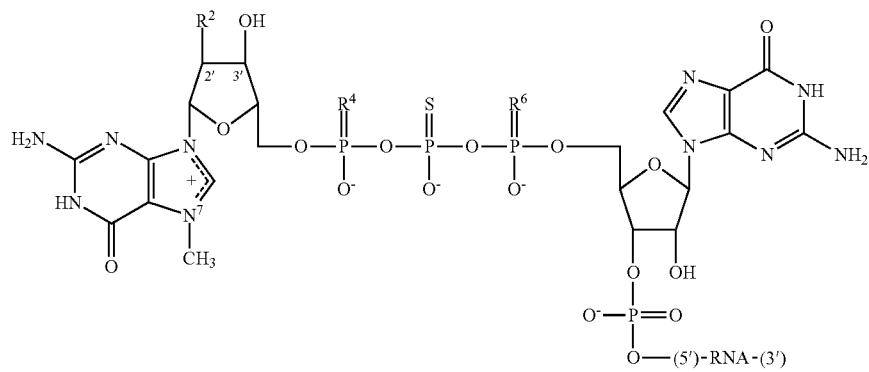

wherein R² is selected from the group consisting of H, halo, and optionally substituted $C_1$-$C_{10}$ alkoxy, preferably R² is selected from H, F, methoxy, ethoxy, and propoxy, preferably R² is H or methoxy, or R² is combined with the valence produced by removal of the hydrogen atom at position 4' of the ring to which R² is attached, wherein the bridging linkage from R² to the 4' position is defined as an —O—$CH_2$— group or —$CH_2$—O— group, R⁴ and R⁶ are independently selected from the group consisting of O, S, Se, and $BH_3$, preferably R⁴ and R⁶ are independently selected from the group consisting of O and S, and most preferably R⁴ and R⁶ are O, wherein the stereochemical configuration at the $P_\beta$ atom corresponds to that at the $P_\beta$ atom of the D1 diastereomer of beta-S-ARCA.

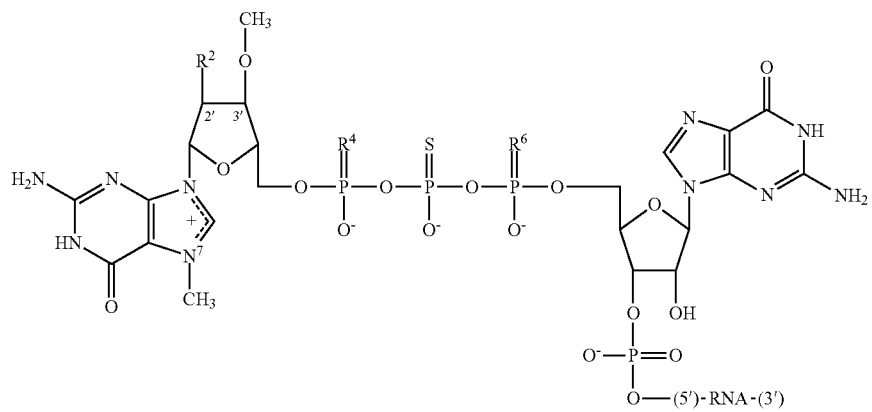

wherein $R^2$ is selected from the group consisting of H, OH, halo, and optionally substituted $C_1$-$C_{10}$ alkoxy, preferably $R^2$ is selected from H, OH, F, methoxy, ethoxy, and propoxy, preferably $R^2$ is OH, or $R^2$ is combined with the valence produced by removal of the hydrogen atom at position 4' of the ring to which $R^2$ is attached, wherein the bridging linkage from $R^2$ to the 4' position is defined as an —O—$CH_2$— group or —$CH_2$—O— group, $R^4$ and $R^6$ are independently selected from the group consisting of O, S, Se, and $BH_3$, preferably $R^4$ and $R^6$ are independently selected from the group consisting of O and S, and most preferably $R^4$ and $R^6$ are O, wherein the stereochemical configuration at the $P_\beta$ atom corresponds to that at the $P_\beta$ atom of the D1 diastereomer of beta-S-ARCA.

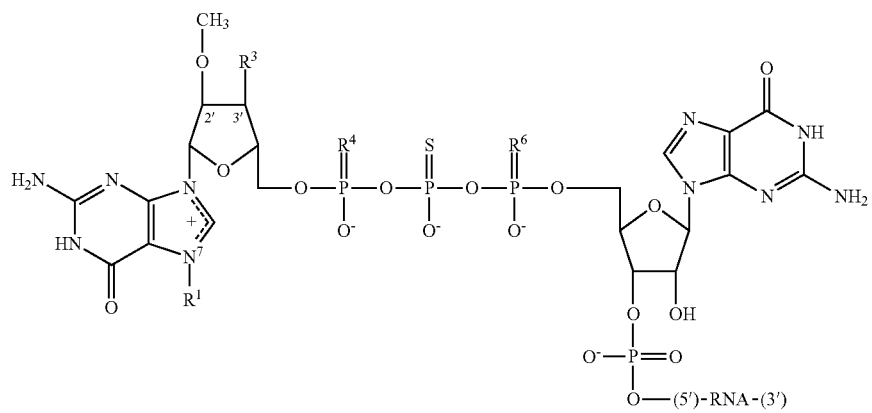

wherein $R^3$ is selected from the group consisting of H, OH, halo, and optionally substituted $C_1$-$C_{10}$ alkoxy, preferably $R^3$ is selected from H, OH, F, methoxy, ethoxy, and propoxy, preferably $R^3$ is OH, $R^4$ and $R^6$ are independently selected from the group consisting of O, S, Se, and $BH_3$, preferably $R^4$ and $R^6$ are independently selected from the group consisting of O and S, and most preferably $R^4$ and $R^6$ are O, wherein the stereochemical configuration at the $P_\beta$ atom corresponds to that at the $P_\beta$ atom of the D1 diastereomer of beta-S-ARCA.

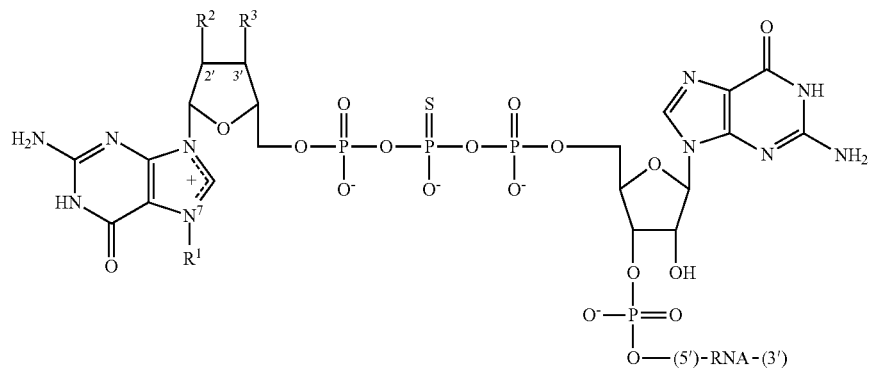

wherein R$^1$ is selected from the group consisting of optionally substituted C$_1$-C$_4$ alkyl, e.g., methyl, ethyl, propyl, butyl, optionally substituted benzyl, optionally substituted phenylethyl, or optionally substituted naphthylmethyl, optionally substituted C$_2$-C$_4$ alkenyl, e.g., ethenyl, propenyl, or butenyl, and optionally substituted aryl, R$^2$ and R$^3$ are independently selected from the group consisting of H, F, OH, methoxy, ethoxy, and propoxy, or R$^2$ and R$^3$ together form O—X—O, wherein X is selected from the group consisting of optionally substituted CH$_2$, CH$_2$CH$_2$, CH$_2$CH$_2$CH$_2$, CH$_2$CH(CH$_3$), and C(CH$_3$)$_2$, preferably R$^2$ and R$^3$ together from 2',3'-isopropylidene, or R$^2$ is combined with the valence produced by removal of the hydrogen atom at position 4' of the ring to which R$^2$ is attached, wherein the bridging linkage from R$^2$ to the 4' position is defined as an —O—CH$_2$— group or —CH$_2$—O— group, wherein preferably R$^2$ and R$^3$ are selected such that the 5'-cap cannot be incorporated into an RNA in the reverse orientation, wherein the stereochemical configuration at the P$_\beta$ atom corresponds to that at the P$_\beta$ atom of the D1 diastereomer of beta-S-ARCA.

dently selected from the group consisting of O and S, and most preferably R$^4$ and R$^6$ are O, n is 1, 2, or 3, preferably n is 1 or 2, more preferably n is 1, and wherein the stereochemical configuration at the P atom carrying S as substituent corresponds to that at the P$_\beta$ atom of the D1 diastereomer of beta-S-ARCA.

Preferably, the stability and translation efficiency of the RNA used in the present invention may be further modified as required. For example, the RNA may be stabilized and its translation increased by one or more modifications having a stabilizing and/or translation efficiency increasing effect. Such modifications are, for example, described in WO 2007/036366 incorporated herein by reference.

For example, RNA having an unmasked poly-A sequence (unmasked poly-A tail) is translated more efficiently than RNA having a masked poly-A sequence. The term "poly-A sequence" relates to a sequence of adenyl (A) residues which typically is located at the 3'-end of an RNA molecule and "unmasked poly-A sequence" means that the poly-A sequence at the 3'-end of an RNA molecule ends with an A of the poly-A sequence and is not followed by nucleotides other than A located at the 3'-end, i.e., down-stream, of the poly-A sequence. Furthermore, a long poly-A sequence of about 120 nucleotides results in optimal transcript stability and translation efficiency.

Thus, the RNA, preferably the mRNA used in the present invention may preferably further comprise a poly-A tail having a length of 10 to 500, preferably having a length of 30 to 300, more preferably having a length of 65 to 200, more preferably having a length of 100 to 150 nucleotides, e.g.,

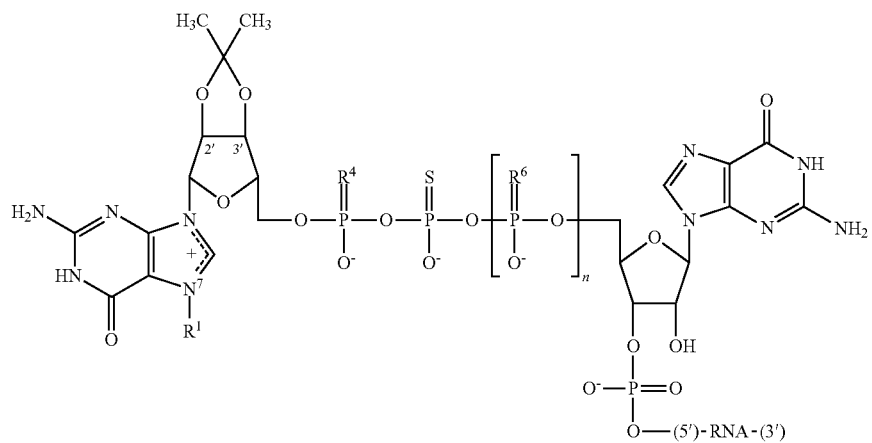

wherein R$^1$ is selected from the group consisting of optionally substituted C$_1$-C$_4$ alkyl, e.g., methyl, ethyl, propyl, butyl, optionally substituted benzyl, optionally substituted phenylethyl, or optionally substituted naphthylmethyl, optionally substituted C$_2$-C$_4$ alkenyl, e.g., ethenyl, propenyl, or butenyl, and optionally substituted aryl, R$^4$ and R$^6$ are independently selected from the group consisting of O, S, Se, and BH$_3$, preferably R$^4$ and R$^6$ are indepen- 100, 110, 120, 130, 140, or 150 nucleotides, preferably 120 nucleotides. Preferably, said poly-A sequence is an unmasked poly-A sequence. Thus, preferably, the RNA used in the present invention as specified above comprises an unmasked poly-A tail having a length of 10 to 500, preferably having a length of 30 to 300, more preferably having a length of 65 to 200, more preferably having a length of 100 to 150 nucleotides, e.g., 100, 110, 120, 130, 140, or 150 nucleotides, preferably 120 nucleotides.

In addition, incorporation of a 3'-untranslated region (UTR) into the 3'-untranslated region of an RNA molecule can result in an enhancement in translation efficiency. A synergistic effect may be achieved by incorporating two or more of such 3'-UTRs. The 3'-UTRs may be autologous or heterologous to the RNA into which they are introduced, for example, it may be the 3'-UTR of the beta-globin mRNA. Thus, preferably, the RNA, preferably the mRNA used in the present invention may further comprise one or more copies, preferably two copies of the 3'-untranslated region (3'-UTR) of the beta-globin gene, preferably of the human beta-globin gene.

It is particularly preferred that the RNA used in the present invention is modified by a combination of the above described modifications, i.e., incorporation of a poly-A sequence, unmasking of a poly-A sequence, and incorporation of one or more 3'-UTRs.

In a particularly preferred embodiment, the RNA used in the present invention encodes a peptide or protein comprising an immunogen, antigen or antigen peptide. In one embodiment, the peptide or protein is processed after expression to provide said immunogen, antigen or antigen peptide. In another embodiment, the peptide or protein itself is the immunogen, antigen or antigen peptide.

In a first aspect, the present invention provides a vaccine composition comprising an RNA having a structure as described above. In a preferred embodiment, said vaccine composition further comprises one or more pharmaceutically acceptable carriers, excipients, and/or diluents. Said vaccine composition may further comprise compounds or substances which are capable of enhancing and/or supporting an immune reaction in an individual. For example, the vaccine composition of the present invention may further comprise an adjuvant as described above or cytokines, for example, interleukin-12 (IL-12), granulocyte-macrophage colony-stimulating factor (GM-CSF), or interleukin-18 (IL-18). Furthermore, the vaccine composition according to the present invention may further comprise RNA stabilizing substances such as RNase inhibitors, pharmaceutically acceptable salts or buffers, preservatives such as benzalkonium chloride, chlorbutanol, parabene, or thimerosal, wetting agents, emulsifying agents, and/or additional drugs or active agents. In a particularly preferred embodiment, the RNA is present in the vaccine composition according to the present invention in the form of naked RNA. It is particularly preferred that the vaccine composition of the present invention is formulated for parenteral administration, for example, for intravenous, intraperitoneal, intramuscular, subcutaneous, intralymphatic, or intranodal administration, most preferably for intranodal administration. The vaccine composition of the invention is most preferably formulated for injection into lymph nodes, preferably inguinal lymph nodes, for injection into lymphatic vessels and/or the spleen. Preferably, the vaccine composition is in the form of an aqueous or non-aqueous solution which is isotonic with the blood of the recipient, i.e., the individual to be vaccinated. For example, Ringer solution, isotonic sodium chloride solution, or phosphate buffered saline (PBS) may be used. In particular, the vaccine composition is preferably sterile and comprises the above specified RNA in a therapeutically effective amount.

In a second aspect, the present invention provides an immature antigen presenting cell comprising an RNA as specified above. In a preferred embodiment, the immature antigen presenting cell is selected from the group consisting of immature macrophage, immature monocyte, immature B-cell, and immature dendritic cell, preferably the immature antigen presenting cell is an immature dendritic cell. In a particularly preferred embodiment, the immature antigen presenting cell according to the present invention is formulated in a pharmaceutical composition, said pharmaceutical composition preferably being suitable to elicit an immune response when administered to an individual, wherein the immune response is preferably directed against the protein or peptide encoded by the RNA or an antigen and/or immunogen comprised by the protein or peptide encoded by the RNA present in the immature antigen presenting cell of the present invention. Thus, the present invention provides a pharmaceutical composition comprising an immature antigen presenting cell according to the second aspect of the present invention.

In a third aspect, the present invention provides a method for eliciting an immune response in an individual comprising the step of administering to said individual the vaccine composition of the present invention or the immature antigen presenting cell of the present invention. Preferably, said immune response is specifically directed against the protein or peptide encoded by the RNA comprised by the vaccine composition or the immature antigen presenting cell of the present invention or is specifically directed against an antigen comprised by said protein or peptide. Said immune response may be therapeutic and/or protective. It is particularly preferred that said vaccine composition and said immature antigen presenting cells, preferably immature dendritic cells, are administered parenterally as specified above for the first aspect of the present invention, preferably by intranodal injection, preferably by injection into inguinal lymph nodes.

In a fourth aspect, the present invention provides a method for increasing the stability of an RNA in immature antigen presenting cells and/or for increasing the expression of an RNA in immature antigen presenting cells, said method comprising providing said RNA with a 5'-cap structure according to formula (I) as specified above. Preferably, said immature antigen presenting cells are selected from the group consisting of immature monocytes, immature macrophages, immature glia cells, immature B-cells, and immature dendritic cells, preferably the immature antigen presenting cells are immature dendritic cells. In order to assess the stability of an RNA in an immature antigen presenting cell, the skilled person may detect the presence of the studied RNA or quantify the amount of RNA within an immature antigen presenting cell after certain time points after introduction of said RNA, for example, by using real time RT-PCR as set forth in Example 4 herein below. The expression of an RNA in immature antigen presenting cells may be determined using an RNA encoding a marker protein such as luciferase or green fluorescent protein, preferably d2EGFP but may be any other marker protein known to the skilled person, and determining the expression of said marker protein at certain time points after introduction of the RNA as set forth in Example 3 herein below.

In a fifth aspect, the present invention provides a method for increasing the portion of MHC molecules which present an antigen of interest on the surface of an antigen presenting cell, said method comprising providing an RNA comprising a nucleotide sequence encoding a peptide or protein comprising said antigen of interest or an antigen peptide thereof, said RNA being modified with a 5'-cap structure according to formula (I) as specified above and transferring said RNA into an immature antigen presenting cell. Without being bound to any theory, it is assumed that modifying an RNA with a cap structure according to formula (I) increases the stability of said RNA, in particular within immature antigen presenting cells, for example, immature dendritic cells. This increased stability leads to an increased expression of said RNA and thus to an accumulation of the protein or peptide encoded by said RNA. Said protein or peptide may comprise an antigen or antigen peptide. Thus, after processing of said protein antigens or antigen peptides may be loaded on MHC molecules on the surface of the antigen presenting cell. Alternatively, said protein or peptide may be itself an antigen or antigen peptide and may be loaded on MHC molecules without processing. It is assumed, that an RNA encoding a particular protein or peptide comprising an antigen or antigen peptide which has been modified with a 5'-cap structure according to formula (I) increases the portion/fraction of MHC molecules on the cell surface of an antigen presenting cell which present a peptide derived from the protein or peptide encoded by said RNA when compared to the same RNA having a conventional 5'-cap, preferably when compared to the same RNA having an ARCA 5'-cap, and more preferably when compared to the same RNA having the same 5'-cap structure, except that the stereochemical configuration at the P atom having the substituent $R^5$ corresponds to that at the $P_\beta$ atom of beta-S-ARCA (D2). Since the density of MHC molecules presenting a particular antigen on the surface of an antigen presenting cell is decisive for the intensity of the induced immune response specific for said particular antigen, it is assumed that increasing the stability of an antigen encoding RNA which has been introduced into antigen presenting cells leads to an increased immune response against said particular antigen.

In a sixth aspect, the present invention provides a method for stimulating and/or activating immune effector cells, said method comprising providing an RNA comprising a nucleotide sequence encoding a peptide or protein comprising an antigen of interest or an antigen peptide thereof, said RNA being modified with a 5'-cap structure according to formula (I), transferring said RNA into immature antigen presenting cells, and contacting the antigen presenting cells with the immune effector cells. Preferably, said immune effector cells are antigen-specifically activated and/or stimulated. Preferably, by this method, the amount of antigen-specific effector cells, preferably T-cells, is increased. Preferably, the immature antigen presenting cells are immature dendritic cells. In a preferred embodiment, the immune effector cells are T-cells, preferably $CD4^+$ and/or $CD8^+$ cells. In one embodiment, the step of transferring said RNA into immature antigen presenting cells is performed in vitro by any nucleic acid transfer method, e.g., a transfection method, known to the skilled person such as lipofection, electroporation, or microinjection as described above. In another embodiment, the step of transferring said RNA into immature antigen presenting cells is performed in vivo, for example, by administering the RNA to an individual, preferably by parenteral administration, preferably by intralymphatic administration, preferably by injection into lymph node(s), i.e., by intranodal injection, by injection into lymphatic vessels, or by injection into the spleen. Preferably, said administration is by intranodal injection of the RNA which is preferably taken up by immature dendritic cells in the lymph node(s). The administered RNA is preferably in the form of naked RNA. In one embodiment, the step of contacting the antigen presenting cells with the immune effector cells is performed in vitro, for example, in a tissue culture dish. In another embodiment, the step of contacting the antigen presenting cells with the immune effector cells is performed in vivo. In this embodiment, the step of transferring the RNA into immature antigen presenting cells may be performed in vitro or in vivo as described above. For contacting the antigen presenting cells into which the RNA has been transferred in vitro with immune effector cells in vivo, the antigen presenting cells are administered to an individual, preferably by parenteral administration, for example, by intravenous, intramuscular, subcutaneous, intranodal, intralymphatic, or intraperitoneal injection, preferably by injection into the lymphatic system such as by injection into lymphatic vessel(s), the spleen, and/or lymph node(s), preferably inguinal lymph node(s). In an embodiment of the sixth aspect of the present invention, the method may further comprise the step of differentiating the immature antigen presenting cells into mature antigen presenting cells after transferring the RNA into the immature antigen presenting cells and before contacting the antigen presenting cells with the immune effector cells. The differentiation step may be performed in vitro or in vivo. For example, the RNA may be transferred into the immature antigen presenting cells, preferably into immature dendritic cells, the immature antigen presenting cells are differentiated in vitro, and the differentiated mature antigen presenting cells, preferably the mature dendritic cells, are contacted with immune effector cells in vitro or in vivo as described above, preferably in vivo. The immature antigen presenting cells into which the RNA is transferred in vitro may be isolated from an individual, for example a patient to be immunized, or they may be differentiated from hematopoietic stem cells.

A stimulation and/or activation of immune effector cells, in particular of T-cells, is typically associated with expansion, cytotoxic reactivity, and/or cytokine secretion of the immune effector cells. Thus, the skilled person may determine whether immune effector cells are stimulated and/or activated by simple in vitro tests, typically performed using T cells. Such T cells may be provided by transformed T cell lines such as T cell hybridomas or T cells which have been isolated from a mammal such as from a rodent, e.g., a mouse or a rat. Suitable T cell hybridomas are commercially available or may be generated by known methods. T cells may be isolated from a mammal by known methods (cf. Shimonkevitz et al., 1983, J. Exp. Med. 158: 303-316). A suitable experimental setting to test for T cell activation and/or stimulation is described below in steps (1) to (4). T cells express a suitable marker which may be tested and which indicates T cell activation or modulation of T cell activity. The murine T cell hybridoma DO11.10 may be used for this purpose, since said hybridoma expresses interleukin-2 (IL-2) upon activation. IL-2 concentrations may be determined to verify T cell activation/stimulation or to determine whether a composition is capable of modulating the activity of said T cell hybridoma. This test is performed by the following steps: (1) Providing T cells from a T cell hybridoma or by isolation from a mammal, (2) Cultivation of the T cells under conditions which allow for proliferation, (3) the proliferating T cells are contacted with an antigen presenting cell which has been contacted with an antigen or a nucleic acid encoding therefore, and (4) testing the T cells for a marker, for example, the IL-2 production is determined. Cells which are used for the test are cultured under conditions which allow for proliferation. For example, the DO11.10 T cell hybridoma is adequately cultured at 37° C. and 5% $CO_2$ in complete medium (RPMI 1640, supplemented with 10% FBS, penicillin/streptomycin, L-glutamine and $5\times10^{-5}$ M 2-mercaptoethanol). T cell activation signals are provided by antigen presenting cells which have been loaded with an appropriate antigenic peptide.

Alternatively, modulation of T cell activity may be verified by determining alterations or proliferation of antigen-specific T cells, which may be measured, for example, by known radiolabeling methods. For example, a labeled nucleotide may be added to a test culture medium. The incorporation of such labeled nucleotides into the DNA may serve as indicator for T cell proliferation. This test is not applicable for T cells that do not require antigen presentation for their proliferation such as T cell hybridomas. This test is useful for determining modulation of T cell activity in the case of untransformed T-cells which have been isolated from a mammal.

In a seventh aspect, the present invention provides a method for inducing an immune response in an individual, said method comprising providing an RNA comprising a nucleotide sequence encoding a peptide or protein comprising an antigen of interest or an antigen peptide thereof, said RNA being modified with a 5'-cap structure according to formula (I) and administering said RNA to said individual. The antigen of interest may be any antigen and is preferably as defined above. In a preferred embodiment, said RNA is administered in the form of naked RNA, preferably by parenteral administration, for example, by intravenous, intramuscular, subcutaneous, intranodal, intralymphatic, or intraperitoneal injection, preferably by injection into the lymphatic system such as by injection into lymphatic vessel(s), the spleen, and/or lymph node(s), preferably inguinal lymph node(s). Preferably, the administered RNA is taken up by immature dendritic cells of the individual. Preferably, the immune response is protective and/or therapeutic, for example, is useful for treating and/or preventing diseases such as cancerous diseases or infectious diseases.

In an eighth aspect, the present invention provides a method for inducing an immune response in an individual, said method comprising providing an RNA comprising a nucleotide sequence encoding a peptide or protein comprising an antigen of interest or an antigen peptide thereof, said RNA being modified with a 5'-cap structure according to formula (I), transferring said RNA into immature antigen presenting cells, and administering the antigen presenting cells to said individual. In this aspect of the present invention, the RNA is transferred into immature antigen presenting cells in vitro by any nucleic acid transfer method, e.g., transfection such as lipofection, electroporation, or microinjection, known to the skilled person as described above. Preferably, the immature antigen presenting cells are immature dendritic cells. The immature antigen presenting cells into which the RNA is transferred in vitro may be isolated from an individual, for example, a patient to be immunized, or they may be differentiated from hematopoietic stem cells, wherein the hematopoietic stem cells may be isolated from the individual. The immature antigen presenting cells or the hematopoietic stem cells may be isolated from the individual by leukapheresis. Preferably, the immature antigen presenting cells are immature dendritic cells. Preferably, the immature antigen presenting cells are isolated from the individual to be immunized, the RNA is transferred into said isolated cells, and the cells are transferred back to said individual, preferably by parenteral administration, for example, by intravenous, intramuscular, subcutaneous, intranodal, intralymphatic, or intraperitoneal injection, preferably by injection into the lymphatic system such as by injection into lymphatic vessel(s), the spleen, and/or lymph node(s), preferably inguinal lymph node(s).

The ability to induce an immune reaction, including the suitability for vaccination against a target disease, may be readily determined by in vivo tests. For example, a composition, e.g., a vaccine composition or a pharmaceutical composition, may be administered to a mammal such as a laboratory animal, e.g., a mouse, rat, rabbit, etc., and blood samples may be taken from said animal before administration of the composition and at defined time points after administration of the composition, for example, 1, 2, 3, 4, 5, 6, 7, and 8 weeks after administration. Serum may be generated from the blood samples and the development of antibodies generated upon administration/immunization may be determined. For example, the concentration of antibodies may be determined. Furthermore, T cells may be isolated from the blood and/or the lymphatic system of the mammal, which may be tested for their reactivity against the antigen used for the immunization. Any readout system which is known to the skilled person may be used, for example, proliferation assays, cytokine secretion assays, assays to test for cytotoxic activity, or tetramer analysis etc. may be used. Furthermore, the increase of immune reactivity may also be determined by determining the number of antigen-specific T-cells, their cytotoxic potential, or their cytokine secretion pattern as set forth above.

Furthermore, the present invention provides the RNA described herein, the vaccine composition according to the first aspect of the present invention, the immature antigen presenting cells and the pharmaceutical composition comprising said cells according to the second aspect of the present invention for use in a medical application, preferably for inducing an immune response in an individual, e.g., for vaccination of an individual, for example, for preventing a cancerous disease or an infectious disease in said individual or for treating an individual suffering from a cancerous or infectious disease.

The methods of the present invention, in particular, the methods for activating and/or stimulating immune effector cells and inducing an immune response in an individual as well as the vaccine composition, the immature antigen presenting cells, and the RNA for use in said methods allow for a quantitative increase in the frequency of antigen-specific T-lymphocytes after the RNA-based immunization. This increase in efficiency may be exploited for immunotherapy of patients with respect to better clinical efficiency or reduction of vaccine dosage. Furthermore, the present invention provides the opportunity to vastly amplify antigen-specific T cells from barely present precursor T-cells. Moreover, the increase in efficiency applying the present invention is accompanied by cost reduction.

The present invention is described in detail by the figures and examples below, which are used only for illustration purposes and are not meant to be limiting. Owing to the description and the examples, further embodiments which are likewise included in the invention are accessible to the skilled worker.

EXAMPLES

Example 1

Generation of Human Monocyte-Derived Dendritic Cells

Cell culture flasks (150 cm$^2$, Falcon Nr 355001), DC medium (RPMI—Roswell Park Memorial Institute medium 1640 with 2 mM glutamine, 100 U/ml penicillin, 100 µg/ml streptomycin, 1 mM sodium pyruvate, non-essential amino acids and 10% heat inactivated human AB-Serum; all Invitrogen, Karlsruhe, Germany) supplemented with 1000 U/ml human granulocyte-macrophage colony-stimulating factor (GM-CSF, Essex, Luzern, Switzerland) and 1000 U/ml IL-4 (human Interleukin 4, Strathmann Biotech, Hamburg, Germany), DPBS/EDTA (DPBS—Dulbecco's Phosphate Buffered Saline from Invitrogen, Karlsruhe, Germany, with 2 ml EDTA—Ethylenediaminetetraacetic acid; Sigma-Aldrich, Taufkirchen, Germany), 15 ml and 50 ml reaction tubes, disposable pipettes, pipette tips, FACS (Fluorescence-activated cell sorting) tubes, cooling centrifuge (4° C.), ice.

Procedure:

Day 0:

CD14 positive cells have been selected using bead-coupled anti CD14 antibodies (Miltenyi Biotec) according to the manufacturer's instructions and samples of the eluate, run through, and the Peripheral Blood Mononuclear Cell (PBMC) fraction have been kept for later FACS analysis (cf. Example 2). Cells have been counted after elution and centrifugation (15 minutes, 340 rcf) was performed at 4° C. The cells have been resuspended in DC medium at a density of about $1\times10^6$ cells/ml (max. $5\times10^7$ cells per flask). 1000 U/ml IL-4 and 1000 U/ml GM-CSF (as described above) have been added to the medium Day +2 (optionally +3):

One third of the medium has been removed and centrifuged at 4° C. (15 minutes, 340 rcf). The same volume of medium containing 2000 U/ml IL-4 and 2000 U/ml GM-CSF has been added.

Day +5 (optionally +4):

One third of the medium has been removed and centrifuged at 4° C. (15 minutes, 340 rcf). The same volume of medium containing 2000 U/ml IL-4 and 2000 U/ml GM-CSF has been added.

Day +7:

The cells have been removed from the bottom of the tissue culture flask by repeatedly pipetting up and down. The entire medium has been removed and, the flask has been rinsed with about 30 ml cold PBS/EDTA. The cells have been harvested by centrifugation and resuspended in 10 ml cold DC medium. The cells have been placed on ice and counted. A sample of the cells was kept for later FACS analysis. The density of the cells was adjusted to $1.0\times10^7/40$ ml with DC medium and 40 ml of DC medium has been added per flask. The following cytokines have been added to the medium:

U/ml IL-4
U/ml GM-CSF
10 ng/ml IL-1b
10 ng/ml TNF-a
1000 µml IL-6
1 µg/ml PGE2

Day +9 (optionally +10):

The cells have been removed from the tissue culture flask by gentle rinsing. Cells have been counted and a sample has been kept for later FACS analysis (cf. Example 2). Cells have been centrifuged and the cell number was adjusted as needed.

Example 2

FACS Staining

About $2\times10^5$ cells have been taken for each staining in a FACS tube. The volume was adjusted to 100µ with FACS buffer (DPBS, Invitrogen, Karlsruhe, Germany, with 5 mM EDTA, Sigma-Aldrich, Taufkirchen, Germany, and 5% FCS, Invitrogen, Karlsruhe, Germany). 5 µl α-CDx-FITC and optionally 5 ml α-CDy-PE have been added to the FACS tubes. The tubes have been incubated for 30 to 40 minutes at 4° C. in the dark before 4 ml of FACS buffer have been added and the samples have been centrifuged. The supernatant was aspirated off the cell pellet and the cells have been re-suspended in 400 µl FACS buffer and stored at 4° C.

PBMCs have been stained using α-CD14-FITC (BD Biosciences) and α-CD3-PE (BD Biosciences). In a separate staining PBMCs have been stained using α-CD19-PE (BD Biosciences). Staining was performed on day 7 and day 9. The cell samples have been stored on ice until the staining was performed.

Example 3

Figure 2:
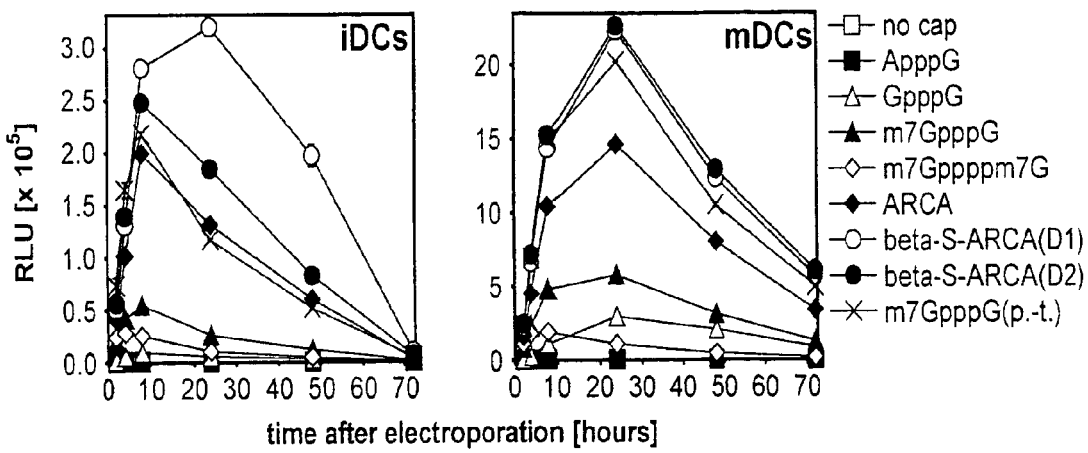
FIG. 2. Effect of the 5'-cap structure on protein expression in dendritic cells. (A) Immature and mature dendritic cells (iDCs and mDCs, respectively) have been electroporated with the same amount of luciferase encoding RNA which has been transcribed in presence of various cap dinucleotides (as indicated) or wherein the 5'-cap has been incorporated post-transcriptionally using the capping enzyme of vaccinia virus ($m^7$GpppG(p.-t.)). The luciferase activity (given in RLU) was measured in duplicates after 2, 4, 8, 24, 48, and 72 hours. Shown is mean±standard deviation. (B) iDCs and mDCs have been electroporated with the same amount of d2eGFP encoding RNA which has been prepared as described in (A). Cells have been harvested after 2, 4, 8, 24, 48, and 72 hours and the d2eGFP fluorescence (given in MFI) was determined using flow cytometry.
Figure 2:
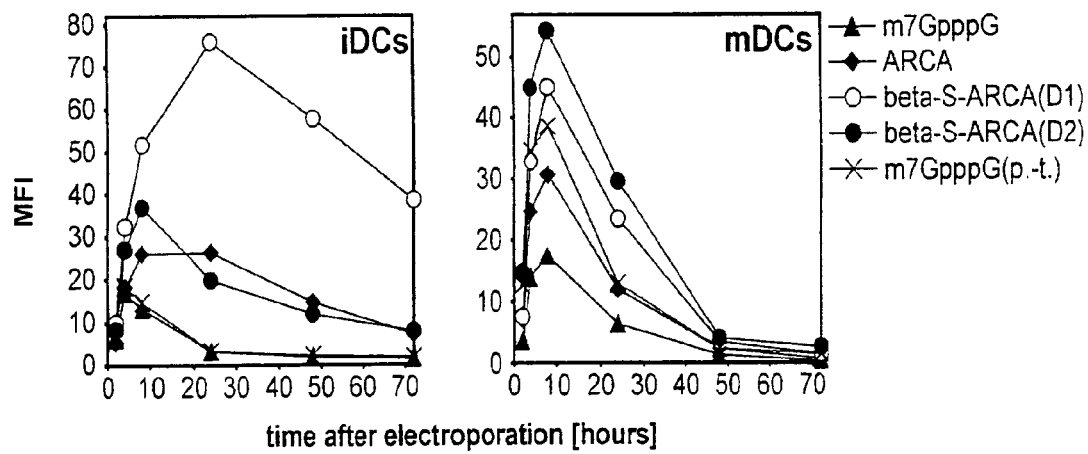

RNA with a Specific Phosphorothioate Cap Analog at the 5'-End Results in an Enhanced and Prolonged Protein Expression in Immature Dendritic Cells RNAs encoding for luciferase have been transcribed in vitro using optimized vector templates (WO2007/036366; Holtkamp et al., 2006, *Blood* 108: 4009-4017). Linearized vector DNAs were quantified spectrophotometrically and subjected to in vitro transcription essentially as described by Pokrovskaya and Gurevich (Pokrovskava & Gurevich, 1994, *Anal. Biochem.* 220: 420-423). One of the cap dinucleotides m$^7$GpppG (Darzynkiewicz et al., 1988, *Nucleic Acids Res.* 16: 8953-8962), m$^7$Gppppm$^7$G, m$_2^{(7,3'-O)}$GpppG (designated in the following as ARCA) (Stepinski et al., 1995, *Nucleosides Nucleotides* 14: 717-721, Stepinski et al., 2001, RNA 7: 1486-1495), m$_2^{(7,2'-O)}$GppspG(D1) (in the present invention named beta-S-ARCA(D1)) or m$_2^{(7,2'-O)}$GppspG(D2) (in the present invention named beta-S-ARCA(D2)) (Kowalska et al., 2008, *RNA* 14:1119-1131) have been added to the transcription reaction to obtain RNAs with the correspondingly modified 5'-cap structures (cf. also FIG. 1). In the reactions with cap-analog, GTP was present at 1.5 mM, while the cap-analog was present at 6.0 mM. GTP was present at 7.5 mM in the reactions without cap-analog. At the end of the transcription reaction, linearized vector DNA was digested with 0.1 U/µl TURBO DNase (Ambion, Austin/TX, USA) for 15 minutes at 37° C. RNAs were purified from these reactions using the MEGAclear Kit (Ambion, Austin/TX, USA) as per manufacturer's protocol. If desired, the RNA transcribed in the absence of a cap-analog was subsequently provided with an m7 GpppG cap using the capping enzyme of the vaccinia virus (Epicentre, Madison/WI, USA) for post-transcriptional capping (m7 GpppG(p.-t.)) according to the manufacturer's instructions, and the RNA was purified once more using the MEGAclear Kit (Ambion, Austin/TX, USA) as per manufacturer's protocol. RNAs prepared as described above were introduced into human immature and mature dendritic cells using electroporation (with 300 V and 150 µF using a Gene Pulser II, Bio-Rad, München, Germany) and the expression of the reporter protein luciferase was determined during a time course of 72 hours. To this end, the amount of luciferase protein was determined after 2, 4, 8, 24, 48, and 72 hours by measuring luciferase activity (which is proportional to the protein amount; FIG. 2). By the expression analysis of the encoded protein, it is possible to determine the translation efficiency of an RNA (corresponding to the maximal slope of the curve) and the functional RNA stability (given by the time point of the maximum of the curve). Furthermore, the integral of the curve corresponds to the intensity of the entire protein expression across the observed time range.

The highest total protein expression in immature dendritic cells was observed for RNA which has been transcribed in presence of beta-S-ARCA(D1) (FIG. 2A; left panel). This result was unexpected because both in HC11 cells as well as in in vitro translation systems RNA with beta-S-ARCA(D2) at the 5'-end resulted in the strongest total expression (cf.

Background of the Invention). The RNA with beta-S-ARCA (D2) at the 5'-end resulted only in the second best total expression in immature dendritic cells and is followed by RNA with ARCA at the 5'-end and post-transcriptionally modified RNA.

In accordance with the fact that m$^7$GpppG can be incorporated in reverse orientation during in vitro transcription (thus, around half of the RNA containing a 5'-cap is functional for translation) the expression of RNA which was transcribed using m$^7$GpppG is clearly less than for the other RNAs. By the combined effect on translation efficiencies and functional RNA stability beta-S-ARCA(D1) results in a total protein expression which is increased by more than 13-fold compared to RNA which has been synthesized in presence of m$^7$GpppG. Compared to RNA with ARCA at the 5'-end or post-transcriptionally modified RNA expression from RNA possessing beta-S-ARCA(D1) is increased by a factor of around 3. Total protein expression from beta-S-ARCA(D1) RNA is increased about 2-fold compared to total protein expression from beta-S-ARCA(D2) RNA (Table 1).

In comparison to RNA with m$^7$GpppG the translation efficiencies of RNA with ARCA is increased about 2.5-fold, with beta-S-ARCA(D1) about 3.4-fold, with beta-S-ARCA(D2) about 3.5-fold and with a post-transcriptionally modified RNA about 4.1-fold (Table 1).

Besides the effect on the translation efficiency, the various cap structures also influence the functional RNA stability in immature dendritic cells. The protein expression of RNA which has been transcribed in presence of m$^7$GpppG exhibits its maximum around 8 hours after electroporation (Table 1). By contrast, the maximum of expression of RNA with ARCA or beta-S-ARCA(D2) is after 12 hours and beta-S-ARCA (D1) increases the functional RNA stability even further with a maximum after more than 15 hours.

TABLE 1

Impact of the 5'-RNA cap structure on the translation efficiency (given by the maximal slope of the curves in FIG. 2A). The time point of maximal protein expression, and the total protein expression throughout the time course of the experiment. For each cell type (immature and mature dendritic cells [iDCs and mDCs, respectively]) the translation efficiency and the total signal for cells which have been electroporated with RNA which has been transcribed in presence of m$^7$GpppG has been set to 1. Given are means ± standard deviation.

| 5' cap structure | cells | transl. efficiency | time of max. (hours) | relative total protein expression |
|---|---|---|---|---|
| no cap | iDCs | 0.00 ± 0.00 | n.a. | 0.011 ± 0.000 |
| ApppG | iDCs | 0.01 ± 0.00 | n.a. | 0.022 ± 0.001 |
| GpppG | iDCs | 0.18 ± 0.01 | 11.5 ± 0.0 | 0.221 ± 0.001 |
| m7GpppG | iDCs | 1.00 ± 0.04 | 8.1 ± 1.1 | 1.000 ± 0.007 |
| m7Gppppm7G | iDCs | 0.20 ± 0.10 | 4.9 ± 0.1 | 0.404 ± 0.004 |
| ARCA | iDCs | 2.52 ± 0.19 | 12.6 ± 0.1 | 4.777 ± 0.042 |
| beta-S-ARCA(D1) | iDCs | 3.36 ± 0.09 | 15.4 ± 0.1 | 13.094 ± 0.307 |
| beta-S-ARCA(D2) | iDCs | 3.53 ± 0.17 | 12.8 ± 0.0 | 6.570 ± 0.075 |
| m7GpppG(p.-t.) | iDCs | 4.12 ± 0.53 | 8.4 ± 1.4 | 4.289 ± 0.056 |
| no cap | mDCs | 0.00 ± 0.00 | n.a. | 0.002 ± 0.000 |
| ApppG | mDCs | 0.01 ± 0.00 | n.a. | 0.008 ± 0.000 |
| GpppG | mDCs | 0.31 ± 0.02 | 27.5 ± 0.5 | 0.593 ± 0.005 |
| m7GpppG | mDCs | 1.00 ± 0.05 | 16.0 ± 0.3 | 1.000 ± 0.003 |
| m7Gppppm7G | mDCs | 0.56 ± 0.04 | 6.0 ± 0.3 | 0.176 ± 0.001 |
| ARCA | mDCs | 2.16 ± 0.00 | 17.5 ± 0.3 | 2.526 ± 0.015 |
| beta-S-ARCA(D1) | mDCs | 3.05 ± 0.14 | 20.1 ± 0.1 | 3.884 ± 0.032 |
| beta-S-ARCA(D2) | mDCs | 3.30 ± 0.03 | 19.4 ± 0.1 | 4.042 ± 0.053 |
| m7GpppG(p.-t.) | mDCs | 3.16 ± 0.08 | 17.5 ± 0.3 | 3.421 ± 0.010 |

Interestingly, we have observed in immature dendritic cells that RNA with the m$^7$Gppppm$^7$G-cap which previously resulted in an increase in expression in the in vitro translation system (Grudzien et al., 2004, RNA J. 10: 1479-1487), results in an expression in immature dendritic cells which is even lower than that of RNA which has been transcribed in presence of m$^7$GpppG. RNAs which have been applied as controls without cap or with a cap that is not recognized by the translation machinery (ApppG and GpppG) do not result in any significant expression.

In mature dendritic cells the effect of the various 5'-RNA structures is different than in immature dendritic cells. First, it is noticeable that the functional RNA stability is generally higher than in immature dendritic cells and is only marginally dependent on the type of 5'-end of the RNA. Second, the order with respect to the total protein expression differs from that in immature dendritic cells: RNA with beta-S-ARCA(D2) results in the highest protein expression in mature dendritic cells followed by beta-S-ARCA(D1) RNA, post-transcriptionally modified RNA, and then RNA with ARCA at the 5'-end. Furthermore, the difference in expression levels in mature dendritic cells is not as pronounced as in immature dendritic cells. This is in accordance with the lower influence of cap structures on the functional RNA stability in mature dendritic cells. RNA with m$^7$Gppppm$^7$G is also poorly translated in mature dendritic cells. These data support the assumption that this cap can only poorly recruit the translation machinery in vivo contrary to the data in vitro. The control RNAs without cap or with ApppG and GpppG, respectively, do not result in protein expression as expected.

To confirm that the observed effect of the RNA cap structures is independent of the RNA encoded protein, we have repeated the experiments with RNA encoding a green fluorescent protein (designated d2eGFP) using the same optimized vectors as described above for in vitro transcription. The amount of d2eGFP at different time points after introduction of the RNAs in immature and mature dendritic cells was determined using flow cytometry and the obtained results were very similar to those with luciferase encoding RNAs (cf. FIGS. 2A and B). RNA with beta-S-ARCA(D1) also resulted in the highest total protein expression in immature dendritic cells (FIG. 2B; left panel). As observed with luciferase encoding RNAs this effect is specific for immature dendritic cells. This confirms the superiority of beta-S-ARCA(D1) versus all other cap analogs and versus post-transcriptional modification regarding total protein expression in immature dendritic cells. In mature dendritic cells, RNAs with beta-S-ARCA (D2) resulted in the highest total protein expression, followed by RNA with beta-S-ARCA(D1), post-transcriptionally modified RNA, and then RNA with ARCA. In summary, these data show that the cap structure at the 5'-end of the RNAs exhibit a differential influence on functional RNA stability and translation efficiency in immature and mature dendritic cells. In particular, the effect of beta-S-ARCA(D1) in immature dendritic cells is unique and has not been observed before.

Example 4

Preferential Translation of RNAs with Beta-S-ARCA(D1) at the 5'-End in Immature Dendritic Cells The results described so far indicate that the translational efficiency of an mRNA is influenced in dendritic cells by the type of the cap structure at its 5' end. This is most likely due to differences in the efficiency by which the translational machinery is recruited to the different 5' cap-structures. To corroborate this, we next analyzed (i) the effect of the RNA dose that is used for electroporation into immature dendritic cells, and (ii) the impact of a second RNA co-electroporated into immature dendritic cells on the protein expression. By increasing the amount of the electroporated mRNA, it is expected that at some point one or more translation factor(s) will become rate limiting in the cell, which will then restrict the amount of protein that can be synthesized from the exogenous RNA. Similarly, a second RNA will compete for the translation machinery, again influencing the translation efficiency.

Figure 3:
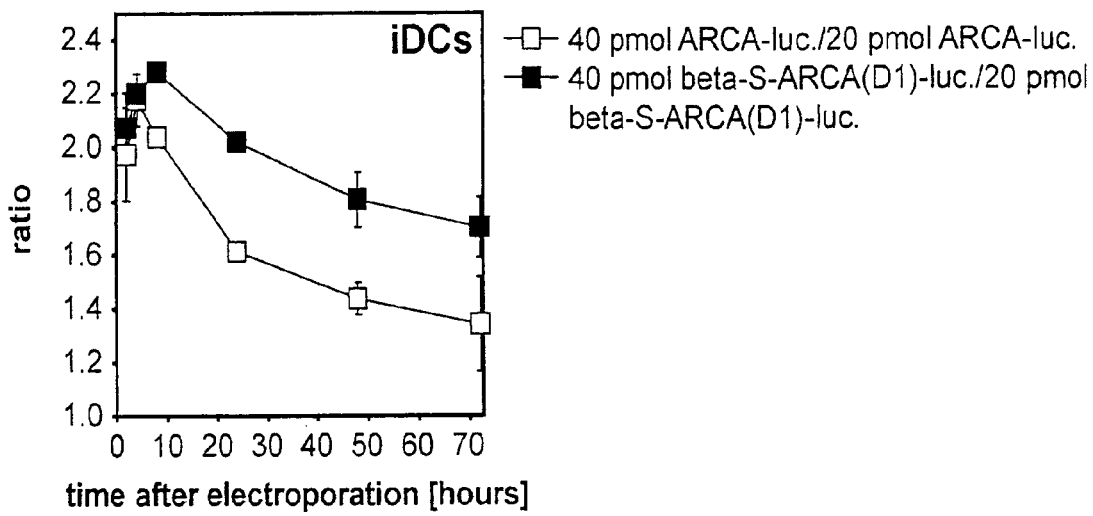
FIG. 3. Competition for translation between ARCA- and beta-S-ARCA(D1)-capped RNAs. Immature dendritic cells (iDCs) were electroporated with (A) increasing amounts of luciferase-encoding RNAs or (B) the indicated amounts of luciferase- and d2eGFP-encoding mRNAs, which were co-transcriptionally capped either with ARCA or beta-S-ARCA (D1) as indicated. The luciferase activity was measured after 2, 4, 8, 24, 48, and 72 hours. Shown is (A) the ratio between the luciferase activities obtained after electroporation with 40 and 20 pmol luciferase-encoding RNAs (±SD of two independent experiments), and (B) the relative luciferase activity compared to cells electroporated with only luciferase-encoding RNA without RNA (set to 1 for both ARCA- and beta-S-ARCA(D1)-capped RNA).
Figure 3:
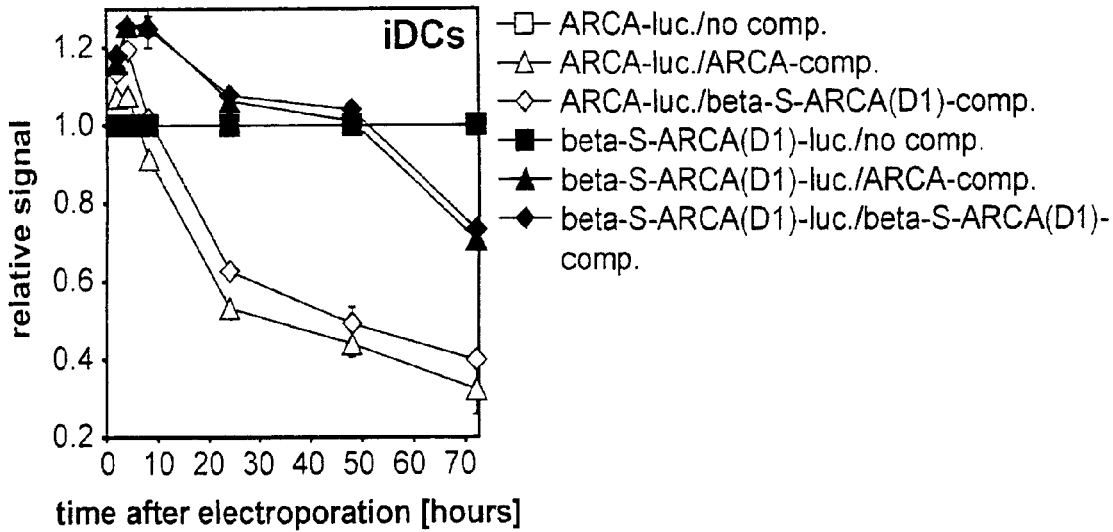

Increasing amounts (20 pmol and 40 pmol) of luciferase-encoding RNAs co-transcriptionally capped with either ARCA or beta-S-ARCA(D1) were electroporated into immature dendritic cells, and the luciferase activity was measured after 2, 4, 8, 24, 48, and 72 hours. Interestingly, the luciferase activity measured upon using 40 pmol ARCA-capped RNA decreased relatively to the signal obtained with 20 pmol ARCA-capped RNA 24 hours after electroporation (FIG. 3A). At this time-point, the level of luciferase protein was only about 1.6-fold as high as when half the amount of RNA was used. This ratio decreased even further 48 and 72 hours after electroporation (1.4- and 1.2-fold, respectively). In contrast, for beta-S-ARCA(D1)-capped RNA the level of luciferase protein was generally proportional to the amount of RNA that was used for electroporation over the whole course of the experiment, i.e. the signal obtained upon electroporation of 40 pmol RNA was about twice as high as the signal when 20 pmol RNA were used for each time-point.

Comparably, co-electroporation of the same amount of d2eGFP-encoding RNA (capped with either ARCA or beta-S-ARCA(D1)) into immature dendritic cells decreased the expression of ARCA-capped but not beta-S-ARCA(D1)-capped luciferase-encoding RNA after 24, 48, and 72 hours compared to a control that was electroporated with only RNA coding for luciferase (FIG. 3B). Taken together this indicates that in immature dendritic cells ARCA-capped RNA can apparently not as efficiently compete for the translational machinery with endogenous RNA as beta-S-ARCA(D1)-capped RNA when the RNA level increases beyond a certain threshold set most likely by the availability of one or more limiting translation factor(s). Thus, the incorporation of beta-S-ARCA(D1) at the 5' end gives RNAs that are preferentially translated when competing with endogenous or another exogenous RNA.

Example 5

Stabilization of RNA by Phosphorothioate Cap Analogs in Immature Dendritic Cells The data shown in FIG. 2 indicate that the type of 5'-cap influences not only the translational efficiency, but also the functional mRNA stability in dendritic cells. To substantiate this, we have determined the absolute RNA stabilities of RNAs with the various 5'-cap structures in dendritic cells. The absolute stability is given by the half life of the RNA.

Human immature and mature dendritic cells were electroporated with RNAs encoding d2eGFP which have been provided with a cap analog co-transcriptionally or post-transcriptionally using the capping enzymes of the vaccinia virus. A portion of the cells was harvested after 2, 4, 8, 24, 48, and 72 hours, and the amount of d2eGFP encoding RNA was determined relatively to an endogenous RNA (the hypoxanthine phosphoribosyltransferase encoding RNA) using real time RT-PCR (FIG. 4). The determined values were used to calculate the half life of the RNAs (Table 2). As control for electroporation and protein expression the amount of d2eGFP was determined after 24 hours using flow cytometric quantification, wherein the same order was measured as in the above described experiments.

TABLE 2

Stability of the RNAs with different cap structures in immature dendritic cells (iDCs) and mature dendritic cells (mDCs). mean ± standard deviation.

| 5' cap structure | cells | mRNA half-life (h) (2 to 8 h after electroporation) | mRNA half-life (h) (24 to 72 h after electroporation) | cells | mRNA half-life (h) (2 to 72 h after electroporation) |
|---|---|---|---|---|---|
| no cap | iDCs | 1.41 ± 0.02 | n.a. | mDCs | 10.36 ± 0.18 |
| ApppG | iDCs | 5.98 ± 0.49 | 14.06 ± 1.43 | mDCs | 15.30 ± 0.64 |
| GpppG | iDCs | 4.82 ± 0.71 | 24.45 ± 4.40 | mDCs | 14.64 ± 0.32 |
| m7GpppG | iDCs | 5.82 ± 1.46 | 16.10 ± 1.83 | mDCs | 13.11 ± 0.82 |
| m7Gppppm7G | iDCs | 2.37 ± 0.09 | 19.37 ± 0.34 | mDCs | 11.88 ± 0.39 |
| ARCA | iDCs | 5.47 ± 0.87 | 15.50 ± 1.57 | mDCs | 13.63 ± 0.55 |
| beta-S-ARCA(D1) | iDCs | 8.27 ± 1.15 | 27.00 ± 2.85 | mDCs | 13.94 ± 0.82 |
| beta-S-ARCA(D2) | iDCs | 6.72 ± 1.48 | 18.09 ± 0.81 | mDCs | 14.20 ± 0.89 |
| m7GpppG(p.-t.) | iDCs | 6.11 ± 0.33 | 15.60 ± 7.24 | mDCs | 13.27 ± 0.28 |

Figure 4A:
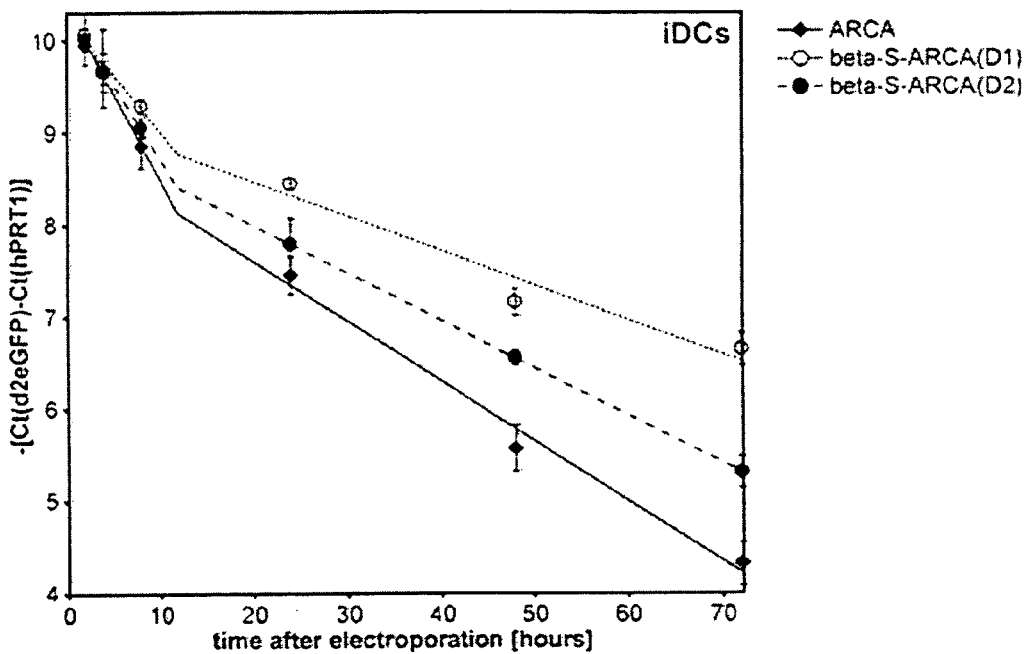
FIG. 4A), or to a monophasic decay (mDCs.

Interestingly, we observed for all RNAs in immature dendritic cells a two-phase degradation kinetic of the RNA, with the exception of RNA without cap, which has been almost completely degraded already after 8 hours (FIG. 4A and Table 2). Within the first 8 hours after electroporation the RNAs were degraded more rapidly compared to the subsequent degradation phase until the end of the experiments.

RNA with beta-S-ARCA(D1) at the 5'-end is the most stable RNA in immature dendritic cells both during the early degradation phase as well as during the late degradation phase (with half lives of around 8 and 27 hours, respectively; FIG. 4A and Table 2). This is unexpected since in the in vitro studies beta-S-ARCA(D2) exhibited the best protection against degradation by the decapping enzyme Dcp2. Most of the RNAs with a cap exhibited half lives in the range of 5 to 7 hours in the early degradation phase and between 15 and 18 hours in the late degradation phase, respectively. This means that indeed beta-S-ARCA(D1) exhibits a clear effect on the stabilization of RNA—in particular during the late degradation phase. Most of the other 5'-RNA structures, however, only exhibited a minor effect on the absolute RNA stability. An exception is m$^7$GppppGm$^7$G. RNA with this cap at the 5'-end is the most unstable RNA with a half life of less than 2.5 hours during the first 8 hours after electroporation. m⁷GppppGm⁷G RNA which is still present in the cell 8 hours after electroporation is interestingly as stable as the other RNAs with a half life of about 20 hours.

Figure 4B:
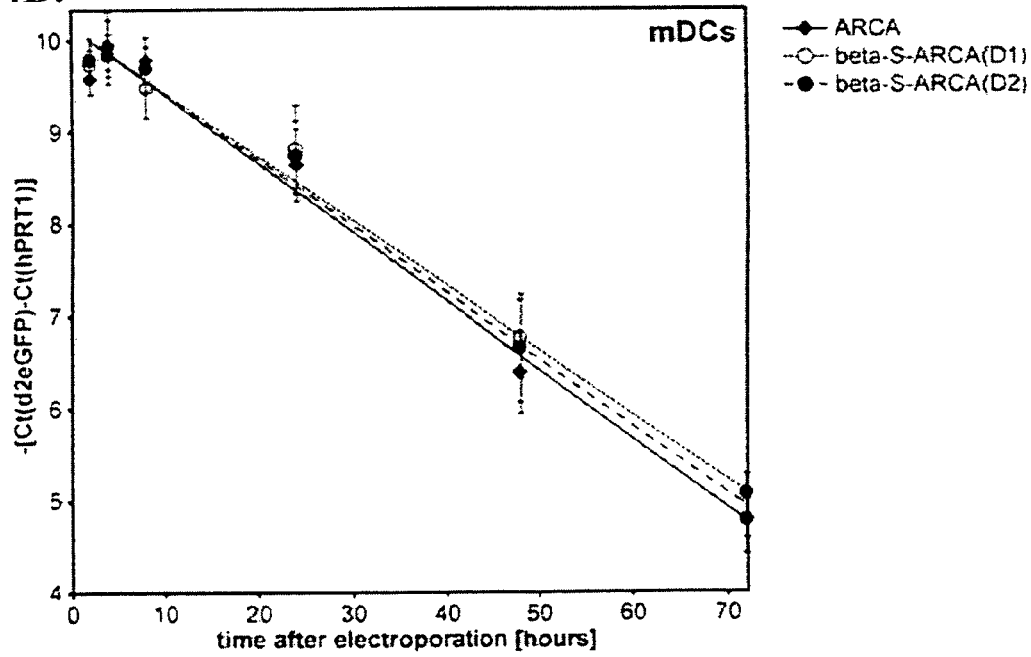
FIG. 4B).

In contrast to immature dendritic cells, the RNA degradation in mature dendritic cells follows uniform kinetics throughout the entire studied time course (FIG. 4B and Table 2). Compared to the initial degradation kinetics in immature dendritic cells, RNA was clearly more stable in mature dendritic cells and exhibited half lives which were comparable to those in the late degradation phase in immature dendritic cells. As was already observed in immature dendritic cells, the absolute stability is only marginally dependent on the cap structure, since all RNAs with a cap have similar half lives between 13 and 15 hours (with the exception of RNA with m⁷Gppppm⁷G at the 5'-end which exhibited a half life below 12 hours). Even RNA lacking a cap is quite stable in mature dendritic cells with a half life of more than 10 hours. The comparable half lives of the RNAs are in accordance with the comparable functional RNA stabilities in mature dendritic cells (cf. Table 1).

In summary, this experiment shows that the decisive factor for the intensity and duration of protein expression of RNA with various 5'-cap structures in mature dendritic cells is the translation efficiency.

Example 6

Increased Expression of RNA with Beta-S-ARCA(D1) at the 5'-End after Injection into the Lymph Nodes of Mice Recently, we were able to show that the injection of RNA into lymph nodes (intranodal injection) is the most promising approach to obtain an immune response against the encoded antigen (DE 10 2008 061 522.6). RNA which is administered in this way is primarily taken up by immature dendritic cells. Thus, we have investigated whether stronger protein expression is also observed in lymph nodes for beta-S-ARCA(D1) RNA compared to RNAs with other cap structures (analyzed exemplarily for ARCA which we have applied in the earlier studies). Luciferase encoding RNAs (as described above) which either have been transcribed in presence of ARCA or beta-S-ARCA(D1) have been injected into the inguinal lymph nodes of mice. After uptake of the RNA by cells of the lymph nodes and translation of the encoded luciferase, protein expression was quantified by measuring luciferase activity using in vivo imaging. An aqueous solution of D-luciferin (Promega, Mannheim, Germany; 150 mg/kg body weight) was administered i.p. into mice. The animals were anesthetized with isofluorane and placed into the light-tight chamber of an IVIS Lumina imaging system (Xenogen, Rüsselsheim, Germany). 25 min after luciferin injection, photons emitted were quantified for an integration time of 1 min. Grayscale images of mice were used as a reference on which the bioluminescence signal was superimposed as a scaled pseudocolor image (black=least intense; white=most intense) by employing the Living Image software (Xenogen). To quantify the bioluminescence, regions of interest (ROI) were drawn and total flux (photons/sec, p/s) in ROI was measured. Background bioluminescence from a non-signal emitting region on the animal was subtracted from respective bioluminescence values for each animal.

Figure 5A:
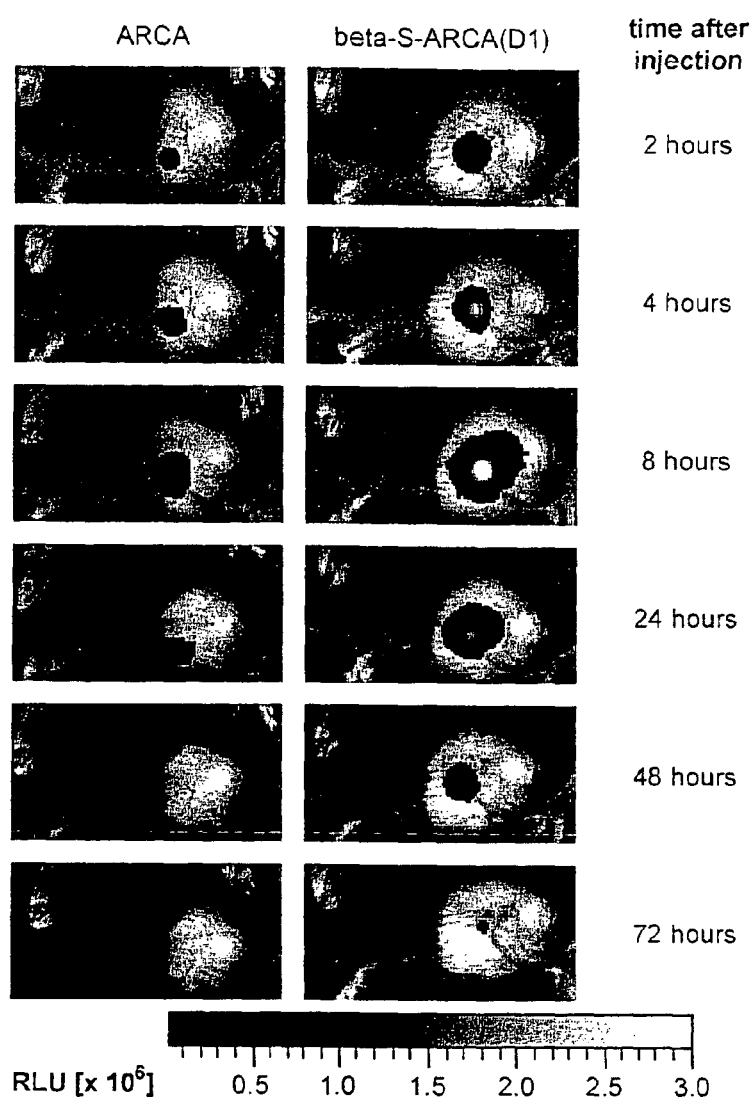
FIG. 5. Effect of the 5'-cap structure on protein expression in vivo. Mice (n=9) have been injected intranodally with the same amount of luciferase encoding RNA with ARCA or beta-S-ARCA(D1) at the 5'-end (as indicated). The luciferase activity (given in RLU) has been measured after 2, 4, 8, 24, 48, and 72 hours. (A) Images of whole animals at the indicated time points of a representative mouse, which has been injected with ARCA or beta-S-ARCA(D1) RNA are shown. The photon counts are illustrated corresponding to the grey scale shown in the figure. (B) Mean±standard error of the mean as measured in the time course. The significance has been determined using statistical analyses (*: P<0.005 and **: P<0.02).
Figure 5B:
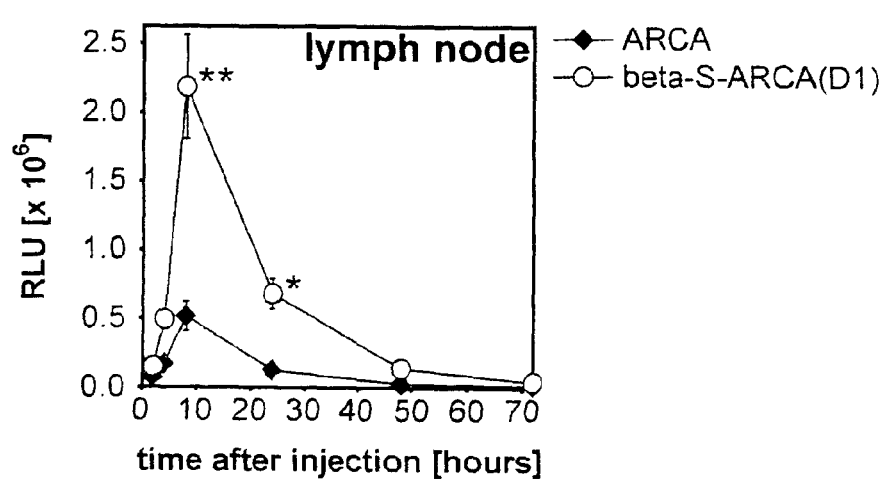

In accordance with the results in isolated immature dendritic cells we observed that the protein expression of RNA with beta-S-ARCA(D1) at the 5'-end was higher at each time point (2, 4, 8, 24, 48, and 72 hours after intranodal application of the RNA) as that of RNA with ARCA at the 5'-end (FIG. 5). Throughout the entire time course the expression (given by the integral of the curve) was increased by about 8-fold. Hence, we could show for the first time that by beta-S-ARCA (D1) the protein expression in lymph nodes, and thus, mainly in the immature dendritic cells resident therein, is enhanced in intensity and duration.

Example 7

Increased De Novo T-Cell Priming after Vaccination Using RNA with Beta-S-ARCA(D1) at the 5'-End The fusion of the antigen to an amino terminal leader peptide and a carboxy-terminal MHC class I trafficking signal results in an increased antigen-presentation of MHC class I and class II epitopes (Kreiter et al., 2008, J. Immunol. 180: 309-318). Intranodal injection of ARCA RNA encoding a respectively modified antigen and including the above described optimizations with respect to poly(A) sequence and beta-globin UTR allows for de novo priming of naïve T-cells (DE 10 2008 061 522.6). We have investigated whether de novo priming can be further enhanced by using beta-S-ARCA(D1).

Figure 6A:
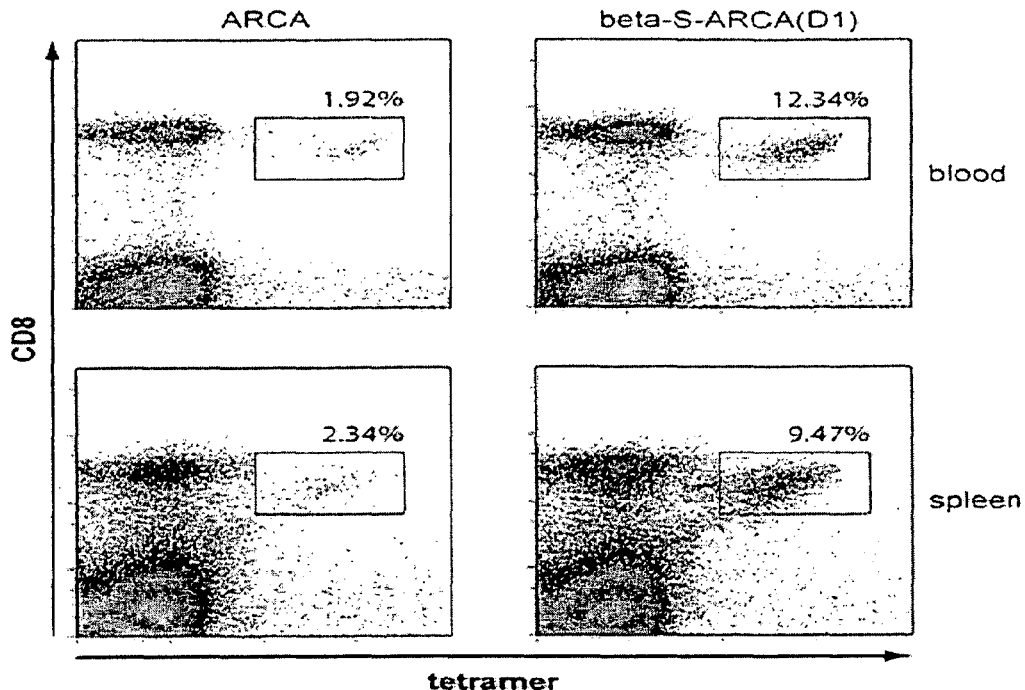
FIG. 6. Effect of the 5'-cap structure on de novo priming of T-cells after intranodal immunization with RNA. Mice (n=5) have been immunized by intranodal injection twice a day (day 0 and day 3) with the same amount of RNA encoding a specific peptide antigen which either carries ARCA or beta-S-ARCA(D1) at the 5'-end. The frequency of tetramer positive CD8$^+$-cells was determined on day 8 using tetramer analysis. (A) Representative dot plots of cells from the peripheral blood and the spleen of mice which have been immunized with ARCA or beta-S-ARCA(D1) RNA (as indicated). (B) Average number of tetramer positive CD8$^+$-cells±standard error of the mean (in %) as measured on day 8. The significance was determined using statistical analyses (*: P<0.075).
Figure 6B:
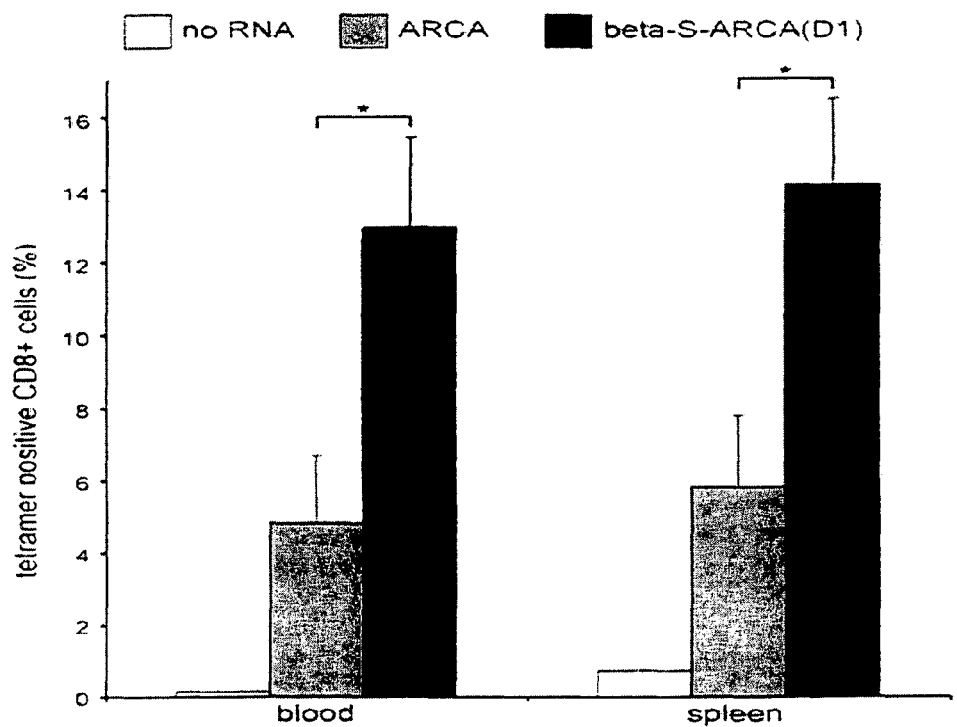

Mice were immunized by intranodal injection of naked RNA twice a day (at day 0 and at day 3) which encodes a specific antigen with the above modifications. On day 8 the frequency of antigen-specific T-cells in peripheral blood and in the spleen was determined using tetramer staining. As shown in FIG. 6 about 5% of the CD8⁺-T-cells in peripheral blood and about 6% of the CD8⁺-T-cells in the spleen were tetramer positive after duplicate immunization with ARCA RNA. Using beta-S-ARCA(D1) RNA more than 12% and 13% tetramer positive CD8⁺-T-cells in peripheral blood and in the spleen, respectively, were measured. This demonstrates for the first time that beta-S-ARCA(D1) leads to an enhanced and prolonged protein expression from the RNA carrying the beta-S-ARCA(D1) cap which then results in an enhanced immune response (measured as de novo priming of T-cells), even in the context of an antigen which has been optimized with respect to processing and transport to MHC class I and class II complexes and using a DNA template for preparation of an RNA with higher stability and translation efficiency.

Example 8

HPLC Analysis of $m_2^{7,2'-O}Gpp_spG$ (D1) and (D2) (i.e. Beta-S-ARCA(D1) and (D2))

Figure 7:
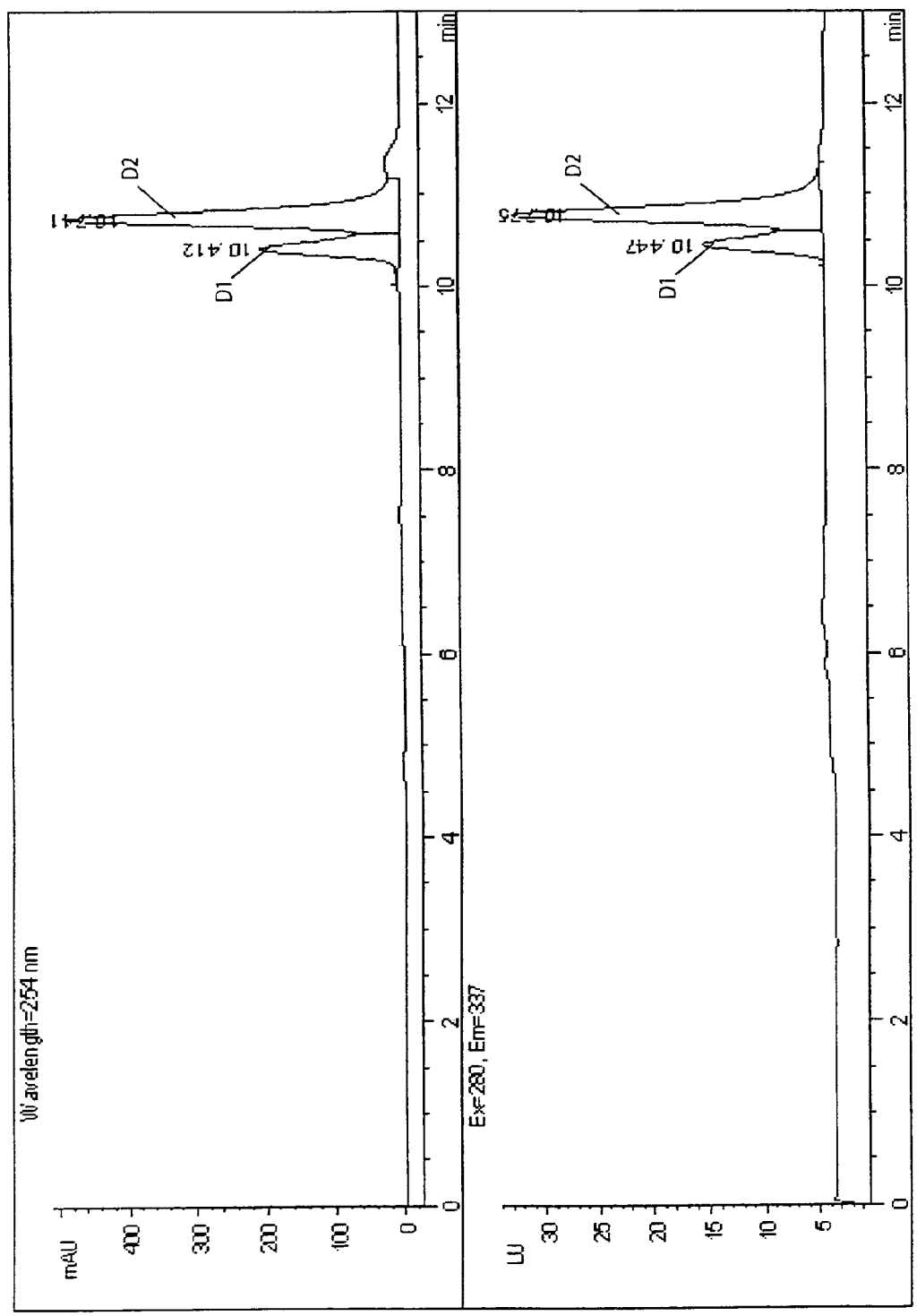
FIG. 7. HPLC analysis of $m_2^{7,2'-O}Gpp_spG$ (D1) and (D2) (i.e., beta-S-ARCA(D1) and (D2)). Analytical HPLC of a diastereomeric mixture with a molar ration of beta-S-ARCA (D1):(D2) of 1:3 was performed on an Agilent Technologies 1200 Series apparatus with a Supelcosil LC-18-T RP column (5 μm, 4.6×250 mm, flow rate: 1.3 ml/min) using a 0-25% linear gradient of methanol in 0.05 M ammonium acetate, pH=5.9, within 15 min. UV-detection (VWD) was performed at 260 nm and florescence detection (FLD) was performed with excitation at 280 nm and detection at 337 nm. Retention times: beta-S-ARCA(D1)=10.4 min, beta-S-ARCA(D2) =10.7 min.

Analytical HPLC analysis of a diastereomeric mixture of $m_2^{7,2'-O}Gpp_spG$ (D1) and (D2) (i.e., beta-S-ARCA(D1) and (D2)) in a molar ratio of about 1:3 has been performed on an Agilent Technologies 1200 Series apparatus with a Supelcosil LC-18-T RP column (5 μm, 4.6×250 mm, flow rate: 1.3 ml/min) using a 0-25% linear gradient of methanol in 0.05 M ammonium acetate, pH=5.9, within 15 min. UV-detection (VWD) was performed at 260 nm and florescence detection (FLD) was performed with excitation at 280 nm and detection at 337 nm. retention times: $m_2^{7,2'-O}Gpp_spG$ (D1)=10.4 min, $m_2^{7,2'-O}Gpp_spG$ (D2)=10.7 min (FIG. 7).

The invention claimed is:
1. A pharmaceutical composition comprising (i) one or more pharmaceutically acceptable adjuvants, carriers, diluents, carriers and/or excipients and (ii) an RNA modified with a 5'-cap structure according to formula (I):

Formula (I)

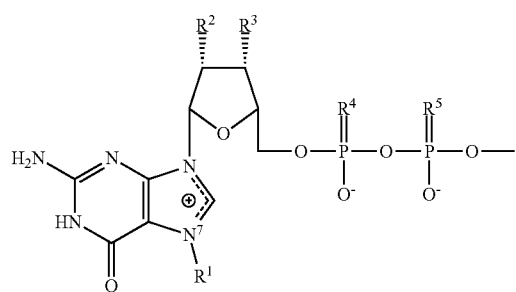

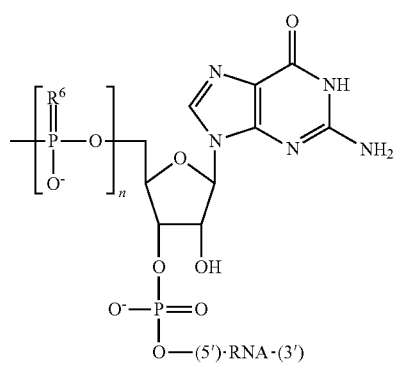

wherein R¹ is selected from the group consisting of optionally substituted alkyl, optionally substituted alkenyl, optionally substituted alkynyl, optionally substituted cycloalkyl, optionally substituted heterocyclyl, optionally substituted aryl, and optionally substituted heteroaryl, R² and R³ are independently selected from the group consisting of H, halo, OH, and optionally substituted alkoxy, or R² and R³ together form O—X—O, wherein X is selected from the group consisting of optionally substituted $CH_2$, $CH_2CH_2$, $CH_2CH_2CH_2$, $CH_2CH(CH_3)$, and $C(CH_3)_2$, or R² is combined with the valence produced by removal of the hydrogen atom at position 4' of the ring to which R² is attached, wherein the bridging linkage from R² to the 4' position is defined as an —O—$CH_2$— group or —$CH_2$—O— group, R⁵ is selected from the group consisting of S, Se, and $BH_3$, R⁴ and R⁶ are independently selected from the group consisting of O, S, Se, and $BH_3$, n is 1, 2, or 3, wherein the stereochemical configuration at the P atom comprising the substituent R⁵ corresponds to that at the $P_\beta$ atom of the D1 diastereomer of beta-S-ARCA:

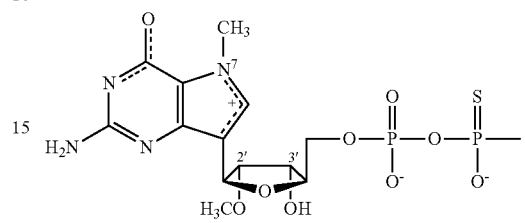

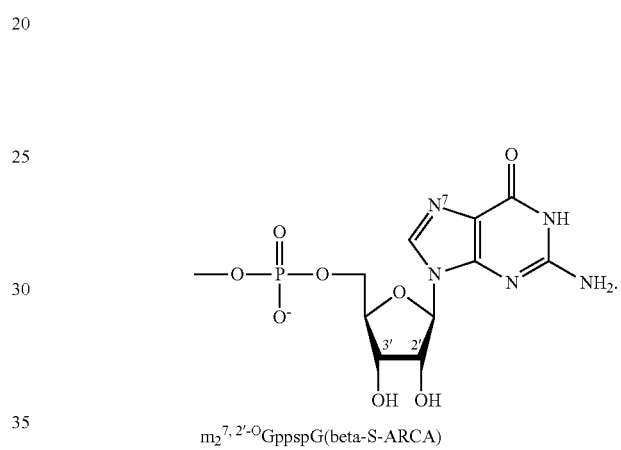

$m_2^{7, 2'-O}$GppspG(beta-S-ARCA)

2. The pharmaceutical composition of claim 1, wherein R¹ is selected from the group consisting of optionally substituted $C_1$-$C_4$ alkyl, optionally substituted $C_2$-$C_4$ alkenyl, and optionally substituted aryl.

3. The pharmaceutical composition of claim 1, wherein R² and R³ are independently selected from the group consisting of H, F, OH, methoxy, ethoxy, and propoxy.

4. The pharmaceutical composition of claim 1, wherein the RNA 5'-cap is the diastereomer D1 of beta-S-ARCA:

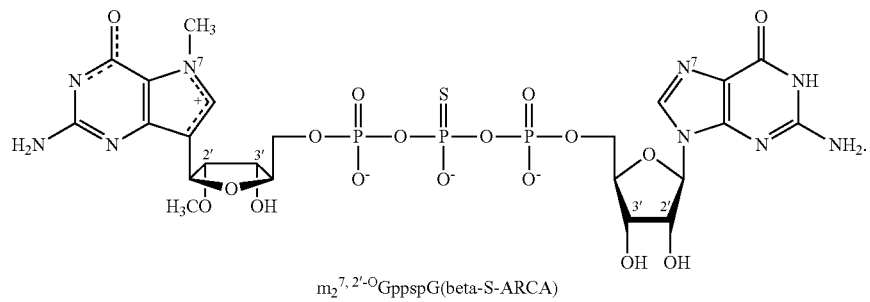

$m_2^{7, 2'-O}$GppspG(beta-S-ARCA)

5. A method for eliciting an immune response in an individual in need thereof comprising the step of administering to said individual the pharmaceutical composition of claim 1.

6. An isolated immature antigen presenting cell comprising an RNA encoding an antigen, a protein or peptide comprising said antigen, or an antigen peptide capable of eliciting an immune response against said antigen, which RNA is modified with a 5'-cap structure according to formula (I):

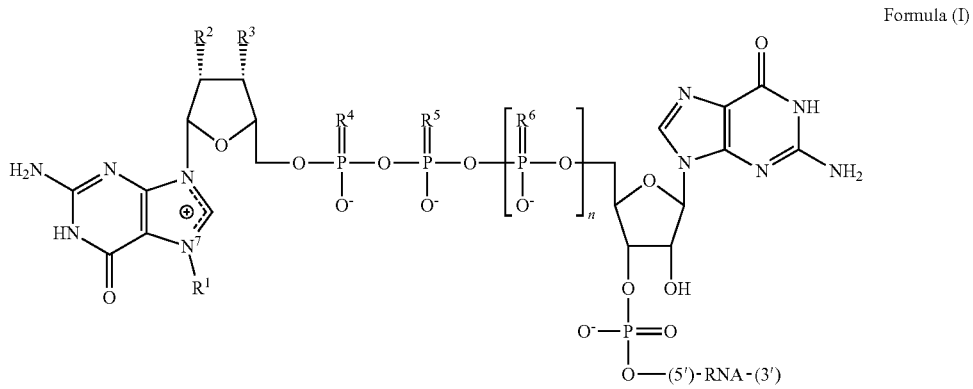

Formula (I)

wherein $R^1$ is selected from the group consisting of optionally substituted alkyl, optionally substituted alkenyl, optionally substituted alkynyl, optionally substituted cycloalkyl, optionally substituted heterocyclyl, optionally substituted aryl, and optionally substituted heteroaryl, $R^2$ and $R^3$ are independently selected from the group consisting of H, halo, OH, and optionally substituted alkoxy, or $R^2$ and $R^3$ together form O—X—O, wherein X is selected from the group consisting of optionally substituted $CH_2$, $CH_2CH_2$, $CH_2CH_2CH_2$, $CH_2CH(CH_3)$, and $C(CH_3)_2$, or $R^2$ is combined with the valence produced by removal of the hydrogen atom at position 4' of the ring to which $R^2$ is attached, wherein the bridging linkage from $R^2$ to the 4' position is defined as an —O—$CH_2$— group or —$CH_2$—O— group, $R^5$ is selected from the group consisting of S, Se, and $BH_3$, $R^4$ and $R^6$ are independently selected from the group consisting of O, S, Se, and $BH_3$, n is 1, 2, or 3, wherein the stereochemical configuration at the P atom comprising the substituent $R^5$ corresponds to that at the $P_\beta$ atom of the D1 diastereomer of beta-S-ARCA:

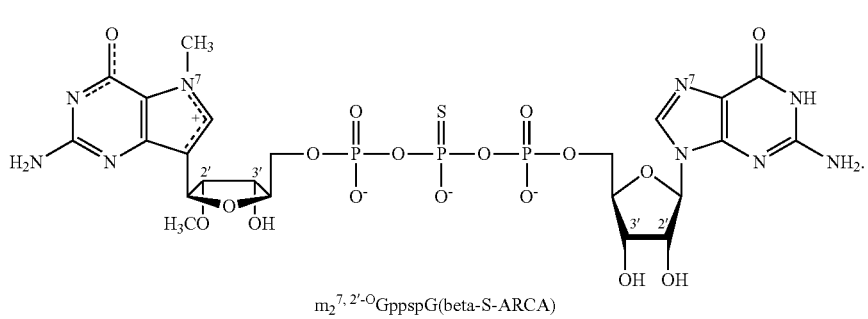

$m_2^{7, 2'-O}$GppspG(beta-S-ARCA)

7. A method for eliciting an immune response in an individual in need thereof comprising the step of administering to said individual the pharmaceutical composition of claim 1 or the isolated immature antigen presenting cell of claim 6.

8. The method of eliciting the immune response in the individual of claim 7, further comprising increasing the stability of the RNA, increasing translation efficiency of the RNA, prolonging translation of the RNA, increasing total protein expression of the RNA, or increasing the immune response against an antigen or antigen peptide encoded by said RNA facilitated by the 5'-cap structure upon transfer of said RNA into the immature antigen presenting cell when compared to the same RNA without the 5'-cap structure according to formula (I).

9. A method for increasing the stability of an RNA in an immature antigen presenting cell in need thereof or for increasing the expression of an RNA in an immature antigen presenting cell in need thereof, said method comprising:

providing said RNA with a 5'-cap structure according to formula (I):

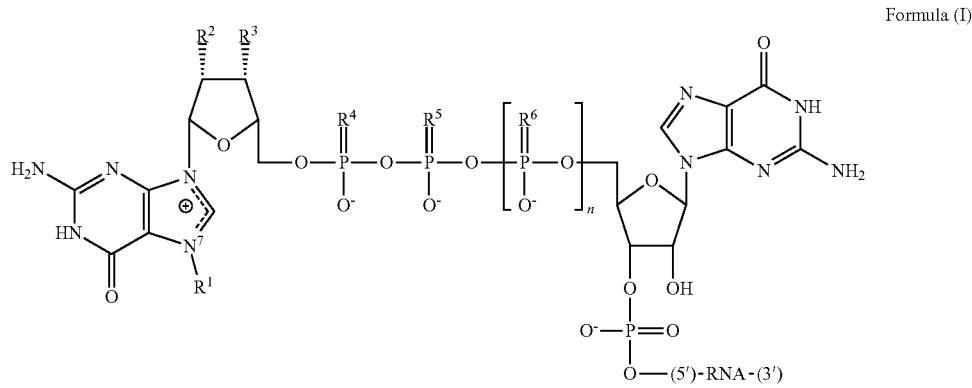

Formula (I)

wherein $R^1$ is selected from the group consisting of optionally substituted alkyl, optionally substituted alkenyl, optionally substituted alkynyl, optionally substituted cycloalkyl, optionally substituted heterocyclyl, optionally substituted aryl, and optionally substituted heteroaryl, $R^2$ and $R^3$ are independently selected from the group consisting of H, halo, OH, and optionally substituted alkoxy, or $R^2$ and $R^3$ together form O—X—O, wherein X is selected from the group consisting of optionally substituted $CH_2$, $CH_2CH_2$, $CH_2CH_2CH_2$, $CH_2CH(CH_3)$, and $C(CH_3)_2$, or $R^2$ is combined with the valence produced by removal of the hydrogen atom at position 4' of the ring to which $R^2$ is attached, wherein the bridging linkage from $R^2$ to the 4' position is defined as an —O—$CH_2$— group or —$CH_2$—O— group, $R^5$ is selected from the group consisting of S, Se, and $BH_3$, $R^4$ and $R^6$ are independently selected from the group consisting of O, S, Se, and $BH_3$, n is 1, 2, or 3, wherein the stereochemical configuration at the P atom comprising the substituent $R^5$ corresponds to that at the $P_\beta$ atom of the D1 diastereomer of beta-S-ARCA:

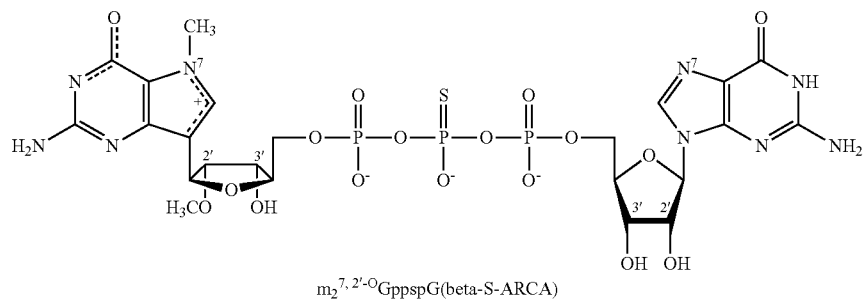

$m_2^{7,2'-O}$GppspG(beta-S-ARCA)

and
transferring said RNA into the immature antigen presenting cell.

10. A method for increasing the portion of major histocompatibility complex (MHC) molecules which present an antigen of interest on the surface of an antigen presenting cell in need thereof, said method comprising:

providing an RNA comprising a nucleotide sequence encoding a peptide or protein comprising said antigen of interest or an antigen peptide thereof, said RNA being modified with a 5'-cap structure according to formula (I):

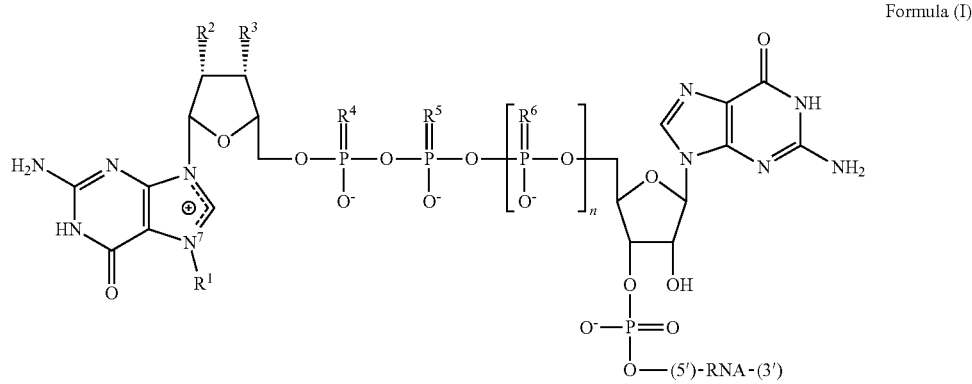

Formula (I)

wherein $R^1$ is selected from the group consisting of optionally substituted alkyl, optionally substituted alkenyl, optionally substituted alkynyl, optionally substituted cycloalkyl, optionally substituted heterocyclyl, optionally substituted aryl, and optionally substituted heteroaryl, $R^2$ and $R^3$ are independently selected from the group consisting of H, halo, OH, and optionally substituted alkoxy, or $R^2$ and $R^3$ together form O—X—O, wherein X is selected from the group consisting of optionally substituted $CH_2$, $CH_2CH_2$, $CH_2CH_2CH_2$, $CH_2CH(CH_3)$, and $C(CH_3)_2$, or $R^2$ is combined with the valence produced by removal of the hydrogen atom at position 4' of the ring to which $R^2$ is attached, wherein the bridging linkage from $R^2$ to the 4' position is defined as an —O—$CH_2$— group or —$CH_2$—O— group, $R^5$ is selected from the group consisting of S, Se, and $BH_3$, $R^4$ and $R^6$ are independently selected from the group consisting of O, S, Se, and $BH_3$, n is 1, 2, or 3, wherein the stereochemical configuration at the P atom comprising the substituent $R^5$ corresponds to that at the $P_\beta$ atom of the D1 diastereomer of beta-S-ARCA:

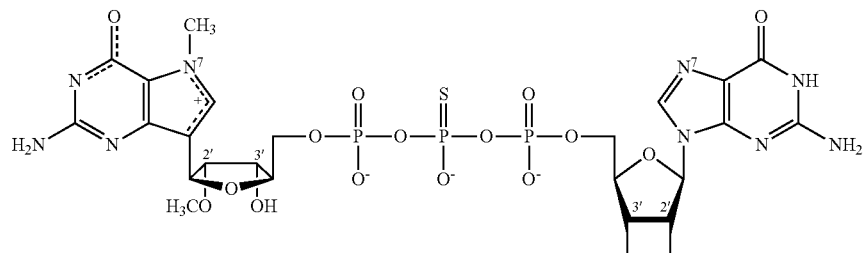

$m_2^{7, 2'-O}$GppspG(beta-S-ARCA)

and
transferring said RNA into an immature antigen presenting cell.

11. A method for stimulating and/or activating immune effector cell in need thereof, said method comprising:

providing an RNA comprising a nucleotide sequence encoding a peptide or protein comprising an antigen of interest or an antigen peptide thereof, said RNA being modified with a 5'-cap structure according to formula (I):

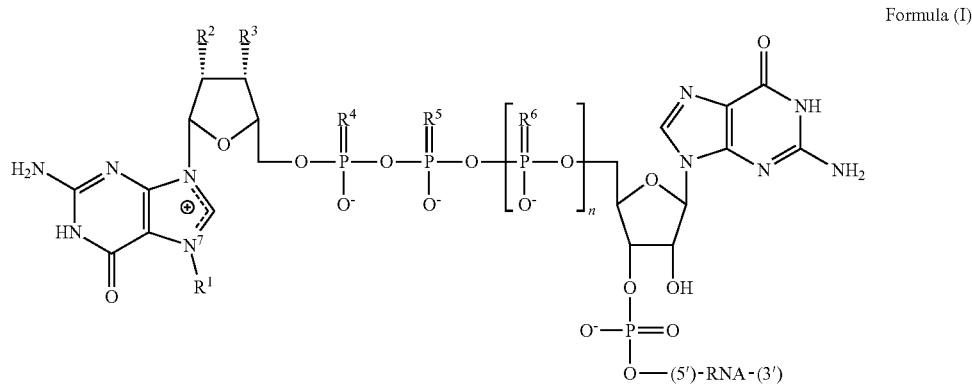

Formula (I)

wherein $R^1$ is selected from the group consisting of optionally substituted alkyl, optionally substituted alkenyl, optionally substituted alkynyl, optionally substituted cycloalkyl, optionally substituted heterocyclyl, optionally substituted aryl, and optionally substituted heteroaryl, $R^2$ and $R^3$ are independently selected from the group consisting of H, halo, OH, and optionally substituted alkoxy, or $R^2$ and $R^3$ together form O—X—O, wherein X is selected from the group consisting of optionally substituted $CH_2$, $CH_2CH_2$, $CH_2CH_2CH_2$, $CH_2CH(CH_3)$, and $C(CH_3)_2$, or $R^2$ is combined with the valence produced by removal of the hydrogen atom at position 4' of the ring to which $R^2$ is attached, wherein the bridging linkage from $R^2$ to the 4' position is defined as an —O—$CH_2$— group or —$CH_2$—O— group, $R^5$ is selected from the group consisting of S, Se, and $BH_3$, $R^4$ and $R^6$ are independently selected from the group consisting of O, S, Se, and $BH_3$, n is 1, 2, or 3, wherein the stereochemical configuration at the P atom comprising the substituent $R^5$ corresponds to that at the $P_\beta$ atom of the D1 diastereomer of beta-S-ARCA:

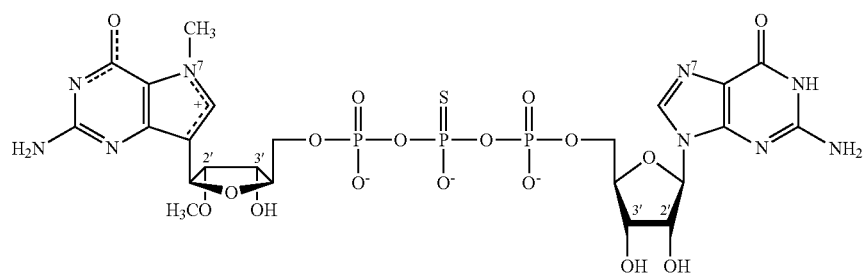

$m_2^{7,2'-O}GppspG(beta-S-ARCA)$ transferring said RNA into an immature antigen presenting cell, and
administration of the antigen presenting cell to a host comprising an immune effector cell.

12. The method of claim 11, wherein administration of the antigen presenting cell to the host comprising the immune effector cell is accomplished in vitro.

13. A method for inducing an immune response in an individual in need thereof, said method comprising: providing an RNA comprising a nucleotide sequence encoding a peptide or protein comprising an antigen of interest or an antigen peptide thereof, said RNA being modified with a 5'-cap structure according to formula (I):

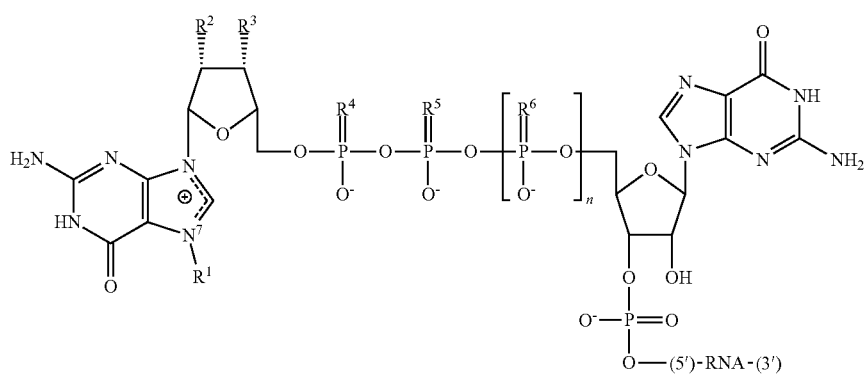

Formula (I)

wherein $R^1$ is selected from the group consisting of optionally substituted alkyl, optionally substituted alkenyl, optionally substituted alkynyl, optionally substituted cycloalkyl, optionally substituted heterocyclyl, optionally substituted aryl, and optionally substituted heteroaryl, $R^2$ and $R^3$ are independently selected from the group consisting of H, halo, OH, and optionally substituted alkoxy, or $R^2$ and $R^3$ together form O—X—O, wherein X is selected from the group consisting of optionally substituted $CH_2$, $CH_2CH_2$, $CH_2CH_2CH_2$, $CH_2CH(CH_3)$, and $C(CH_3)_2$, or $R^2$ is combined with the valence produced by removal of the hydrogen atom at position 4' of the ring to which $R^2$ is attached, wherein the bridging linkage from $R^2$ to the 4' position is defined as an —O—$CH_2$— group or —$CH_2$—O— group, $R^5$ is selected from the group consisting of S, Se, and $BH_3$, $R^4$ and $R^6$ are independently selected from the group consisting of O, S, Se, and $BH_3$, n is 1, 2, or 3, wherein the stereochemical configuration at the P atom comprising the substituent $R^5$ corresponds to that at the $P_\beta$ atom of the D1 diastereomer of beta-S-ARCA:

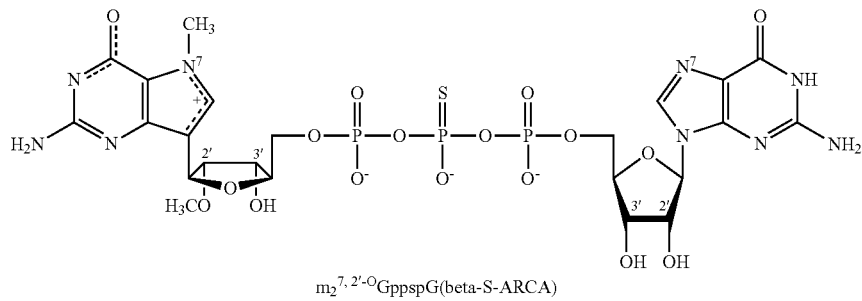

$m_2^{7,\,2'\text{-}O}GppspG(\text{beta-S-ARCA})$ and
administering said RNA to said individual.

14. The method of claim 13, wherein the RNA is administered by intranodal injection.

15. A method for inducing an immune response in an individual in need thereof, said method comprising:

providing an RNA comprising a nucleotide sequence encoding a peptide or protein comprising an antigen of interest or an antigen peptide thereof, said RNA being modified with a 5'-cap structure according to formula (I):

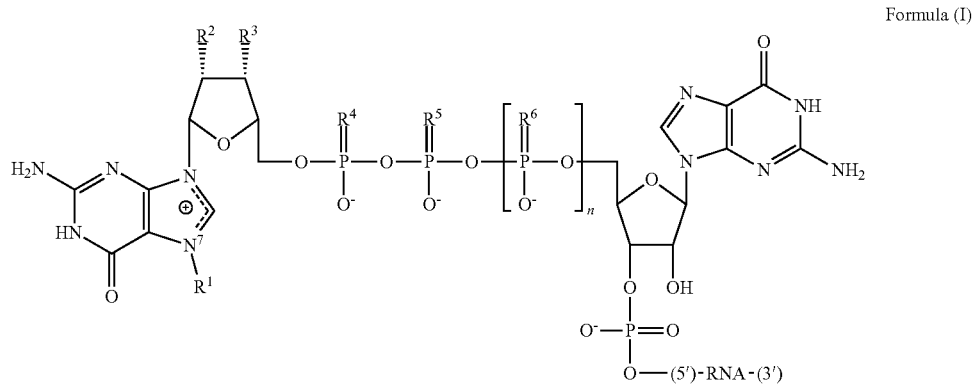

Formula (I)

wherein $R^1$ is selected from the group consisting of optionally substituted alkyl, optionally substituted alkenyl, optionally substituted alkynyl, optionally substituted cycloalkyl, optionally substituted heterocyclyl, optionally substituted aryl, and optionally substituted heteroaryl, $R^2$ and $R^3$ are independently selected from the group consisting of H, halo, OH, and optionally substituted alkoxy, or $R^2$ and $R^3$ together form O—X—O, wherein X is selected from the group consisting of optionally substituted $CH_2$, $CH_2CH_2$, $CH_2CH_2CH_2$, $CH_2CH(CH_3)$, and $C(CH_3)_2$, or $R^2$ is combined with the valence produced by removal of the hydrogen atom at position 4' of the ring to which $R^2$ is attached, wherein the bridging linkage from $R^2$ to the 4' position is defined as an —O—$CH_2$— group or —$CH_2$—O— group, $R^5$ is selected from the group consisting of S, Se, and $BH_3$, $R^4$ and $R^6$ are independently selected from the group consisting of O, S, Se, and $BH_3$, n is 1, 2, or 3, wherein the stereochemical configuration at the P atom comprising the substituent $R^5$ corresponds to that at the $P_\beta$ atom of the D1 diastereomer of beta-S-ARCA:

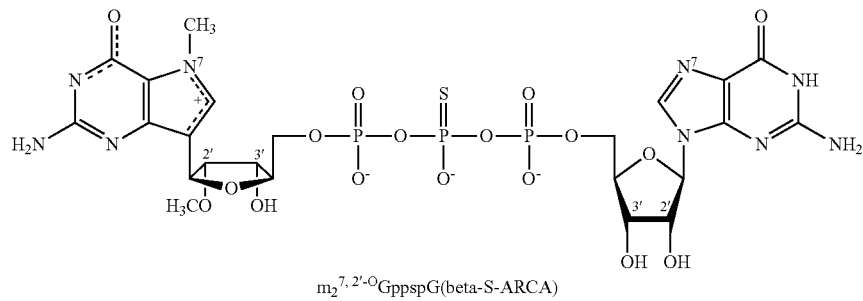

$m_2^{7, 2'-O}$GppspG(beta-S-ARCA)

transferring said RNA into an immature antigen presenting cell, and administering the antigen presenting cell to said individual.

16. A method for eliciting an immune response in an individual in need thereof comprising the step of administering to said individual the isolated immature antigen presenting cell of claim 7.

* * * * *